United States Patent
Najib et al.

(10) Patent No.: US 8,106,097 B2
(45) Date of Patent: *Jan. 31, 2012

(54) COMPOSITION BASED ON SUBSTITUTED 1,3-DIPHENYLPROP-2-EN-1-ONE DERIVATIVES, PREPARATION AND USES THEREOF

(75) Inventors: Jamila Najib, Santes (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/609,270

(22) Filed: Oct. 30, 2009

(65) Prior Publication Data

US 2010/0120909 A1     May 13, 2010

Related U.S. Application Data

(63) Continuation of application No. 10/520,078, filed as application No. PCT/FR03/02128 on Jul. 8, 2003, now Pat. No. 7,632,870.

(30) Foreign Application Priority Data

Jul. 8, 2002 (FR) .................. 02 08570

(51) Int. Cl.
- *A61K 31/12* (2006.01)
- *A61K 31/03* (2006.01)
- *A61K 31/015* (2006.01)
- *A01N 29/12* (2006.01)

(52) U.S. Cl. ........ 514/685; 514/686; 514/748; 514/764; 514/766

(58) Field of Classification Search .................. 514/685, 514/686, 748, 764, 766

See application file for complete search history.

(56) References Cited

U.S. PATENT DOCUMENTS

| | | | |
|---|---|---|---|
| 3,558,612 | A | 1/1971 | Kuhn et al. |
| 3,994,955 | A | 11/1976 | Sprenger |
| 4,190,671 | A | 2/1980 | Vanstone et al. |
| 4,656,305 | A | 4/1987 | Vanstone et al. |
| 5,276,058 | A | 1/1994 | Satoh et al. |

(Continued)

FOREIGN PATENT DOCUMENTS

DE    43 27 365    2/1995

(Continued)

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*

(Continued)

*Primary Examiner* — San-Ming Hui
*Assistant Examiner* — Paul Zarek
(74) *Attorney, Agent, or Firm* — Nixon & Vanderhye P.C.

(57) ABSTRACT

The invention concerns compositions comprising substituted 1,3-diphenylprop-2-en-1-one derivatives designed for therapeutic use. The inventive compositions are useful in particular for preventing or treating cardiovascular diseases, syndrome X, Ia restenosis, diabetes, obesity, hypertension, inflammatory diseases, cancers or neoplasms (benign or malignant tumors), neurodegenerative, dermatological diseases and disorders related to oxidative stress, for preventing or treating the effects of ageing in general and for example skin ageing, in particular in the field of cosmetics (occurrence of wrinkles and the like).

9 Claims, 21 Drawing Sheets

U.S. PATENT DOCUMENTS

Figures 2, 3, 4, 5, 6, 7:
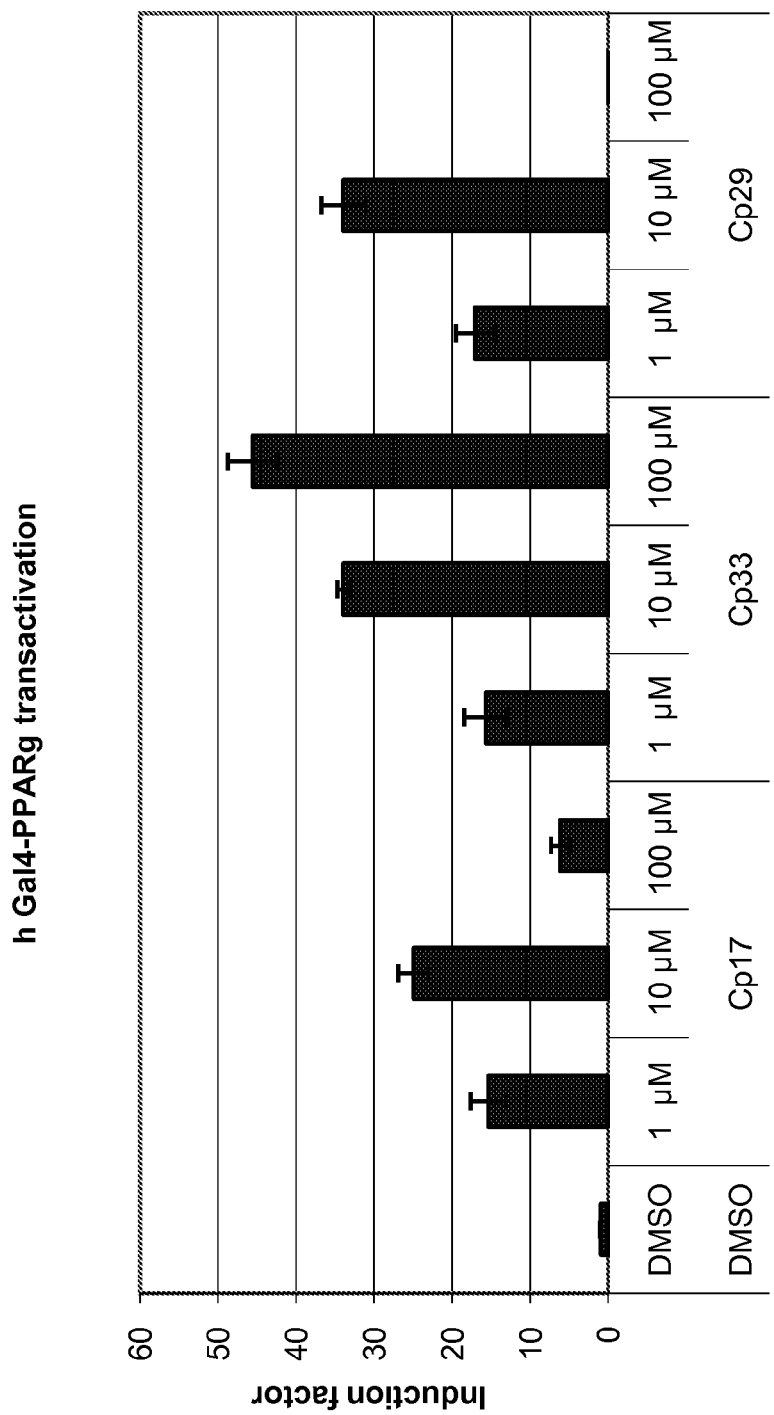

| | | | |
|---|---|---|---|
| 5,326,670 A | 7/1994 | Kotachi et al. | |
| 5,523,302 A | 6/1996 | Cain et al. | |
| 7,385,082 B2 | 6/2008 | Delhomel et al. | |
| 7,566,737 B2 * | 7/2009 | Delhomel et al. | 514/432 |
| 2005/0171149 A1 | 8/2005 | Najib et al. | |
| 2005/0176808 A1 | 8/2005 | Najib et al. | |

FOREIGN PATENT DOCUMENTS

| | | |
|---|---|---|
| EP | 0 947 511 | 10/1999 |
| EP | 1 254 658 | 11/2002 |
| EP | 1 254 759 | 11/2002 |
| FR | 2 248 829 | 5/1975 |
| FR | 2 383 157 | 8/1977 |
| FR | 78 06279 | 10/1978 |
| FR | 2 841 900 | 1/2004 |
| WO | WO 98/27970 | 7/1998 |
| WO | WO 00/23073 | 4/2000 |
| WO | WO 01/98291 | 12/2001 |
| WO | WO 2004/005233 | 1/2004 |
| WO | WO 2004/005243 | 1/2004 |

OTHER PUBLICATIONS

Shibata et al, "Anti-Tumorigenic Chalcones", Stem Cells, Alphamded Press, Dayton, OH, US, vol. 12, 1994, pp. 44-52.

Dimmock et al, "Bioactivities of Chalcones", Current Medicinal Chemistry, Bentham Science Publishers BV, BE, vol. 6, No. 12, 1999, pp. 1125-1149.

Lebeau et al, "Antioxidant Properties of Di-Tert-Butylhydroxylated Flavonoids", Free Radical Biology and Medicine, Elsevier Science, XX, vol. 29, No. 9, Nov. 1, 2000, pp. 900-912.

Mukherjee et al, "Synthetic and Biological Activity Evaluation Studies on Nove, 1,3-diarylpropenones", Bioorganic & Medicineal Chemistry, Elsevier Science Ltd, GB, vol. 9, No. 2, 2001, pp. 337-345.

Rajakumar et al, "Antioxidant Properties of Phenyl Styryl Ketones", Free Radical Research, Yverdon, CH, vol. 22, No. 4, 1995, pp. 309-317.

Arty, "Synthesis of benzylideneacetophenones and their inhibition of lipid peroxidation", European Journal of Medicinal Chemistry 2000 France, vol. 35, No. 4, 2000, pp. 449-457.

Halliwell, "Oxidants and the central nervous system: some fundamental questions. Is oxidant damage relevant to Parkinson's disease, Alzheimer's disease, traumatic injury or stroke?", Acta Neurologica Scandinavica. Supplementum. Denmark 1989, vol. 126, 1989, pp. 23-33.

Sogawa et al, "3,4-Dihydroxychalcones as Potent 5-Lipoxygenase and Cyclooxygenase Inhibitors", Journal of Medicinal Chemistry, American Chemical Society, Washington, US, vol. 36, No. 24, 1993, pp. 3904-3909.

Nakamura et al, "Synthesis and Biological Activities of Fluorinated Chalcone Derivativs", Bioorganic & Medicinal Chemistry, Elsevier Science Ltd, GB, vol. 10, No. 3, Mar. 2002, pp. 699,706.

Calliste et al, "Chalcones: Structural Requirements for Antioxidant, Estrogenic and Antiproliferative Activities", Anticancer Research, Helenic Anticancer Institute, Athens, GR, vol. 21, No. 6A, 2001, pp. 3949-3956.

Furmn et al, "Di-tert-Butylhydroxylated Flavonoids Protect Endothelial Cells Against Oxidized LDL-Induced Cytotocity", Journal of Biochemical and Molecular Toxicology, Wiley, New York, NY, US, vol. 15, No. 5, 2001, pp. 270-278.

Lim et al, "Synthesis of flavonoids and their effects on aldose reductase and sorbitol accumulation in streptozotocin-induced diabetic rat tissues", Journal of Pharmacy and Pharmacology, London, GB, vol. 53, No. 5, May 2001, pp. 653-668.

Patent Abstracts of Japan, vol. 018, No. 415, Aug. 4, 1994 & JP 06 122623 A, May 6, 1994.

Patent Abstracts of Japan, vol. 012, No. 209, Jun. 15, 1988 & JP 63 010720 A, Jan. 18, 1988.

Haraguchi et al, "Antioxidative and Superoxide Scavenging Activities of Retrochalcones in Glycyrrhiza Inflata", Bioorganic & Medicinal Chemistry, Elsevier Science Ltd, GB, vol. 6, No. 3, Mar. 1998, pp. 339-347.

Chemical Abstracts Service XP002236041, abstract & Oganesyan et al, "Study of structure-activity (A) interrelations in the flavonoid series. I. Synthesis of chalcome derivatives and quantitative SA analysis", Khimiko-Farmatseviicheskii Zhurnal, vol. 20, No. 6, 1986, pp. 696-702.

Hsu et al, Structure-Activity Relationships of Substituted Flavonoids. (I), Taiwan-Kexue—Formosanscience, Taipei, TW, vol. 27, No. 1/2, 1973, pp. 23-26.

Szajda et al, "New alkoxycarbonylalkyl oxychalcones and their alpha, beta-dibromo derivatives of potential antimicrobial activity", Die Pharmazie, Germany, East Mar. 1989, vol. 44, No. 3, pp. 190-191.

Stoll et al, "Chalcone derivatives antagonize interactions between the human oncoprotein MDM2 and p53", Biochemistry, American Chemical Society. Easton, PA, US, vol. 40, No. 2, Jan. 16, 2001, pp. 336-344.

Database, Chemical Abstracts Service, XP002271329, abstract & Shi et al, "Synthesis of ethyl flavone (or chalcone) oxyisobutyrate and its derivatives as antilipemic agents", Taiwan Yaoxue Xazhi, vol. 27, No. 1-2, 1975, pp. 12-16.

Database Chemical Abstracts Service, XP002271330, abstract & Palanowski et al, "Synthesis of potentiao vasoactive compounds. I. phenylacrylophenone derivatives", Acta Poloniae Pharmaceutica (English Translation), vol. 24, No. 6, 1967, pp. 567-574.

Database, Chemical Abstracts Service, XP002271331, abstract & JP 54 019947 A (Taisho Pharmaceutical Co.) Feb. 15, 1979.

Database, Chemical Abstracts Service, XP002271332, abstract & Safak et al, "Chalcones. II. Synthesis of some chalcone derivatives and their antifungal activity against *Candida albicans*", Fabad Farmasotik Bilimler Dergisi, vol. 8, No. 2, 1983, pp. 80-88.

Database, Chemical Abstracts Service, XP002271333, abstract & JP 05 255655 A, (Kanebo Ltd), Oct. 5, 1993.

Database, Chemical Abstracts Service, XP002271334, abstract & Sun et al, "Studies on flavonoids. VIIII. Synthesis of 7-substituted flavones and 2',4-dihydroxy-3-methoxy-4'-substituted chalcones", Gaodeng Xuexiao Huaxue Xuebao, vol. 9, No. 8, 1988, pp. 853.855.

Database, Chemical Abstracts Service, XP002271335, abstract & Szajda et al, Carbon 13 NMR study of o-, m- and p-' (alkoxycarbonyl)alkoxy chalcones and their alpha, beta dibromo derivatives, Magnetic Resonance in Chemistry, vol. 27, No. 4, 1989, pp. 399-402.

Cheng et al, "Broussochalcone A, a potent antioxidant and effective suppressor of inducible nitric oxide synthase in lipopolysaccharide-activated macrophages", Biochemical Pharmacology 61 (2001) 939-946.

Cheng et al, "Antioxidant properties of butein isolated from *Dalbergia odorifera*", Biochemica et Biophyics Acta 1392 (1908) 291-299.

Hsieh et al, "Synthesis and Anti-inflammatory Effect of Chalcones and Related Compounds", Pharmaceutical Research, vol. 15, No. 1, 1998, pp. 39-46.

U.S. Appl. No. 11/493,040, filed Jul. 2006, Delhomel et al.

U.S. Appl. No. 10/520,079, filed Apr. 2005, Najib et al.

Database Chemical Abstracts Service, XP002236011, abstract & Zhang et al, "Antioidation of Peurperia lobata isoflavones", Tongji Yike Dauxe Xeubao, vol. 26, No. 5, 1997, pp. 340-342.

Lebeau et al, "Beneficial effects of different flavonoids, on functional recovery after ischemia and reperfusion in isolated rat heart", Bioorganic & Medicinal Chemistry Letters, vol. 11, No. 1, Jan. 8, 2001, pp. 23-27.

Patent Abstracts of Japan vol. 014, No. 126, Mar. 9, 1990 & JP 02 003670 A Jan. 9, 1990.

Byrn, et al, "Solid State Chemistry of Drugs", $2^{nd}$ ed., SSCI, Inc., Chapter 10, p. 232-247, 1999.

French et al, "A New Preparation of Substituted 4H-1-Benzothiopyran-4-ones from C(a),N-Benzyolhydrazones or C(a),N-Carboalkoxyhydrazones and Methyl Thiosalicylate," Journal of Heterocyclic Chemistry, 1998, 35, 45-48.

King "Bioisosteres, conformational restriction and pro-drugs-case history: an example of a conformational restriction approach", Medical Chemistry: Principles and Practice, 1994, Chapter 14, 206-209.

* cited by examiner

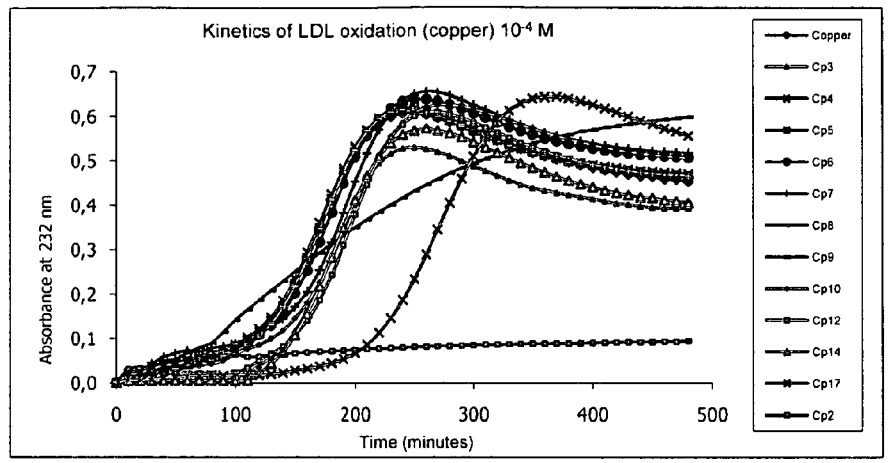
Figure: 1-1
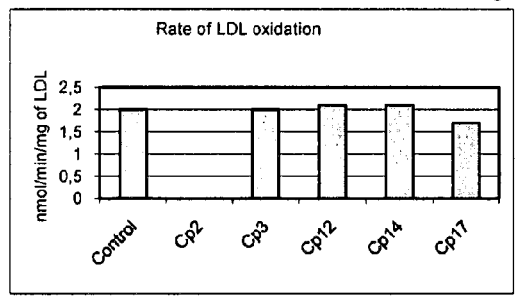
Figure: 1-2
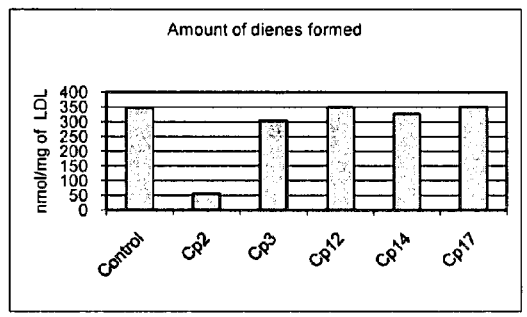
Figure: 1-3
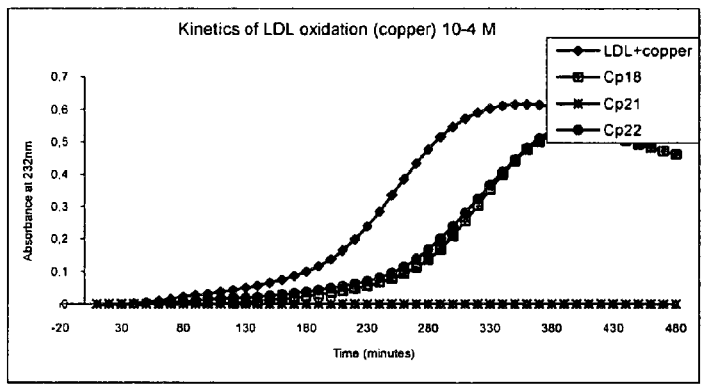
Figure: 1-4

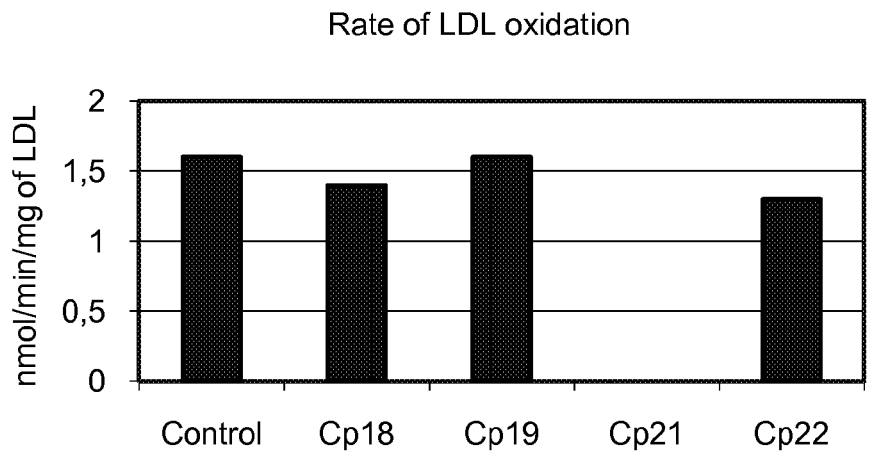
Figure : 1-5
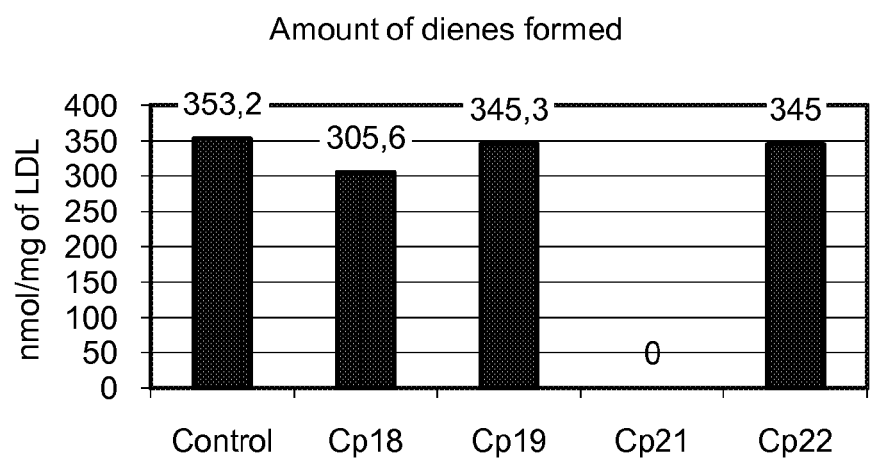
Kinetics of LDL oxidation (copper) $10^{-4}$ M
Figure : 1-6

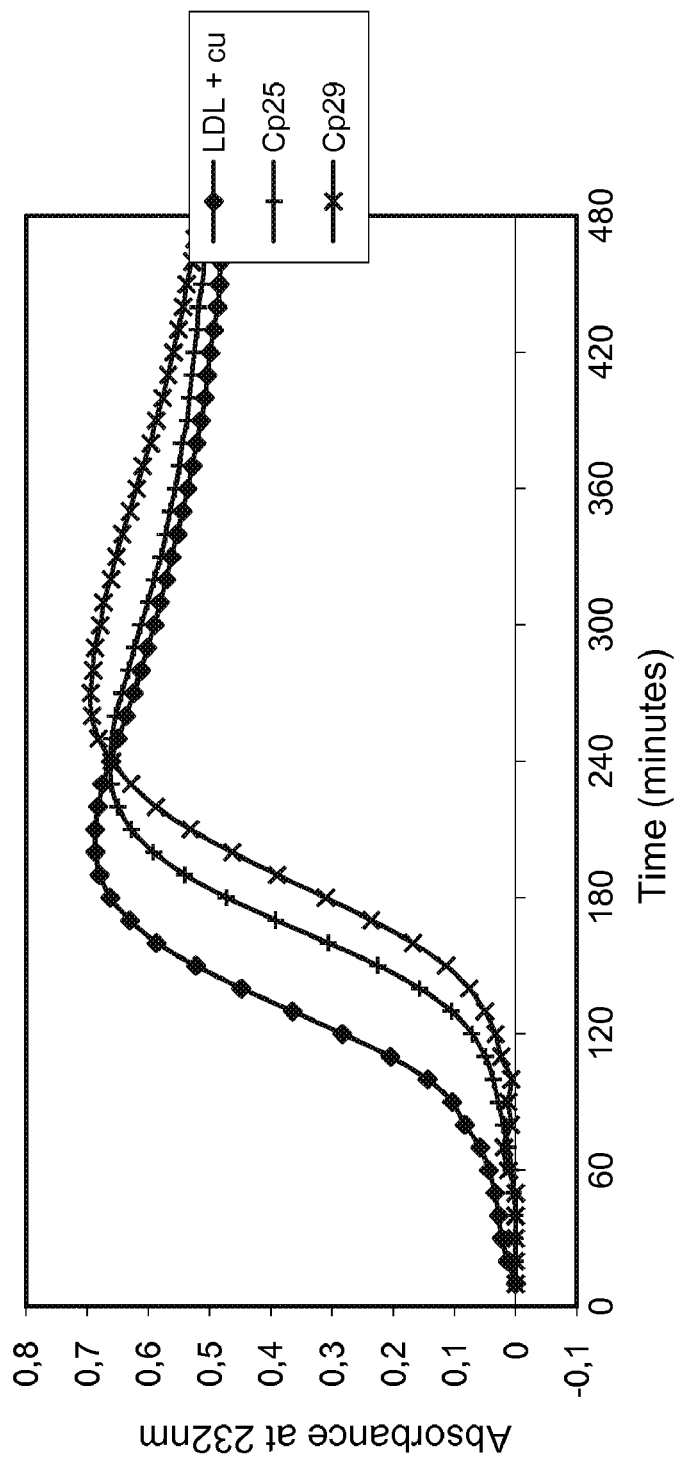
Figure : 1-7

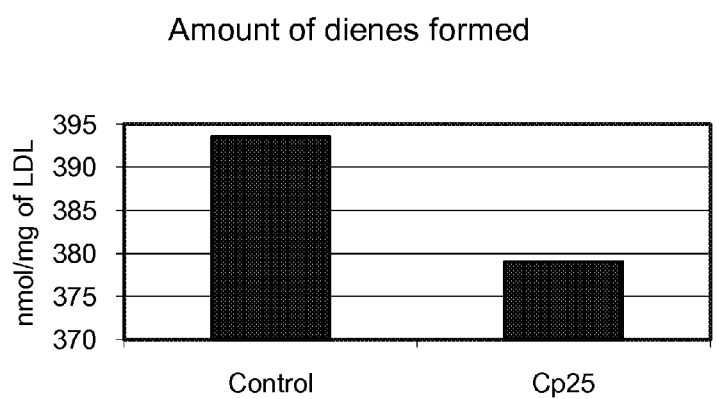
Figure : 1-8
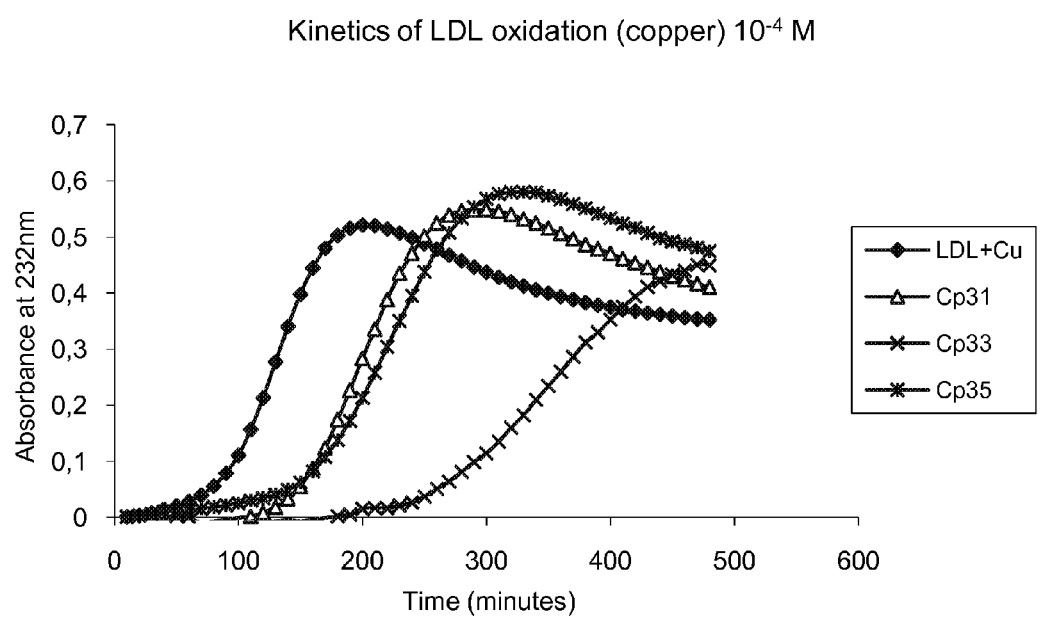
Figure : 1-9

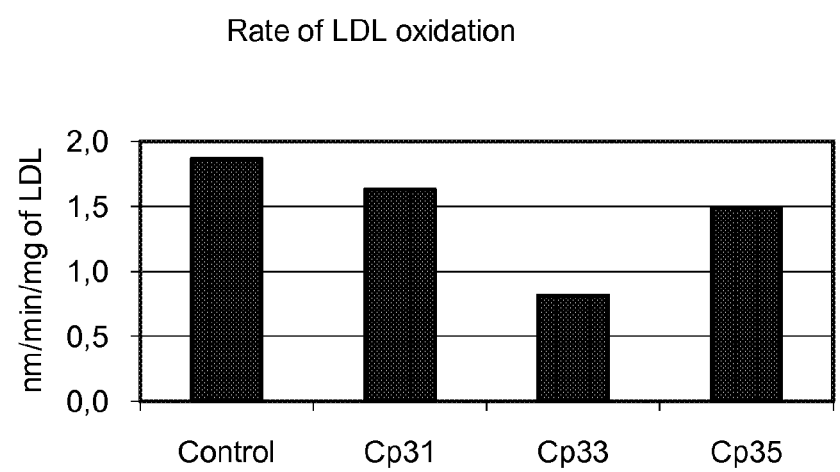
Figure : 1-10
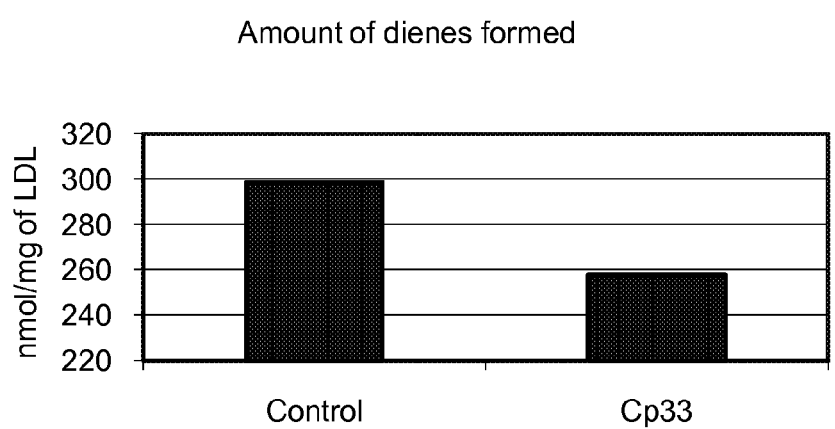
Figure : 1-11

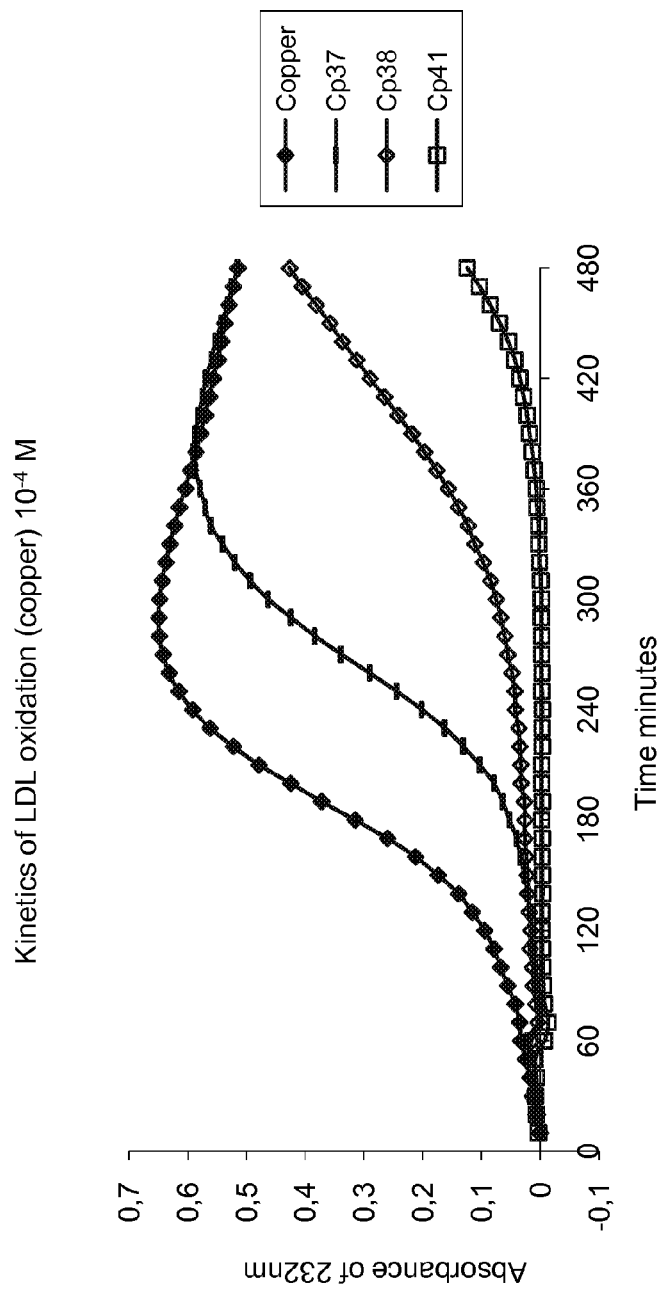
Figure : 1-12

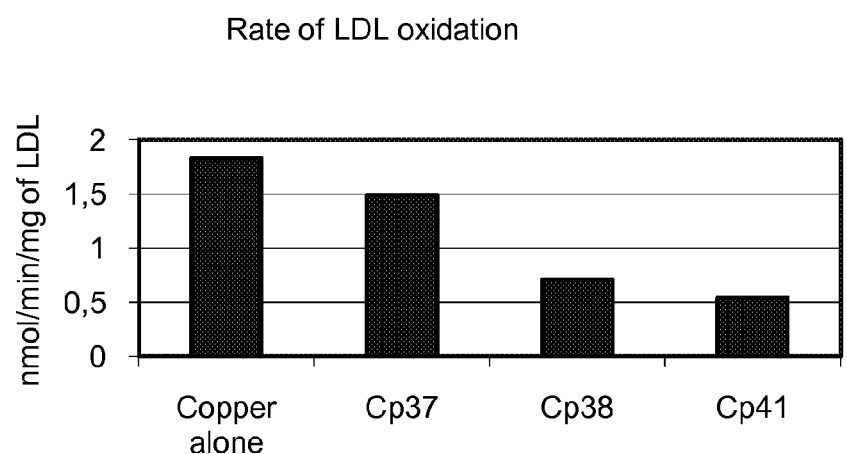
Figure : 1-13
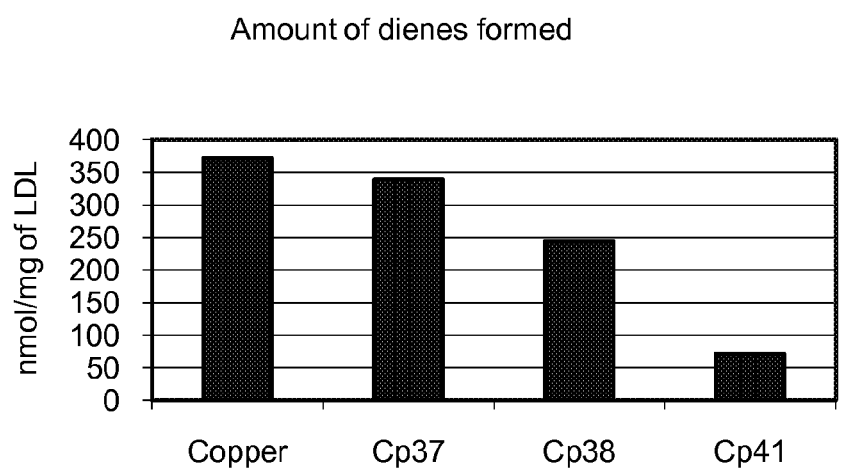
Figure : 1-14

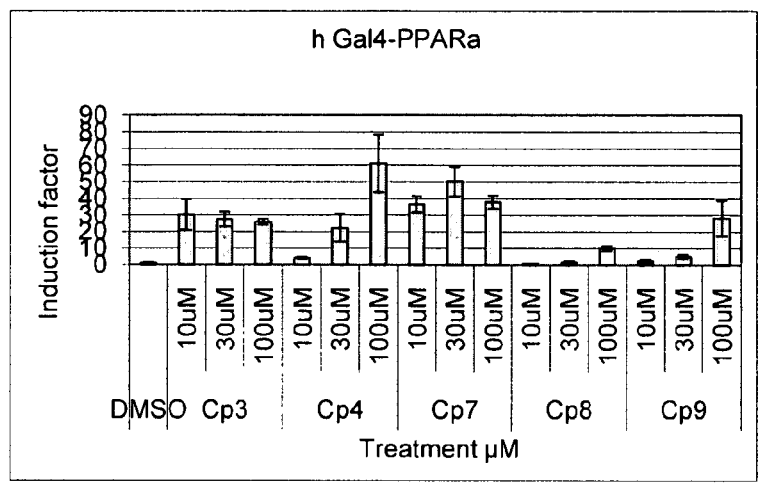
Figure : 2-1
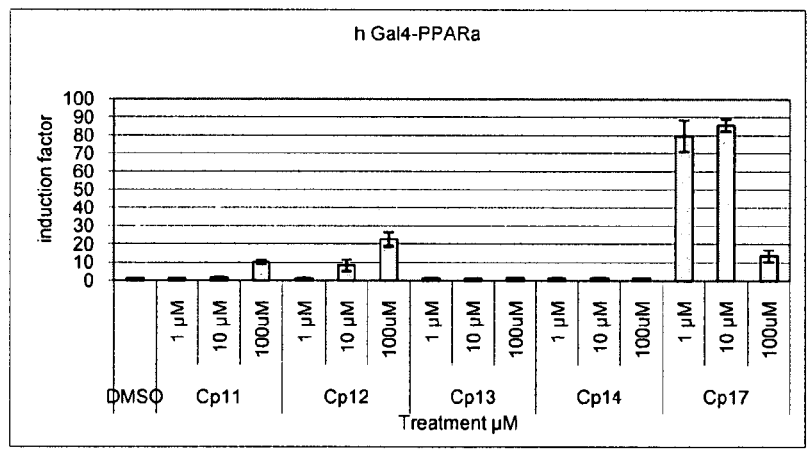
Figure : 2-2
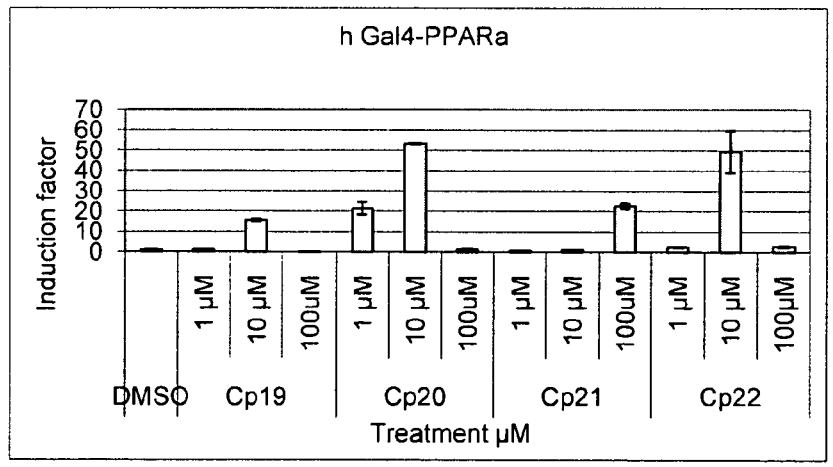
Figure : 2-3

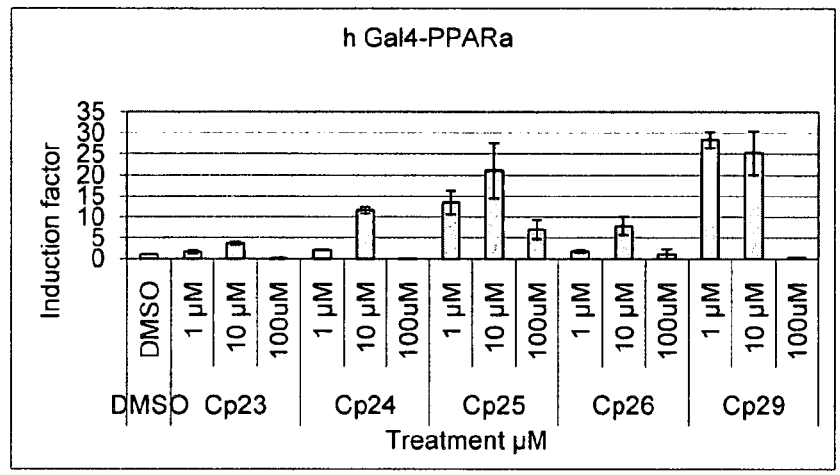
Figure : 2-4
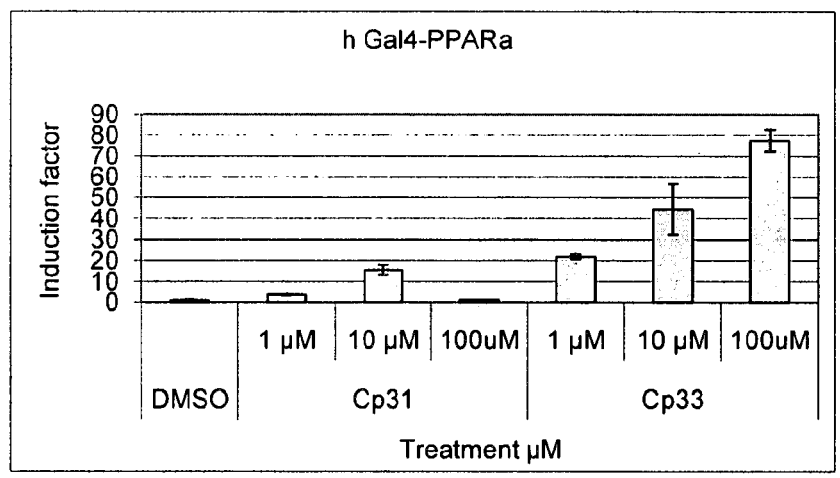
Figure : 2-5
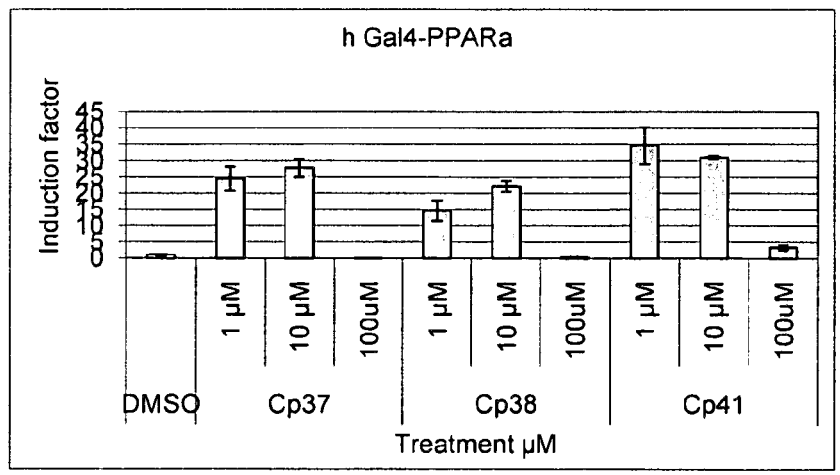
Figure 2-6

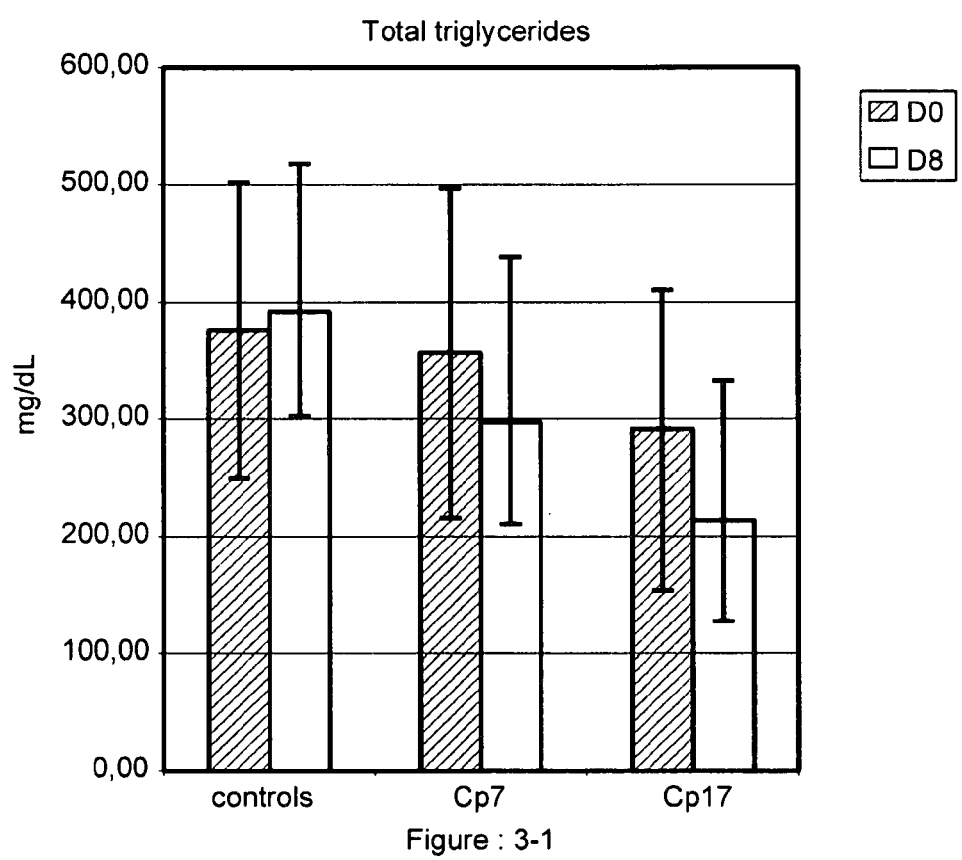
Figure : 3-1

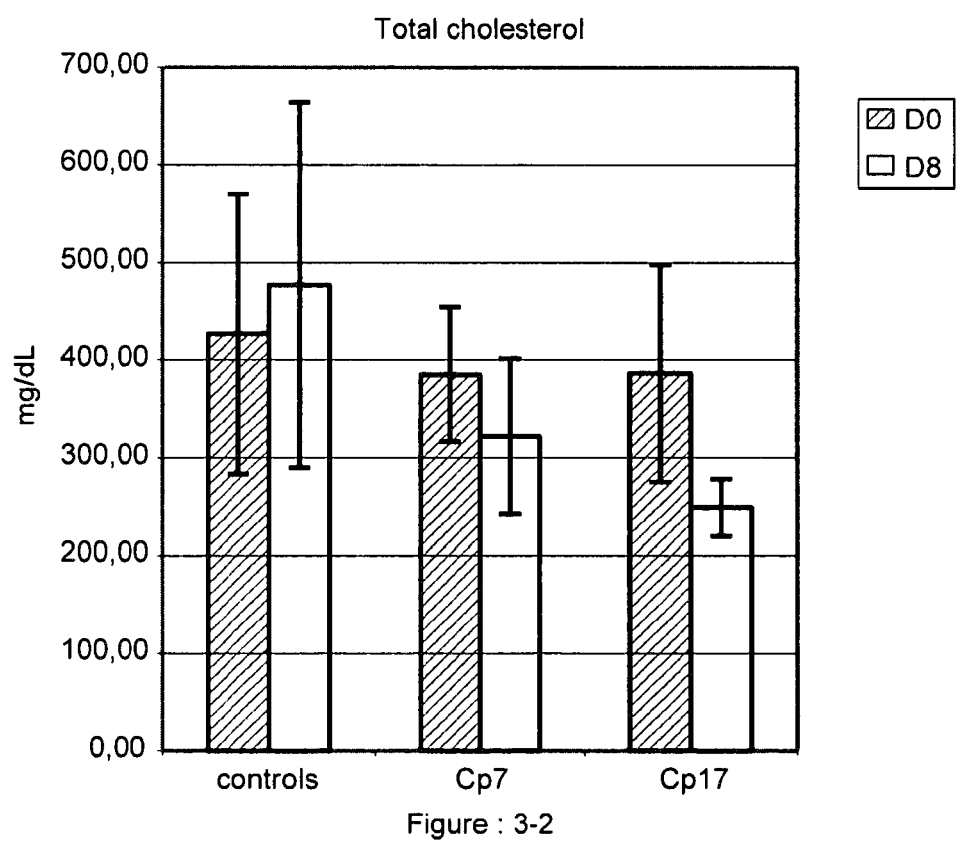
Figure: 3-2

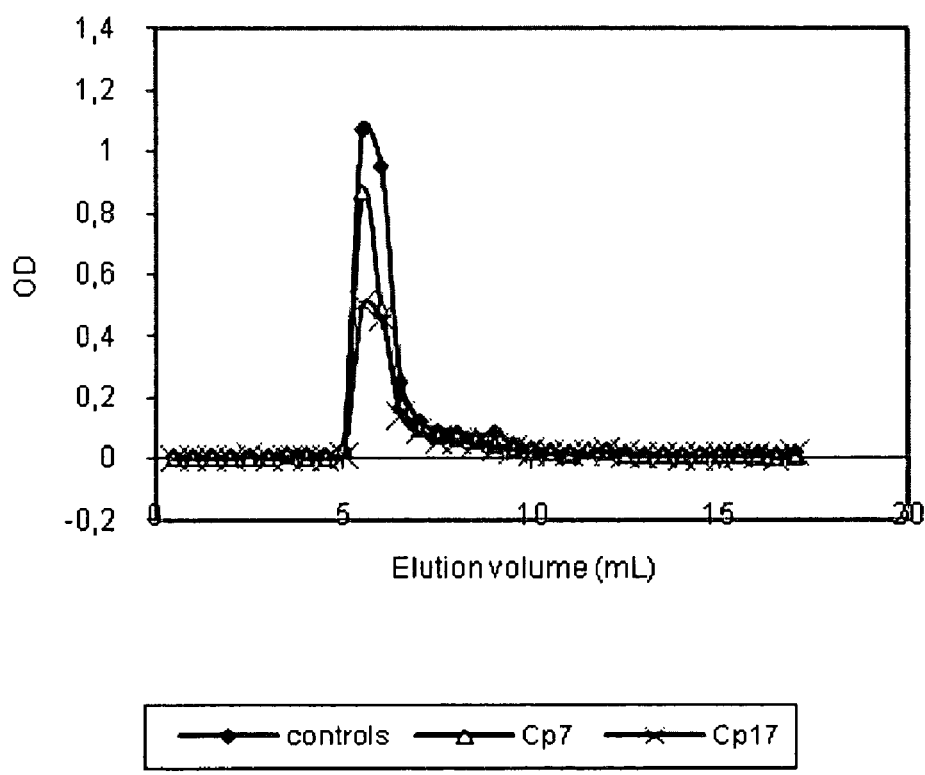
Figure : 3-3

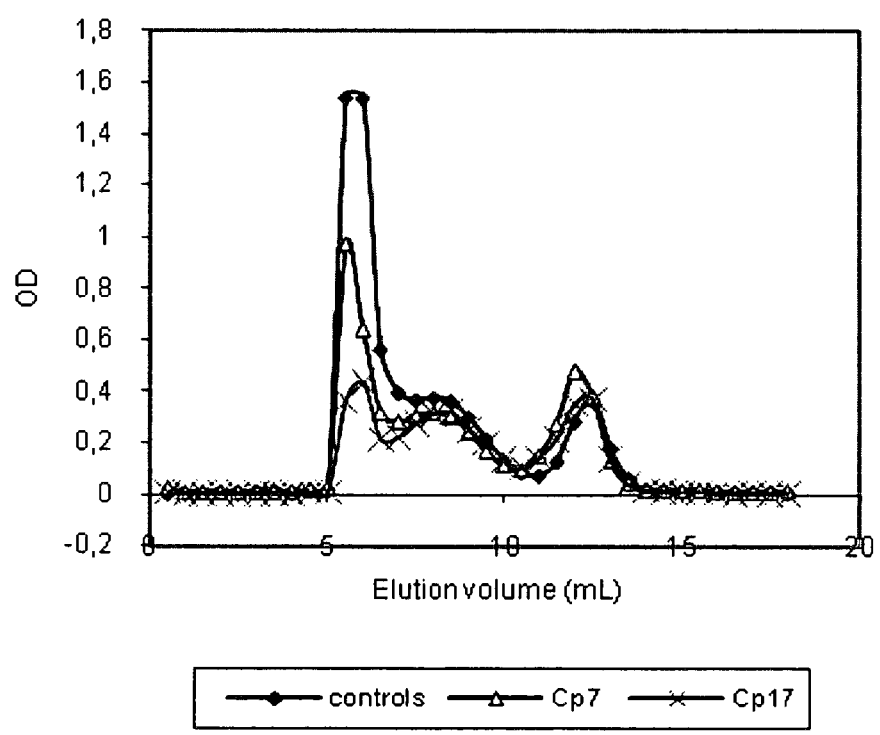
Figure : 3-4

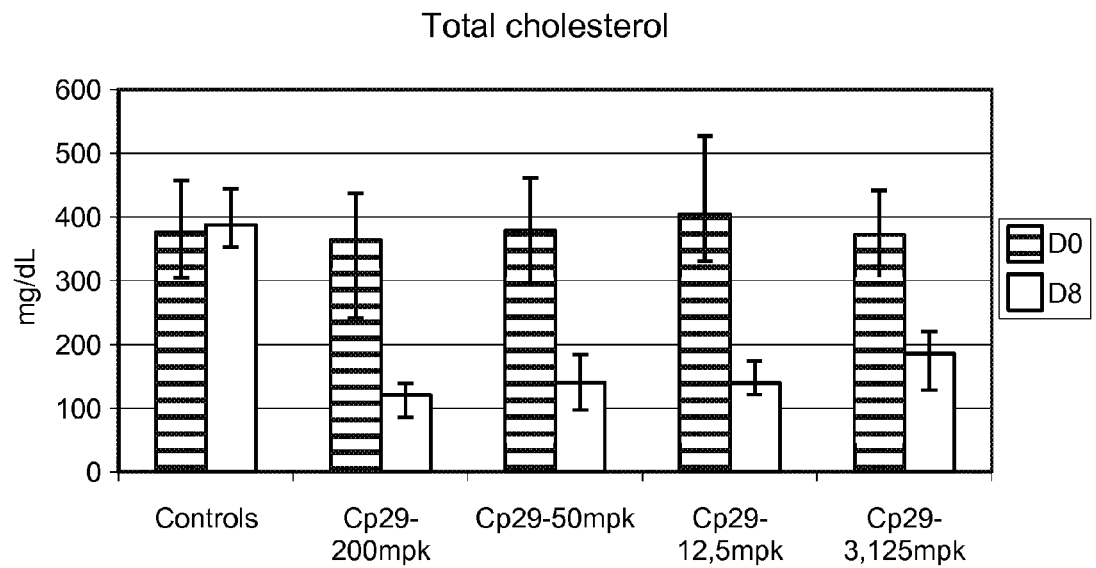
Figure : 3-5
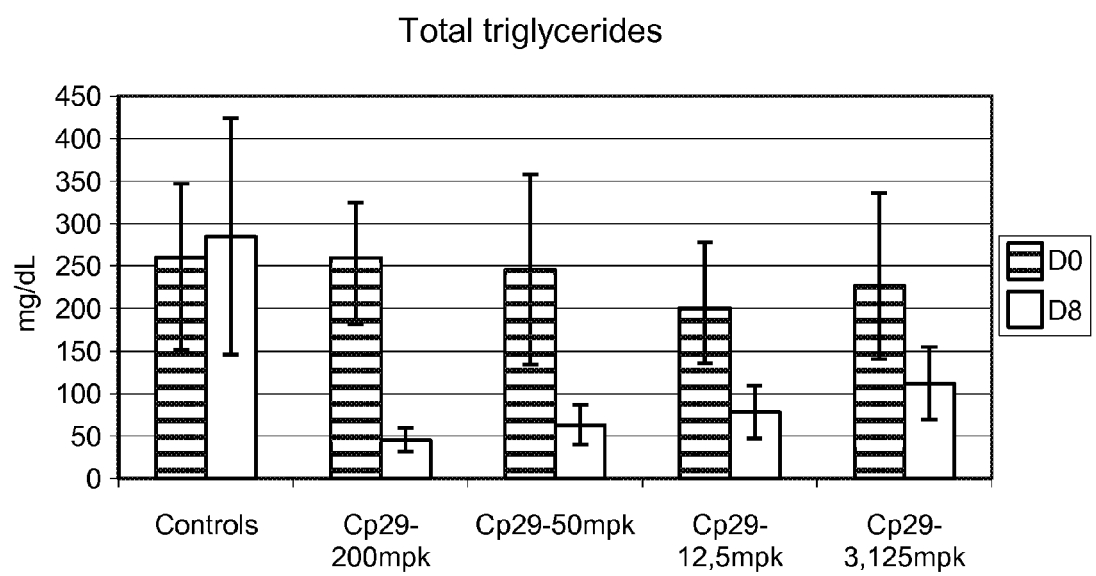
Figure : 3-6

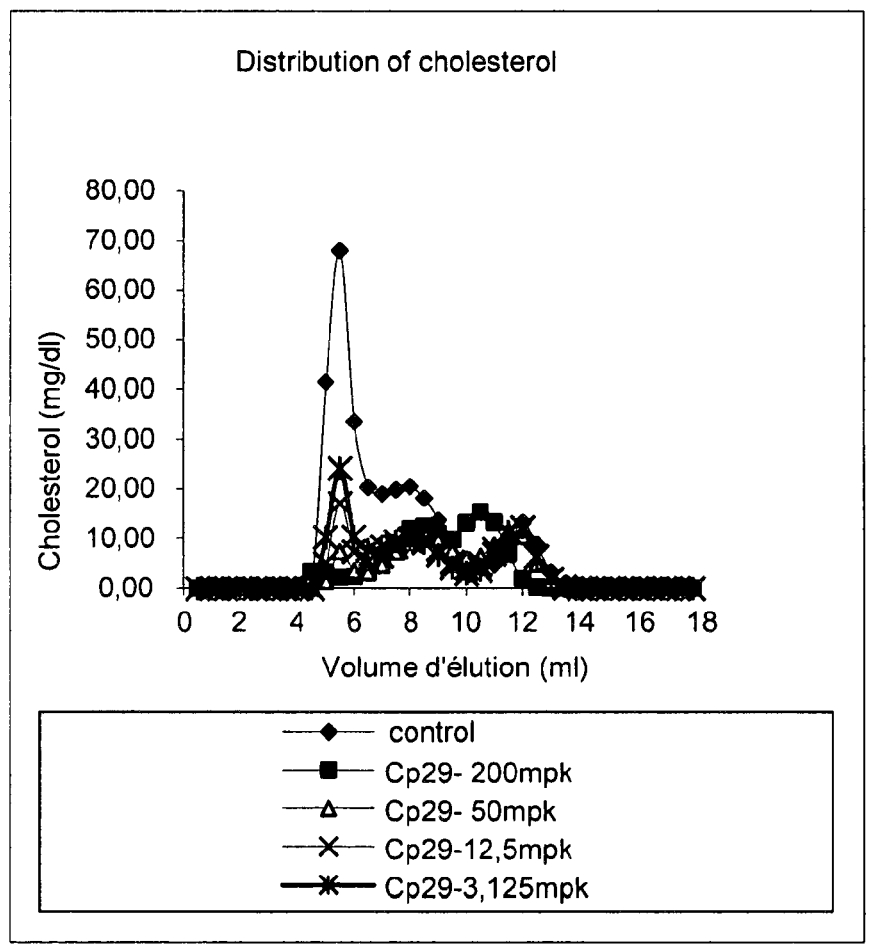
Figure : 3-7

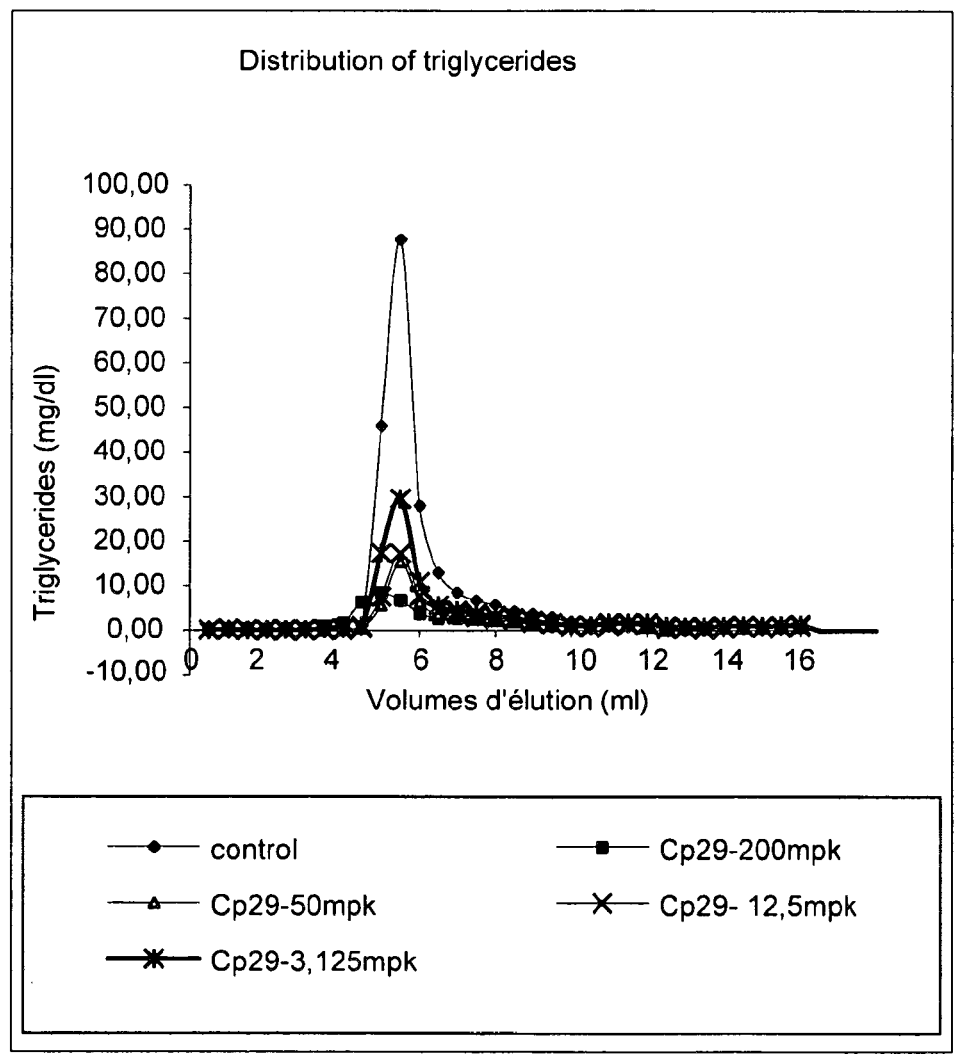
Figure :3-8

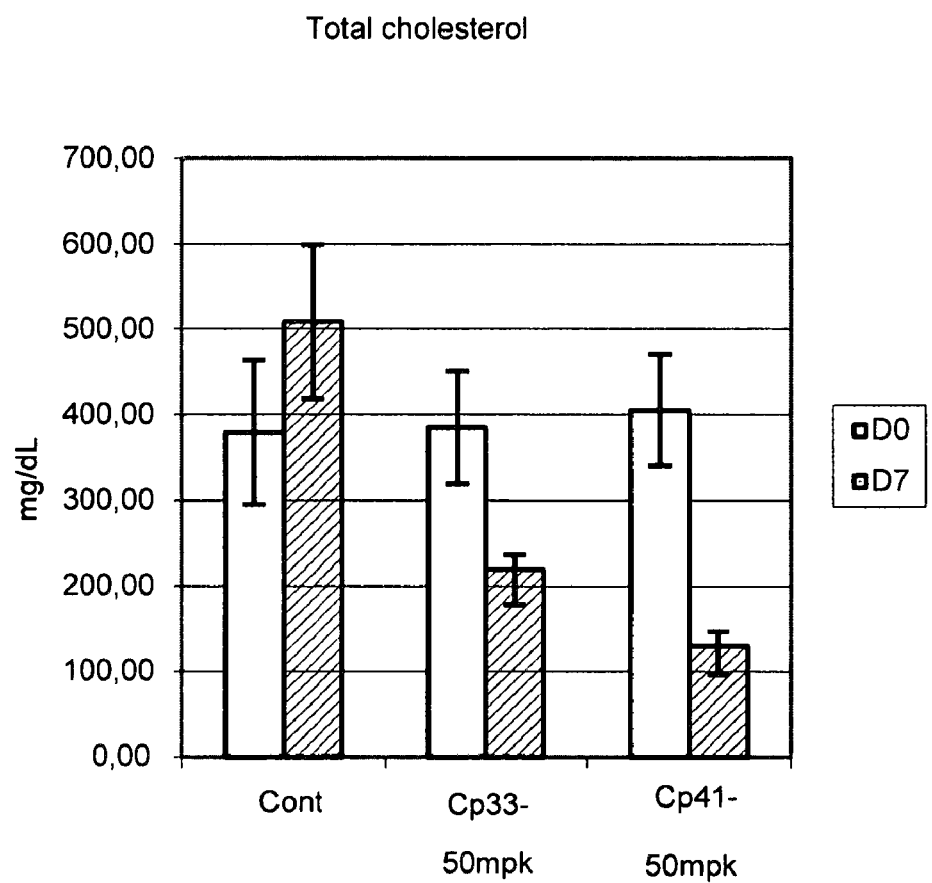
Figure :3-9

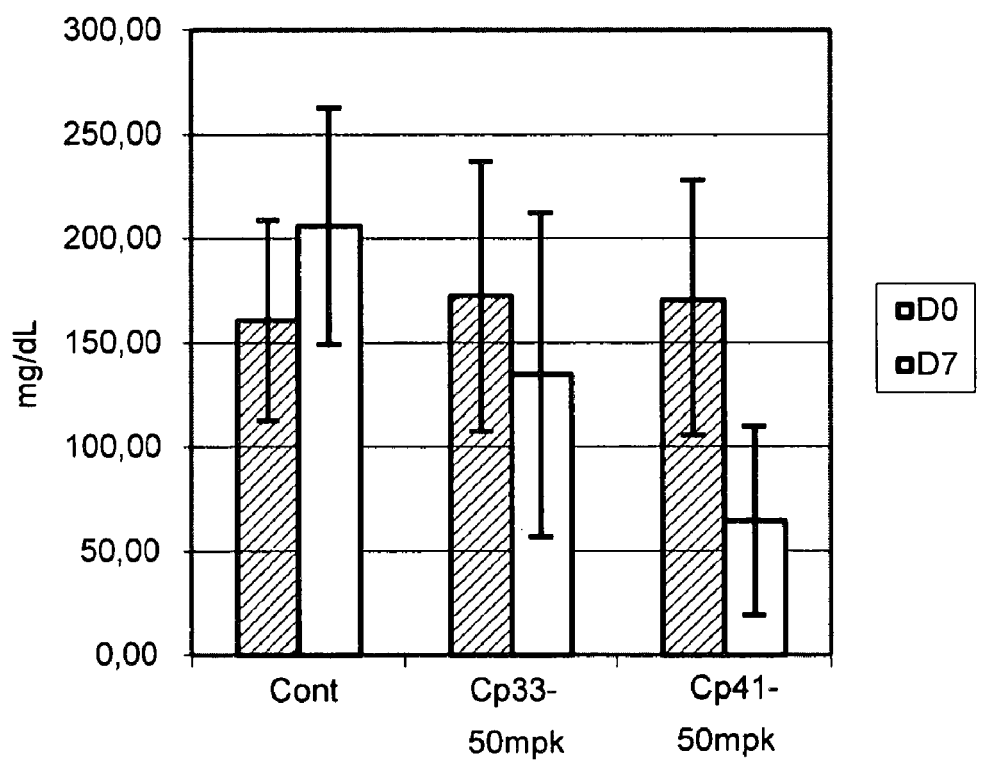
Figure: 3-10

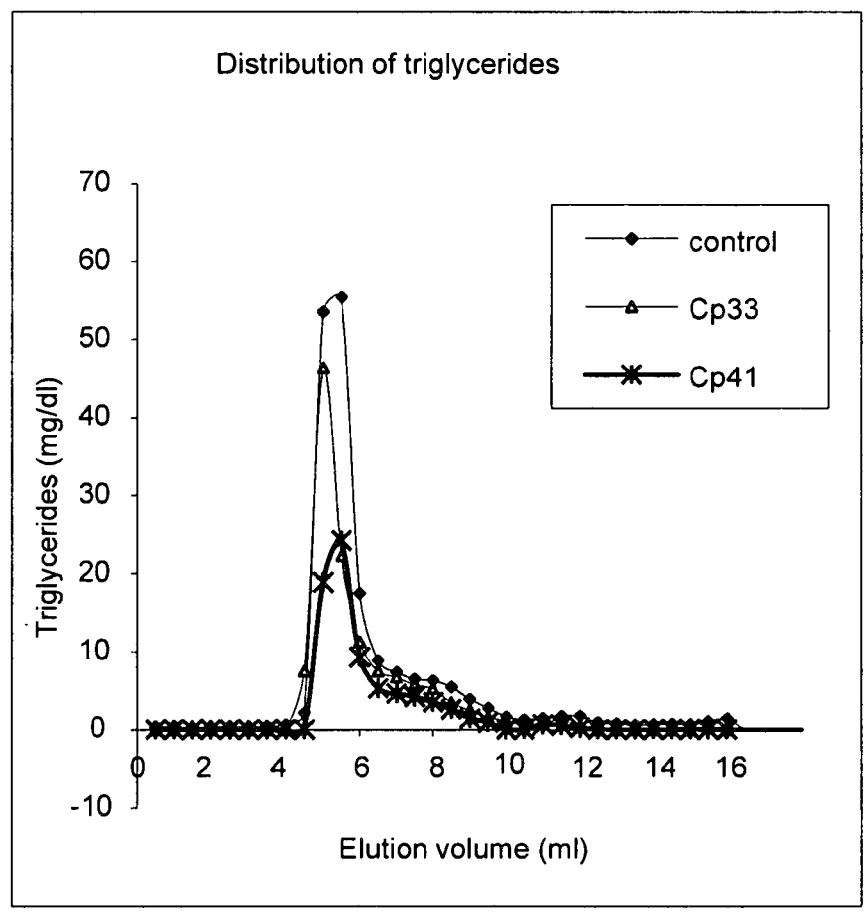
Figure : 3-11

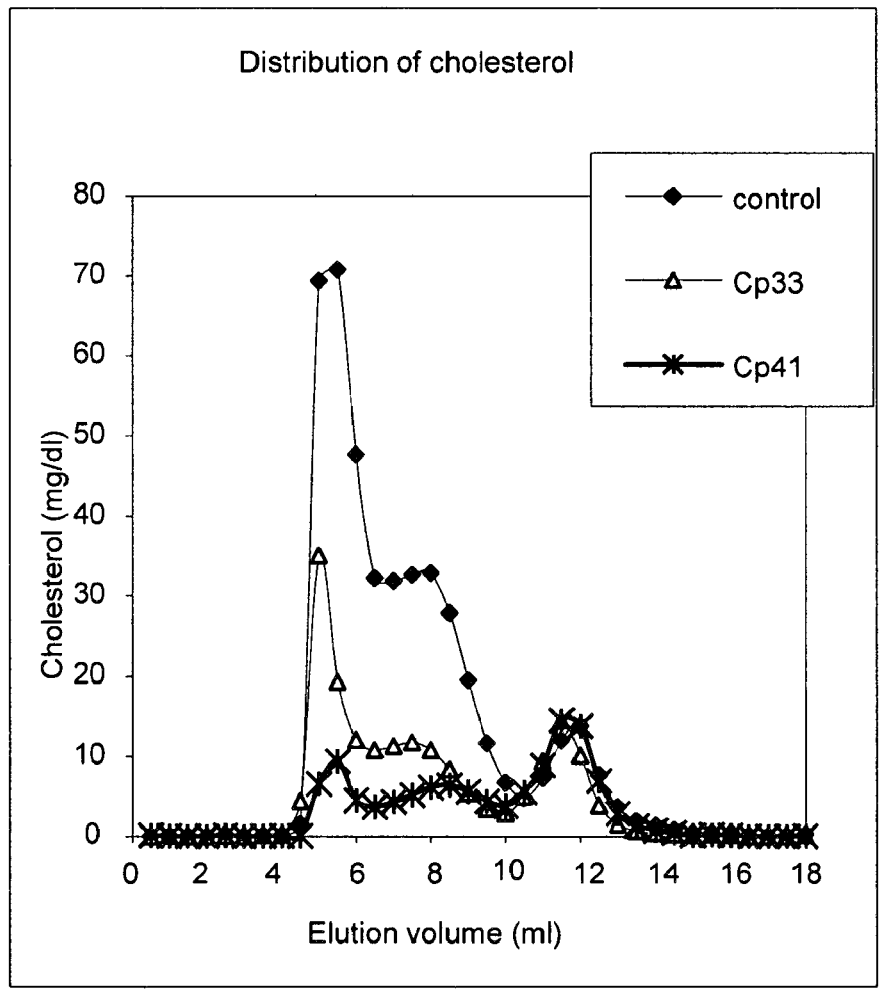
Figure : 3-12

COMPOSITION BASED ON SUBSTITUTED 1,3-DIPHENYLPROP-2-EN-1-ONE DERIVATIVES, PREPARATION AND USES THEREOF

This application is a continuation of application Ser. No. 10/520,078 (issued as U.S. Pat. No. 7,632,870), filed Apr. 4, 2005 (published as US-2005-0171149-A1 on Aug. 4, 2005), which is a U.S. national phase of International Application PCT/FR2003/002128, filed Jul. 8, 2003, which designated the U.S. and claims benefit of FR 02/08570, filed Jul. 8, 2002, the entire contents of each of which is incorporated herein by reference.

The invention concerns compositions comprising substituted 1,3-diphenylprop-2-en-1-one derivatives and uses thereof, particularly in the fields of human and veterinary health. The compounds according to the invention have pharmacological antioxidant properties and PPARα and PPARγ activator properties which are advantageous. The invention more specifically describes the different uses of said compounds and the pharmaceutical and cosmetic compositions comprising same. The compounds according to the invention are useful in particular for preventing or treating cardiovascular diseases, syndrome X, restenosis, diabetes, obesity, hypertension, inflammatory diseases, cancers or neoplasms (benign or malignant tumors), neurodegenerative, dermatological diseases and disorders related to oxidative stress, for preventing or treating the effects of ageing in general and for example skin ageing, in particular in the field of cosmetics (development of wrinkles and the like).

The derivatives and/or compositions of the invention can be used in particular for treating diseases implicating tissues that express PPARα and PPARγ. More particularly, they advantageously allow to treat inflammatory, proliferative, degenerative diseases or pathologies affecting different organs and tissues, in particular diseases involving pathological angiogenesis or neovascularization as well as any pathology or disorder (for example related to age) involving an oxidative stress. In an advantageous manner, the compounds of the invention can be used in the treatment of diseases or disorders affecting tissues and/or organs, irrespective of the etiological component.

The PPARs, or "peroxisome proliferator activated receptors", are nuclear receptors from the superfamily of transcription factors activated by the following ligands: steroids/thyroid hormones/retinoids. To date, three PPAR isotypes have been cloned in mice and humans: PPARα, PPARβ/δ and PPARγ. While PPARβ/δ expression in humans appears to be ubiquitous, PPARα and γ exhibit a differential tissue distribution (Braissant and Wahli 1998). PPARα is expressed in cells with high fatty acid catabolic activity and in cells with high peroxisomal activity (hepatocytes, cardiomyocytes, renal proximal tubules, intestinal mucosa). PPARβ/δ is expressed ubiquitously and abundantly in most tissues. As far as PPARγ expression is concerned, it is limited mainly to adipose tissue, certain immune system cells and retina and is present in only trace amounts in other organs (Braissant and Wahli 1998).

The PPARs contain several domains having different properties. A DNA binding domain (DBD) recognizes specific sequences, also called response elements, located in regulatory regions of their target genes. Like other nuclear receptors, the PPARs also contain a ligand binding domain, the activation of PPARs by their ligand modulating the expression of genes which contain specific PPAR response elements (PPRE) in the promoter region. To activate transcription of their target genes, the activated PPARs must heterodimerize with another nuclear receptor, RXR (Retinoid-X-Receptor). Taking the example of PPARα, its action is mediated by a class of compounds such as the fibrates which have a lipid-lowering effect. Natural ligands have also been identified such as for example fatty acids, eicosanoids (leukotriene $B_4$) and 8(S)-hydroxyeicosatetraenoic acid (Kliewer, Sundseth et al. 1997).

The PPARs have been associated primarily with lipid and glucose metabolism. PPAR activators, such as fibrates, enable a regulation of plasma cholesterol and triglyceride concentrations via activation of PPARα (Hourton, Delerive et al. 2001). Fibrate therapy leads to an increase in fatty acid oxidation in liver. Fibrates also decrease the synthesis and expression of triglycerides (Staels and Auwerx 1998). PPARα activators are also capable of correcting hyperglycemia and insulin level. Fibrates also reduce adipose tissue mass through a mechanism which is independent of food intake and leptin gene expression (Guerre-Millo, Gervois et al. 2000).

The therapeutic interest of PPARγ agonists has been widely investigated in the treatment of type 2 diabetes (Spiegelman 1998). It has been shown that PPARγ agonists restore insulin sensitivity in target tissues and reduce plasma glucose, lipid and insulin levels both in animal models of type 2 diabetes and in humans (Ram V J 2003).

PPAR activation by ligands also plays a role in regulating the expression of genes that participate in processes such as inflammation, angiogenesis, cell proliferation and differentiation, apoptosis and the activities of iNOS, MMPase and TIMPs. Activation of PPARα in keratinocytes results in a cessation of their proliferation and expression of genes involved in differentiation (Komuves, Hanley et al. 2000). The PPARs have anti-inflammatory properties because they negatively interfere with transcription mechanisms involving other transcription factors like NF-κB or transcriptional activators like (STAT) and AP-1 (Desvergne and Wahli 1999). Said anti-inflammatory and anti-proliferative properties make the PPARS (and particularly PPARα) interesting therapeutic targets for the treatment of diseases such as vascular occlusive diseases (atherosclerosis, etc.), hypertension, diseases related to neovascularization (diabetic retinopathy, etc.), inflammatory diseases (inflammatory bowel disease, psoriasis, etc.) and neoplastic diseases (carcinogenesis, etc.).

Free radicals play a role in a very large range of pathologies including allergy, tumor initiation and promotion, cardiovascular diseases (atherosclerosis, ischemia), genetic and metabolic disorders (diabetes), infectious and degenerative diseases (Alzheimer's disease, Parkinson's disease, Prion, etc.) and ophthalmic disorders (Mates, Perez-Gomez et al. 1999).

Reactive oxygen species (ROS) are produced during normal cell functioning. ROS comprise the hydroxyl radicals (OH), superoxide anion ($O_2^-$), hydrogen peroxide ($H_2O_2$) and nitric oxide (NO). Said species are very labile and, due to their high chemical reactivity, constitute a danger to the biological functions of cells. They induce lipid peroxidation, oxidation of certain enzymes and very extensive oxidation of proteins leading to degradation thereof. Protection against lipid peroxidation is an essential process in aerobic organisms, because peroxidation products can cause DNA damage. Thus a deregulation or modification of the equilibrium between the production, processing and elimination of radical species by natural antioxidant defenses leads to the establishment of processes that are deleterious to the cell or organism.

ROS are processed via an antioxidant system that comprises an enzymatic component and a non-enzymatic component.

The enzymatic system is composed of several enzymes which have the following characteristics:

Superoxide dismutase (SOD) destroys the superoxide radical by converting it to peroxide. The peroxide in turn is acted upon by another enzyme system. Low levels of SOD are continuously produced by aerobic respiration. Three classes of SOD have been identified in humans, each containing Cu, Zn, Fe, Mn, or Ni as cofactor. The three forms of human SOD are distributed as follows: a cytosolic Cu—Zn SOD, a mitochondrial Mn—SO and an extracellular SOD.

Catalase is very efficient at converting hydrogen peroxide ($H_2O_2$) to water and $O_2$. Hydrogen peroxide is enzymatically catabolized in aerobic organisms. Catalase also catalyzes the reduction of a variety of hydroperoxides (ROOH).

Glutathione peroxidase uses selenium as cofactor and catalyzes the reduction of hydroperoxides (ROOH and $H_2O_2$) by using glutathione, and thereby protects cells against oxidative damage.

Non-enzymatic antioxidant defenses comprise molecules that are synthesized or supplied in the diet.

Antioxidant molecules are present in different cell compartments. Detoxification enzymes for example eliminate free radicals and are essential to cell life. The three most important types of antioxidant compounds are the carotenoids, vitamin C and vitamin E (Gilgun-Sherki, Melamed et al. 2001).

The inventors have shown that, in a surprising manner, the compounds of the invention have PPARα agonist activity and antioxidant properties. The inventive compounds are therefore capable of interfering with at least two signalling pathways which are activated in particular in inflammation: cytokine production and free radical production. By acting synergistically, the compounds of the invention constitute an advantageous therapeutic means for treating pathologies related to inflammation (atherosclerosis, allergy, asthma, eczema, pruritus, etc.), neurodegeneration (Alzheimer's disease, Parkinson's disease, etc.), deregulations of lipid and/or glucose metabolism (diabetes, atherosclerosis, obesity, etc.), cell proliferation/differentiation (carcinogenesis, etc.) and disorders related to ageing (skin or central nervous system, etc.).

The inventors have shown that the compounds according to the invention concurrently have PPAR activator, antioxidant and anti-inflammatory properties.

Thus, the invention concerns pharmaceutical compositions comprising at least one substituted 1,3-diphenylprop-2-en-1-one derivative for the treatment of pathologies related to inflammation, neurodegeneration, deregulations of lipid and/or glucose metabolism, cell proliferation and/or differentiation and/or skin or central nervous system ageing.

In particular, then, the invention has as its object a composition comprising, in a pharmaceutically acceptable support, at least one substituted 1,3-diphenylprop-2-en-1-one derivative represented by formula (I) below:

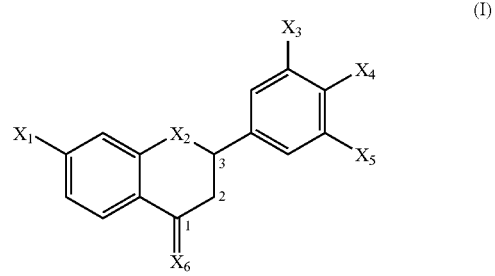

in which:
$X_1$ represents a halogen or a —R1 group or a group corresponding to the following formula: -G1-R1,
$X_2$ represents a hydrogen atom or a thionitroso group or a hydroxy group or an unsubstituted alkyloxy group or an alkylcarbonyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran-4-one (this option is depicted in formula (I) by dotted lines),
$X_3$ represents a —R3 group or a group corresponding to the following formula: -G3-R3,
$X_4$ represents a halogen or a thionitroso group or a —R4 group or a group corresponding to the following formula: -G4-R4,
$X_5$ represents a —R5 group or a group corresponding to the following formula: -G5-R5,
$X_6$ is an oxygen atom or a nitrogen atom, in the case where X6 is a nitrogen atom, it carries a hydrogen atom or a hydroxy group or an alkyloxy group,
R1, R3, R4, R5, which are the same or different, represent a hydrogen atom or an alkyl group substituted or not by at least one substituent which is part of group 1 or group 2 defined hereinbelow,
G1, G3, G4, G5, which are the same or different, represent an oxygen or sulfur atom,
with at least one of the groups X1, X3, X4 or X5 corresponding to the formula -G-R, and
with at least one of the groups R1, R3, R4 or R5 present in the form of an alkyl group containing at least one substituent from group 1 or group 2, said alkyl group being bound directly to the ring or being associated with a group G according to the formula -GR,
the substituents from group 1 are selected in the group consisting of carboxy groups having the formula: —$COOR_6$ and carbamoyl groups having the formula: —$CONR_6R_7$,
the substituents from group 2 are selected in the group consisting of sulfonic acid (—$SO_3H$) and sulfonamide groups having the formula: —$SO_2NR_6R_7$
with $R_6$ and $R_7$, which are the same or different, representing a hydrogen atom or an alkyl group possibly substituted by at least one group of type 1 or 2,
the optical and geometrical isomers, racemates, tautomers, salts, hydrates and mixtures thereof,
with the exception of compounds represented by formula (I) in which:
$X_1$, $X_2$, $X_3$ and $X_5$ each represent a hydrogen atom, $X_6$ represents an oxygen atom and $X_4$ represents a group corresponding to the formula —O—CR$_8$R$_9$—COOR$_{10}$, where R$_8$ and R$_9$, which are the same or different, represent a C1 to C2 alkyl group (comprising one or two carbon atoms), and R$_{10}$ represents a hydrogen atom or a C1 to C7 alkyl group, X$_2$, X$_3$ and X$_5$ each represent a hydrogen atom, X$_1$ represents a halogen atom or a R1 or -G1R1 group, where R1 represents an unsubstituted C1 to C2 alkyl group and G1 represents an oxygen atom, X$_6$ represents an oxygen atom and X$_4$ represents a group corresponding to the formula —O—CR$_{11}$R$_{12}$—COOR$_{10}$, where R$_{11}$ and R$_{12}$, which are the same or different, represent a hydrogen atom or a C1 to C2 alkyl group, and R$_{10}$ represents a hydrogen atom or a C1 to C7 alkyl group (comprising one to seven carbon atoms), and X2 represents a hydrogen atom and X, represents -G1R1 where G1 represents an oxygen atom and R1 represents CH2COOH.

Said composition can be used in particular for the treatment or prophylaxis of a pathology related to inflammation, neurodegeneration, deregulations of lipid and/or glucose metabolism, cell proliferation and/or differentiation and/or skin or central nervous system ageing.

The invention also encompasses a composition comprising the prodrugs of compounds represented by formula (I) which, after administration to a subject, are converted to compounds represented by formula (I) and/or metabolites of compounds represented by formula (I) which display similar therapeutic activity to compounds represented by formula (I), possibly in association with another therapeutic agent, for the treatment or prophylaxis of a pathology related to inflammation, neurodegeneration, deregulations of lipid and/or glucose metabolism, cell proliferation and/or differentiation and/or skin or central nervous system ageing.

In the scope of the invention, the derivatives represented by formula (I) such as defined hereinabove can adopt a cis or trans conformation. An composition according to the invention can thus comprise derivatives corresponding to the cis or trans conformation or a mixture thereof.

Advantageously, none of the groups X3, X4 and X5 represents a hydrogen atom. Compounds with formula (I) which meet this definition constitute compounds of general formula (II).

Advantageously, one or two of the groups X3, X4 and X5 represent a hydrogen atom and X1 is an unsubstituted alkyl group. Compounds with formula (I) which meet this definition constitute compounds of general formula (III).

Advantageously, one or two of the groups X3, X4 and X5 represent a hydrogen atom and X2 is a thionitroso group or an alkylcarbonyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran-4-one (this option is depicted in formula (I) by dotted lines). Compounds with formula (I) which meet this definition constitute compounds of general formula (IV).

Advantageously, one or two of the groups X3, X4 and X5 represent a hydrogen atom and at least one of the groups X1, X2, X3, X4 or X5 is the GR form in which G is a sulfur atom. Compounds with formula (I) which meet this definition constitute compounds of general formula (V).

Advantageously, one or two of the groups X3, X4 and X5 represent a hydrogen atom and at least one of the groups X1, X3, X4 or X5 is the -G-R form in which G is an oxygen atom and R is an alkyl group substituted by a substituent from group 1 where R6 is not a hydrogen atom. Compounds with formula (I) which meet this definition constitute compounds of general formula (VI).

Advantageously, one or two of the groups X3, X4 and X5 represent a hydrogen atom and at least one of the groups X1, X3, X4 or X5 is the GR form in which G is an oxygen atom and R is an alkyl group substituted by a sulfonamide such as defined hereinabove. Compounds with formula (I) which meet this definition constitute compounds of general formula (VII).

Advantageously, X4 is a thionitroso group or a R4 group or a group corresponding to the formula -G4-R4. Derivatives having formula (I) in which X4 meets this definition constitute derivatives represented by general formula (VIII) in which G4 and R4 are such as defined hereinabove.

Advantageously, X2 is a thionitroso group or a hydroxy group or an alkyloxy group or a thiol group or an alkylthio group. Derivatives having formula (I) in which X2 meets this definition constitute derivatives represented by general formula (IX).

Other advantageous derivatives represented by formula (I) of the invention have a general formula (X) such that X4 is a thionitroso group or a —R4 group or a group corresponding to the formula -G4-R4 and X2 is a thionitroso group or a hydroxy group or an alkyloxy group or a thiol group or an alkylthio group, G4 and R4 being such as defined hereinabove.

Other advantageous derivatives represented by formula (I) of the invention have a general formula (XI) such that X1 represents a —R1 group or a group corresponding to the formula -G1-R1, with R1 being an alkyl group substituted by a substituent which is part of group 1 and G1 and the substituent from group 1 being such as defined hereinabove.

More preferably, another object of the invention concerns derivatives represented by formula (XI) such as described hereinabove, characterized in that X1 is a -G1-R1 group.

Even more preferably, another object of the invention concerns derivatives represented by formula (XI) such as described hereinabove, characterized in that X1 is a -G1-R1 group in which G1 is an oxygen atom.

Other advantageous derivatives represented by formula (I) of the invention have a general formula (XII) such that X1 represents a —R1 group or a group corresponding to the formula -G1-R1, with R1 being an alkyl group substituted by a substituent which is part of group 2 and G1 and the substituent from group 2 being such as defined hereinabove.

Other advantageous derivatives represented by formula (I) of the invention have a general formula (XIII) such that X3 represents a —R3 group or a group corresponding to the formula -G3-R3, with R3 being an alkyl group substituted by a substituent which is part of group 1 and G3 and the substituent from group 1 being such as defined hereinabove.

Other advantageous derivatives represented by formula (I) of the invention have a general formula (XIV) such that X3 represents a —R3 group or a group corresponding to the formula -G3-R3, with R3 being an alkyl group substituted by a substituent which is part of group 2 and G3 and the substituent from group 2 being such as defined hereinabove.

Other advantageous derivatives represented by formula (I) of the invention have a general formula (XV) such that X4 represents a —R4 group or a group corresponding to the formula G4-R4, with R4 being an alkyl group substituted by a substituent which is part of group 1 and G4 and the substituent from group 1 being such as defined hereinabove.

More preferably, another object of the invention concerns derivatives represented by formula (XV) such as described hereinabove, characterized in that X4 is a -G4-R4 group.

Even more preferably, another object of the invention concerns derivatives represented by formula (XV) such as described hereinabove, characterized in that X4 is a -G4-R4 group in which G4 is an oxygen atom.

Even more preferably, another object of the invention concerns derivatives represented by formula (XV) such as described hereinabove, characterized in that X4 is a -G4-R4 group in which G4 is an oxygen atom, and X3 or X5 respectively represent R3 or G3R3, on the one hand, and R5 or G5R5, on the other hand, with R3 or R5 being alkyl groups carrying a substitutent from group 1, said substituent from group 1 being such as defined hereinabove.

Other advantageous derivatives represented by formula (I) of the invention have a general formula (XVI) such that X4 represents a —R4 group or a group corresponding to the formula -G4-R4 with R4 being an alkyl group substituted by a substituent which is part of group 2 and G4 the substituent from group 2 being such as defined hereinabove.

Other advantageous derivatives represented by formula (I) of the invention have a general formula (XVII) such that X1 represents a halogen.

Other advantageous derivatives represented by formula (I) of the invention have a general formula (XVIII) such that X1 represents a —R1 group with R1 being a C1 to C4 alkyl group substituted or not by at least one substituent which is part of group 1 or group 2 defined hereinabove.

Other advantageous derivatives represented by formula (I) of the invention have a general formula (XIX) such that X1 represents a -G1R1 group with R1 being a C1 to C3 alkyl group substituted or not by at least one substituent which is part of group 1 or group 2 defined hereinabove.

Other advantageous derivatives represented by formula (I) of the invention have a general formula (XX) such that X1 represents a —R1 group with R1 being a C5 to C24 alkyl group substituted or not by at least one substituent which is part of group 1 or group 2 defined hereinabove.

Other advantageous derivatives represented by formula (I) of the invention have a general formula (XXI) such that X1 represents a -G1R1 group with R1 being a C4 to C24 alkyl group substituted or not by at least one substituent which is part of group 1 or group 2 defined hereinabove.

Another object of the invention concerns derivatives represented by formula (I) in which X1, X3, X4 or X5 represent OC(CH3)2COOR6 with R6 being such as defined hereinabove.

Another object of the invention concerns derivatives represented by formula (I) in which X1, X3, X4 or X5 represent SC(CH3)2COOR6 with R6 being such as defined hereinabove.

According to the invention, the term "alkyl" designates a saturated hydrocarbon function, linear, branched or cyclic, halogenated or not, having more particularly from 1 to 24, preferably 1 to 10, carbon atoms such as methyl, ethyl, propyl, isopropyl, butyl, isobutyl, tert-butyl, pentyl, neopentyl, n-hexyl. Groups containing one or two carbon atoms or containing from two to seven carbon atoms are particularly preferred. Methyl and ethyl groups are more particularly preferred.

The term thionitroso refers to a nitroso group bound to the aromatic ring through a sulfur atom.

The term halogen represents a chlorine atom or a bromine atom or an iodine atom or a fluorine atom.

The term alkyloxy designates an alkyl chain bound to the ring by an oxygen atom. The alkyl chain is defined earlier.

The term alkylthio refers to an alkyl chain bound to the aromatic ring by a sulfur atom (thioether bond). The alkyl chain is defined earlier.

According to a particular embodiment of the invention, preferred compounds are indicated below with their corresponding formulas:

1-[2-hydroxy-4-chlorophenyl]-3-[4-carboxydimethylmethyloxyphenyl]prop-2-en-1-one and 1-[2-hydroxy-4-chlorophenyl]-3-[4-isopropyloxycarbonyl dimethylmethyloxyphenyl]prop-2-en-1-one:

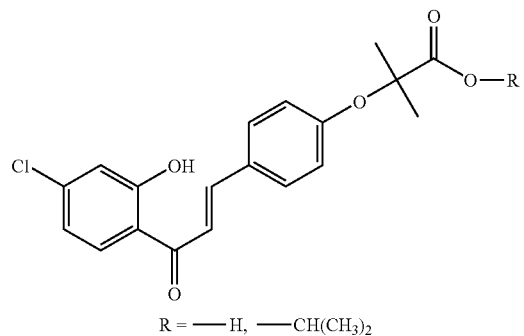

1-[2-hydroxyphenyl]-3-[4-carboxydimethylmethyloxyphenyl]prop-2-en-1-one and 1-[2-hydroxyphenyl]-3-[4-isopropyloxycarbonyldimethylmethyloxyphenyl]prop-2-en-1-one:

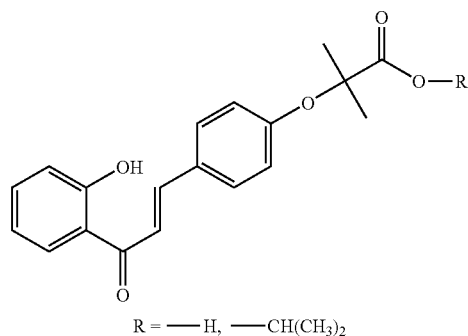

1-[2-methylcarbonyloxyphenyl]-3-[4-carboxydimethylmethyloxyphenyl]prop-2-en-1-one and 1-[2-methylcarbonyloxyphenyl]-3-[4-isopropyloxycarbonyldimethyl methyloxyphenyl]prop-2-en-1-one:

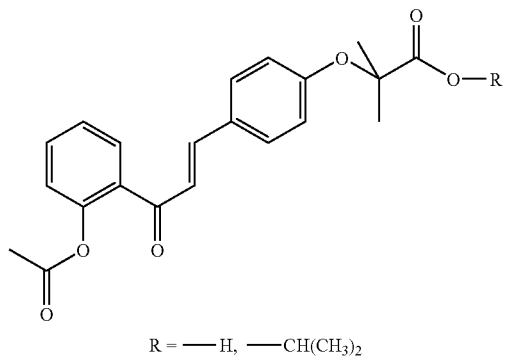

1-[2-hydroxyphenyl]-3-[4-carboxydimethylmethyloxyphenyl]-1-hydroxyimino prop-2-ene and 1-[2-hydroxyphenyl]-3-[4-isopropyloxycarbonyldimethylmethyloxyphenyl]-1-hydroxyiminoprop-2-ene:

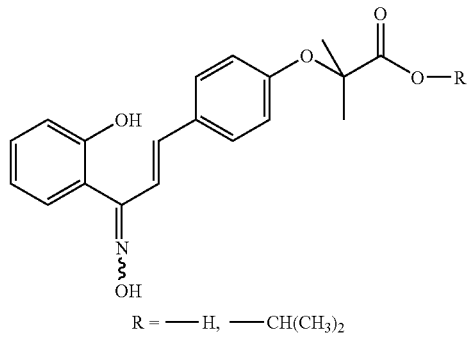

R = ——H, ——CH(CH₃)₂

1-[2-hydroxy-4-carboxydimethylmethyloxyphenyl]-3-[3,5-ditertbutyl-4-hydroxyphenyl]prop-2-en-1-one, 1-[2-hydroxy-4-ethyloxycarbonyl dimethylmethyloxyphenyl]-3-[3,5-ditertbutyl-4-hydroxyphenyl]prop-2-en-1-one and 1-[2-hydroxy-4-ethoxycarbonyldimethylmethyloxyphenyl]-3-[3,5-ditertbutyl-4-hydroxyphenyl]prop-2-en-1-one:

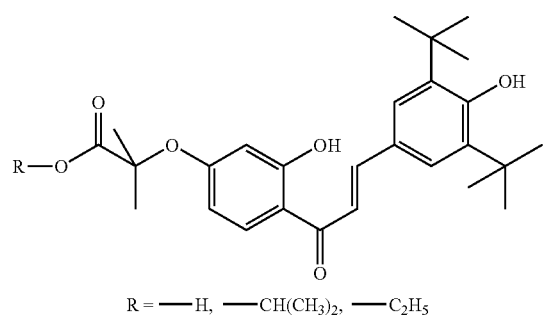

R = ——H, ——CH(CH₃)₂, ——C₂H₅

1-[2-hydroxyphenyl]-3-[3-carboxydimethylmethyloxy-4-hydroxy-5-tertbutylphenyl]prop-2-en-1-one and 1-[2-hydroxyphenyl]-3-[3-isopropyloxycarbonyldimethylmethyloxy-4-hydroxy-5-tertbutylphenyl]prop-2-en-1-one:

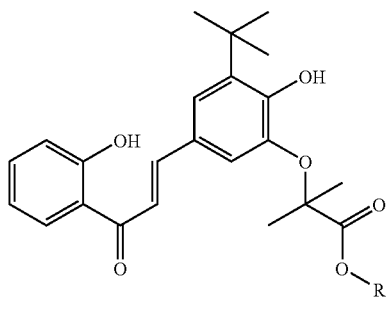

R = ——H, ——CH(CH₃)₂

1-[2-hydroxy-4-chlorophenyl]-3-[3-carboxydimethylmethyloxy-4-hydroxy-5-tertbutylphenyl]prop-2-en-1-one and 1-[2-hydroxy-4-chlorophenyl]-3-[3-isopropyloxycarbonyldimethylmethyloxy-4-hydroxy-5-tertbutylphenyl]prop-2-en-1-one:

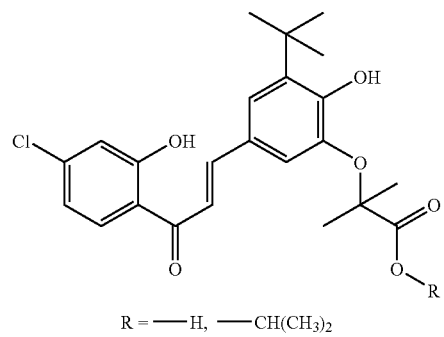

R = ——H, ——CH(CH₃)₂

1-[2-hydroxyphenyl]-3-[3-carboxydimethylmethyl-4-hydroxy-5-tertbutylphenyl]prop-2-en-1-one and 1-[2-hydroxyphenyl]-3-[3-isopropyloxycarbonyldimethylmethyl-4-hydroxy-5-tertbutylphenyl]prop-2-en-1-one (:

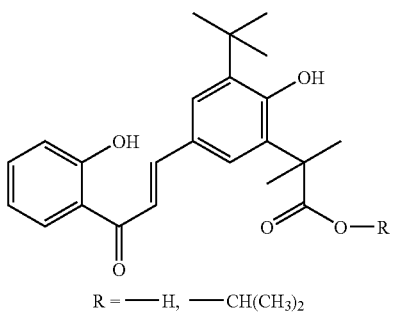

R = ——H, ——CH(CH₃)₂

1-[2-hydroxy-4-chlorophenyl]-3-[3-carboxydimethylmethyl-4-hydroxy-5-tertbutylphenyl]prop-2-en-1-one and 1-[2-hydroxy-4-chlorophenyl]-3-[3-isopropyloxycarbonyldimethylmethyl-4-hydroxy-5-tertbutylphenyl]prop-2-en-1-one:

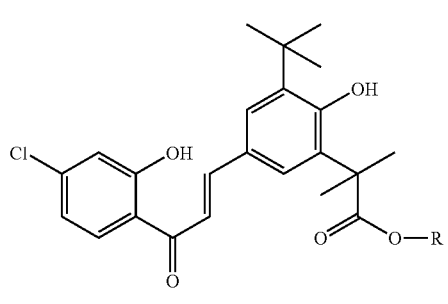

R = ——H, ——CH(CH₃)₂

1-[2-hydroxy-4-chlorophenyl]-3-[3,5-dimethoxy-4-carboxydimethylmethyloxyphenyl]prop-2-en-1-one and 1-[2-hydroxy-4-chlorophenyl]-3-[3,5-dimethoxy-4-isopropyloxycarbonyldimethylmethyloxy phenyl]prop-2-en-1-one:

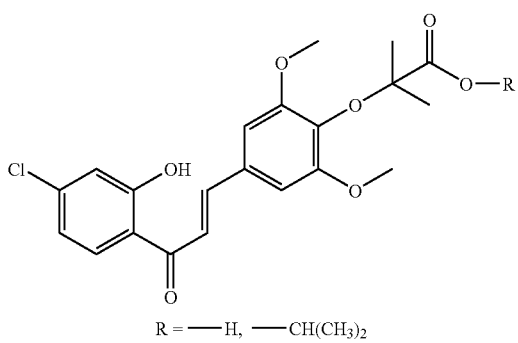

R = ——H, ——CH(CH₃)₂

1-[2-hydroxyphenyl]-3-[3,5-dimethoxy-4-carboxydimethylmethyloxyphenyl]prop-2-en-1-one and 1-[2-hydroxyphenyl]-3-[3,5-dimethoxy-4-isopropyloxycarbonyldimethylmethyloxyphenyl]prop-2-en-1-one:

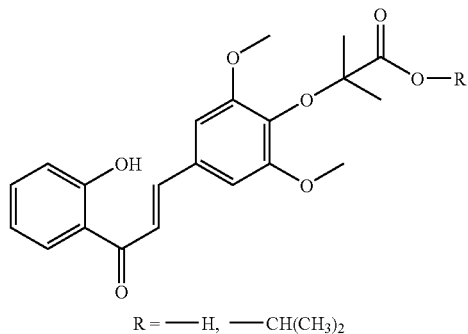

R = ——H, ——CH(CH₃)₂

1-[2-hydroxy-4-carboxydimethylmethyloxyphenyl]-3-[3,5-dimethoxy-4-hydroxyphenyl]prop-2-en-1-one and 1-[2-hydroxy-4-isopropyloxycarbonyldimethylmethyloxyphenyl]-3-[3,5-di-methoxy-4-hydroxyphenyl]prop-2-en-1-one:

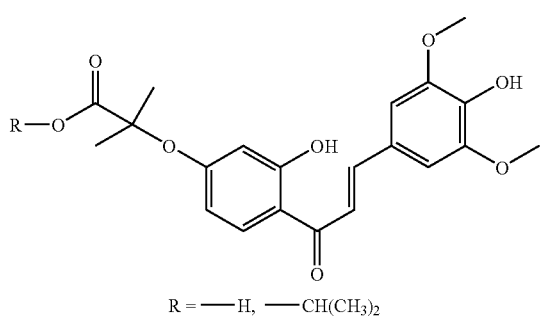

R = ——H, ——CH(CH₃)₂

1-[2-hydroxy-4-chlorophenyl]-3-[3,4-dihydroxy-5-carboxydimethylmethyloxyphenyl]prop-2-en-1-one and 1-[2-hydroxy-4-chlorophenyl]-3-[3,4-dihydroxy-5-isopropyloxycarbonyldimethylmethyloxyphenyl]-2-propen-1-one:

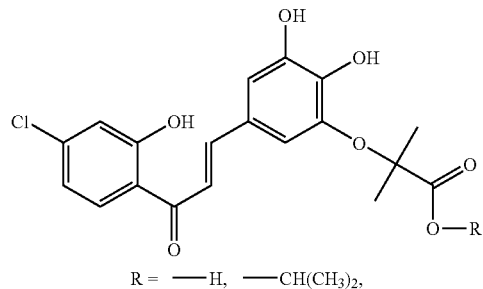

R = ——H, ——CH(CH₃)₂,

1-[2-hydroxy-4-carboxydimethylmethyloxyphenyl]-3-[3,5-dimethyl-4-hydroxyphenyl]prop-2-en-1-one and 1-[2-hydroxy-4-isopropyloxycarbonyl dimethylmethyloxyphenyl]-3-[3,5-dimethyl-4-hydroxyphenyl]prop-2-en-1-one:

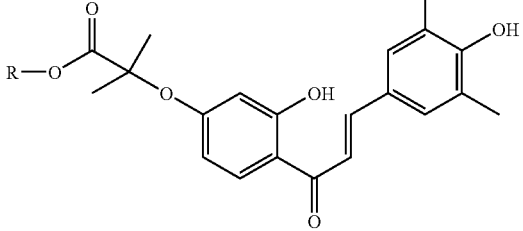

R = ——H, ——CH(CH₃)₂,

1-[2-hydroxy-4-chlorophenyl]-3-[3,5-dimethyl-4-carboxydimethylmethyloxyphenyl]prop-2-en-1-one and 1-[2-hydroxy-4-chlorophenyl]-3-[3,5-dimethyl-4-isopropyloxycarbonyldimethylmethyloxyphenyl]prop-2-en-1-one:

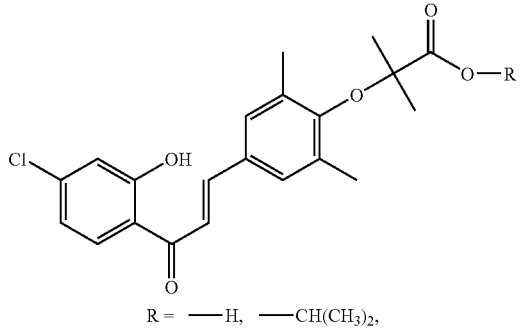

R = ——H, ——CH(CH₃)₂, and 1-[2-hydroxyphenyl]-3-[3,5-dimethyl-4-carboxydimethylmethyloxyphenyl]prop-2-en-1-one and 1-[2-hydroxyphenyl]-3-[3,5-dimethyl-4-isopropyloxycarbonyldimethylmethyloxyphenyl]prop-2-en-1-one:

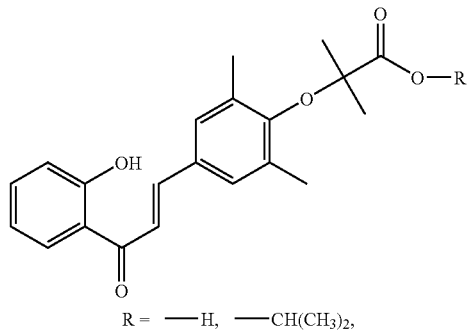

R = —H, —CH(CH₃)₂, and 1-[2-hydroxyphenyl]-3-[3-carboxydimethylmethyloxyphenyl]prop-2-en-1-one and 1-[2-hydroxyphenyl]-3-[3-isopropyloxycarbonyldimethylmethyloxyphenyl]prop-2-en-1-one:

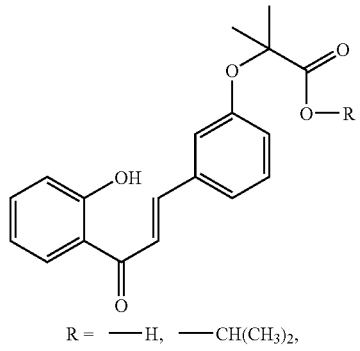

R = —H, —CH(CH₃)₂,

1-[2-hydroxyphenyl]-3-[4-carboxydimethylmethylthiophenyl]prop-2-en-1-one and 1-[2-hydroxyphenyl]-3-[4-isopropyloxycarbonyldimethylmethylthiophenyl]prop-2-en-1-one:

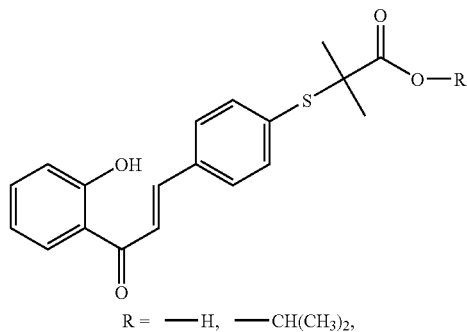

R = —H, —CH(CH₃)₂,

1-[2-mercapto-4-methyloxyphenyl]-3-[4-carboxydimethylmethyloxyphenyl]prop-2-en-1-one and 1-[2-mercapto-4-methyloxyphenyl]-3-[4-isopropyloxycarbonyldimethylmethyloxyphenyl]prop-2-en-1-one:

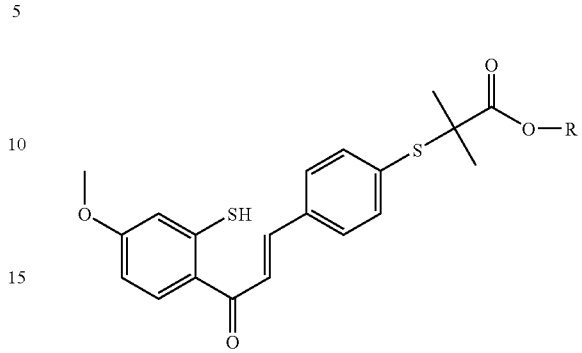

1-[4-heptylphenyl]-3-[3-methyl-4-carboxydimethylmethyloxyphenyl]prop-2-en-1-one and 1-[4-heptylphenyl]-3-[3-methyl-4-isopropyloxycarbonyldimethylmethyloxyphenyl]prop-2-en-1-one:

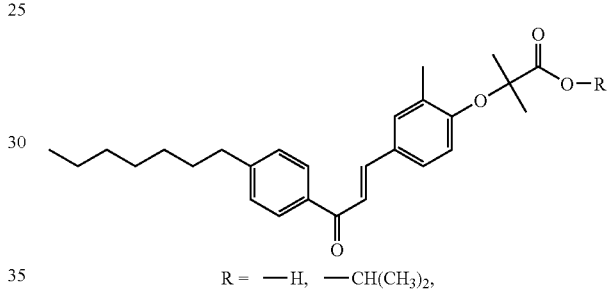

R = —H, —CH(CH₃)₂,

1-[2-hydroxy-4-carboxydimethylmethyloxyphenyl]-3-[3,5-dibromo-4-hydroxyphenyl]prop-2-en-1-one,
1-[2-hydroxy-4-carboxydimethylmethyloxyphenyl]-3-[3-hydroxyphenyl]prop-2-en-1-one,
1-[2-hydroxy-4-carboxydimethylmethyloxyphenyl]-3-[4-methylthiophenyl]prop-2-en-1-one,
1-[2-hydroxy-4-carboxydimethylmethyloxyphenyl]-3-[4-methylthiophenyl]prop-2-en-1-one,
1-[2,4-dihydroxyphenyl]-3-[4-carboxydimethylmethyloxyphenyl]prop-2-en-1-one,
1-[2-hydroxyphenyl]-3-[4-carboxydimethylmethyloxyphenyl]prop-2-en-1-one,
1-[4-chlorophenyl]-3-[3,5-dimethyl-4-tertbutyloxycarbonyldimethylmethyloxyphenyl]prop-2-en-1-one,
1-[4-chlorophenyl]-3-[3,5-dimethyl-4-isopropyloxycarbonyldimethylmethyloxyphenyl]prop-2-en-1-one,
1-[4-chlorophenyl]-3-[3,5-dimethyl-4-carboxydimethylmethyloxyphenyl]prop-2-en-1-one,
1-[2-hydroxy-4-carboxydimethylmethyloxyphenyl]-3-[4-chlorophenyl]prop-2-en-1-one,
1-[2-hydroxyphenyl]-3-[4-carboxydimethylmethylthiophenyl]prop-2-en-1-one,
1-[4-chloro-2-hydroxyphenyl]-3-[4-carboxydimethylmethylthiophenyl]prop-2-en-1-one,
1-[4-carboxydimethylmethyloxyphenyl]-3-[3,5-dimethyl4-hydroxyphenyl]prop-2-en-1-one,
1-[4-methylthiophenyl]-3-[4-carboxydimethylmethyloxyphenyl]prop-2-en-1-one,
1-[4-carboxydimethylmethyloxyphenyl]-3-[4-chlorophenyl]prop-2-en-1-one, 1-[4-carboxydimethylmethylthiophenyl]-3-[4-methylthiophenyl]prop-2-en-1-one,
1-[2-hydroxy-4-bromophenyl]-3-[3,5-dimethyl-4-carboxydimethylmethyloxyphenyl]prop-2-en-1-one,
1-[4-carboxydimethylmethyloxyphenyl]-3-[4-methylthiophenyl]prop-2-en-1-one,
1-[4-methylthiophenyl]-3-[3,5-dimethyl-4-tertbutyloxycarbonyldimethylmethyloxyphenyl]prop-2-en-1-one,
1-[4-methylthiophenyl]-3-[3,5-dimethyl-4-isopropyloxycarbonyldimethylmethyloxyphenyl]prop-2-en-1-one,
1-[4-methylthiophenyl]-3-[3,5-dimethyl-4-carboxydimethylmethyloxyphenyl]prop-2-en-1-one,
1-[2-methoxyphenyl]-3-[3,5-dimethyl-4-tertbutyloxycarbonyldimethylmethyloxyphenyl]prop-2-en-1-one,
1-[2-methoxyphenyl]-3-[3,5-dimethyl-4-carboxydimethylmethyloxyphenyl]prop-2-en-1-one,
1-[4-hexyloxyphenyl]-3-[3,5-dimethyl-4-tertbutyloxycarbonyldimethylmethyloxyphenyl]prop-2-en-1-one,
1-[4-hexyloxyphenyl]-3-[3,5-dimethyl-4-carboxydimethylmethyloxyphenyl]prop-2-en-1-one,
2-(3,5-dimethyl-4-tertbutyloxycarbonyldimethylmethyloxyphenyl)-7-chloro-4H-1-benzopyran-4-one,
2-(3,5-dimethyl-4-carboxydimethylmethyloxyphenyl)-7-chloro-4H-1-benzopyran-4-one,
1-[2-methyloxy-4-chlorophenyl]-3-[3,5-dimethyl-4-tertbutyloxycarbonyldimethylmethyloxyphenyl]prop-2-en-1-one,
1-[2-methyloxy-4-chlorophenyl]-3-[3,5-dimethyl-4-carboxydimethylmethyloxyphenyl]prop-2-en-1-one,
1-[4-heptylphenyl]-3-[3,5-dimethyl-4-tertbutyloxycarbonyldimethylmethyloxyphenyl]prop-2-en-1-one,
1-[4-heptylphenyl]-3-[3,5-dimethyl-4-carboxydimethylmethyloxyphenyl]prop-2-en-1-one,
1-[4-bromophenyl]-3-[3,5-dimethyl-4-dimethylmethyloxyphenyl]prop-2-en-1-one,
1-[4-bromophenyl]-3-[3,5-dimethyl-4-carboxy dimethylmethyloxyphenyl]prop-2-en-1-one,
1-[2-hydroxyphenyl]-3-[3,5-dimethyl-4-isopropyloxycarbonyl dimethylmethyloxyphenyl]prop-2-en-1-one The invention thus concerns the use of at least one compound represented by formula (I) such as defined hereinabove and in particular one of the advantageous or preferred compounds for preparing a pharmaceutical composition for the preventive or preferably curative treatment of a pathology related to inflammation, neurodegeneration, deregulations of lipid and/or glucose metabolism, cell proliferation and/or differentiation and/or skin or central nervous system ageing, such as allergy, asthma, eczema, psoriasis, pruritus, Alzheimer's disease, Parkinson's disease, diabetes, atherosclerosis, obesity, carcinogenesis, etc.

The invention also provides a method for preparing compounds or derivatives represented by formula (I).

The method of the invention comprises contacting in a basic medium or in an acidic medium at least one compound represented by formula (A) with at least one compound represented by formula (B), formulas (A) and (B) being:

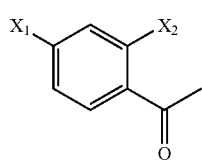

(A)

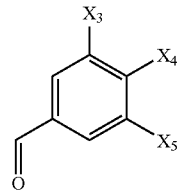

(B)

formulas in which X1, X2, X3, X4 and X5 are such as defined hereinabove.

The conditions for carrying out said reaction in acidic or basic medium are within reach of those skilled in the art and can vary widely.

Said two compounds are advantageously contacted in stoichiometric proportions. Contact is preferably carried out at room temperature (between approximately 18° C. and 25° C.) and at atmospheric pressure.

In basic medium, the reaction is preferably carried out in the presence of a strong base, such as an alkaline earth metal hydroxide, like sodium hydroxide or an alkaline metal alcoholate like sodium ethylate.

In acidic medium, the reaction is preferably carried out in the presence of a strong acid, such as hydrochloric acid.

The reaction scheme may be depicted as follows:

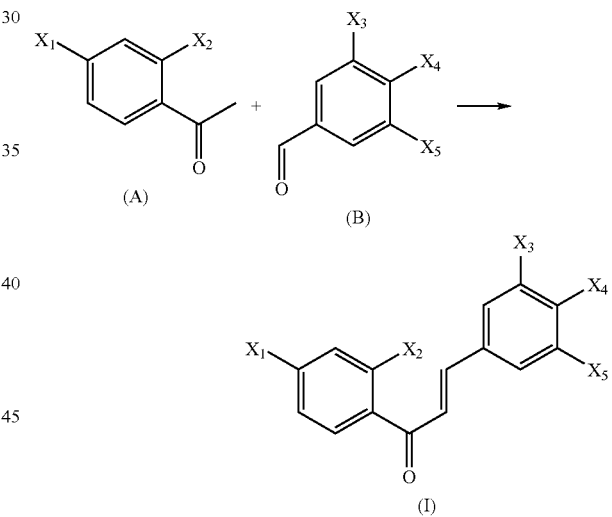

The synthesis in basic medium may be carried out in the following manner:

One molar equivalent of ketone (compound (A)) and one molar equivalent of aldehyde (compound (B)) are solubilized in a hydroalcoholic solution of 20 molar equivalents of sodium hydroxide. The mixture is stirred for approximately 18 hours at room temperature (between 18° C. and 25° C.). The medium is then acidified (in particular to a pH of approximately 2) in particular with hydrochloric acid The expected substituted 1,3-diphenylprop-2-en-1-one can be obtained by precipitation or solid/liquid extraction after evaporation of the reaction medium. It can then be purified by silica gel chromatography or by crystallization.

The synthesis in acidic medium may be carried out in the following manner:

One molar equivalent of ketone (compound (A)) and one molar equivalent of aldehyde (compound (B)) are solubilized in an ethanol solution saturated with gaseous hydrochloric acid. The mixture is stirred at room temperature for approximately 6 hours, the solvent is eliminated, in particular by vacuum evaporation. The substituted 1,3-diphenylprop-2-en-1-one is purified, in particular by chromatography on silica gel.

The invention thus concerns the use of a compound or derivative such as defined hereinabove for preparing a pharmaceutical composition for practicing a method of treatment or prophylaxis of the human or animal body.

The pharmaceutical compositions or compounds represented by formula (I) according to the invention are advantageously used for the treatment or prophylaxis of pathologies related to inflammation, neurodegeneration, deregulations of lipid and/or glucose metabolism, cell proliferation and/or differentiation and/or skin or central nervous system ageing and more particularly of one or more allergies, asthma, eczema, psoriasis, pruritus, Alzheimer's disease, Parkinson's disease, diabetes, atherosclerosis, obesity, carcinogenesis, etc. In fact, it was found surprisingly that compounds represented by formula (I) have advantageous pharmacological properties as antioxidants and activators of PPARα and PPARγ.

In the case where the composition of the invention is intended for the treatment or prophylaxis of a pathology related to neurodegeneration, deregulations of lipid and/or glucose metabolism, cell proliferation and/or differentiation and/or skin or central nervous system ageing, the compounds represented by formula (I) can optionally include those having formula (I) in which $X_2$ represents a hydrogen atom and $X_1$ represents -G1R1 where G1 represents an oxygen atom and R1 represents CH2COOH. Preferably, however, said compounds are excluded.

In the case where the composition of the invention is intended for the treatment or prophylaxis of a pathology related to inflammation, neurodegeneration, cell proliferation and/or differentiation and/or skin or central nervous system ageing and more particularly of one or more allergies, asthma, eczema, psoriasis, pruritus, Alzheimer's disease, Parkinson's disease or carcinogenesis, the compounds represented by formula (I) can optionally include those having formula (I) in which:

$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group (comprising one or two carbon atoms), and $R_{10}$ represents a hydrogen atom or a C1 to C7 alkyl group, $X_2$, $X_3$ and $X_5$ each represent a hydrogen atom, $X_1$ represents a halogen atom or a R1 or -G1R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group (comprising one to seven carbon atoms).

The invention also concerns a method for treating pathologies related to inflammation, neurodegeneration, deregulations of lipid and/or glucose metabolism, cell proliferation and/or differentiation and/or skin or central nervous system ageing and more particularly of one or more allergies, asthma, eczema, psoriasis, pruritus, Alzheimer's disease, Parkinson's disease, diabetes, atherosclerosis, obesity, carcinogenesis, comprising administering to a subject, particularly human, an effective dose of a compound represented by general formula (I) or of a pharmaceutical composition such as defined hereinabove.

The pharmaceutical compositions according to the invention advantageously comprise one or more pharmaceutically acceptable excipients or vehicles. Examples include saline, physiological, isotonic, buffered solutions and the like, compatible with pharmaceutical use and known to those skilled in the art. The compositions may contain one or more agents or vehicles selected in the group consisting of dispersants, solubilizers, stabilizers, preservatives, and the like. Agents or vehicles that can be used in the formulations (liquid and/or injectable and/or solid) are in particular methylcellulose, hydroxymethylcellulose, carboxymethylcellulose, polysorbate 80, mannitol, gelatin, lactose, plant oils, acacia, and the like. The compositions may be formulated as suspensions for injection, gels, oils, tablets, suppositories, powders, capsules, gelules, and the like, possibly by means of pharmaceutical forms or devices ensuring prolonged and/or delayed release. For this type of formulation, an agent such as cellulose, carbonates or starch is advantageously used.

The compounds or compositions of the invention may be administered in different ways and in different forms. For instance, they may be administered by the oral or systemic route, such as for example by the intravenous, intramuscular, subcutaneous, transdermal, intra-arterial route, etc. For injections, the compounds are generally formulated as liquid suspensions, which can be injected through syringes or by infusion, for example. It is understood that the injection rate and/or the injected dose may be adapted by those skilled in the art according to the patient, the pathology, the method of administration, etc. Typically, the compounds are administered at doses ranging from 1 µg to 2 g per administration, preferably from 0.1 mg to 1g per administration. The administrations may be given daily or repeated several times a day, as the case may be. Moreover, the inventive compositions may additionally comprise other active ingredients or agents.

Other aspects and advantages of the invention will become apparent in the following examples, which are given for purposes of illustration and not by way of limitation.

LEGENDS OF FIGURES

FIG. 1-1, 1-2, 1-3: Evaluation of the antioxidant properties of compound 2, compound 3, compound 12, compound 14 and compound 17 on LDL oxidation by copper (Cu).

FIG. 1-1 shows the results of the experiment measuring formation of conjugated dienes over time. It can be seen that incubation of LDL with the test compounds at a concentration of $10^4$ M delayed conjugated diene formation. The lag phase was 111 minutes for copper alone as compared with a lag phase of 132, 145, 134 and 203 minutes, respectively, when LDL were incubated with compound 3, compound 12, compound 14, compound 17. The lag phase was more than 480 minutes when LDL were incubated with compound 2. This lag in the formation of conjugated dienes is characteristic of antioxidants.

FIG. 1-2 shows the rate of diene formation after different treatments. Incubation of the compounds with LDL in the presence of copper slowed the rate of conjugated diene formation. This rate was 2 nmol/min/mg of LDL with copper alone, 1.7 nmol/min/mg of LDL when LDL were incubated in the presence of $10^{-4}$ M compound 17, and not determined for compound 2 at $10^{-4}$ M (not measurable because too low).

FIG. 1-3 represents the maximum amount of conjugated dienes formed over time. Incubation of LDL with copper led to formation of 348 nmol of conjugated dienes per mg of LDL; incubation with compound 2 at $10^{-4}$ M led to an 84% decrease in conjugated diene formation (54.4 nmol per mg of LDL). In the presence of compounds 3 and 17, conjugated diene formation was respectively 303 and 327 nmol per mg of LDL.

FIG. 1-4, 1-5, 1-6: Evaluation of the antioxidant properties of compound 18, compound 19, compound 21 and compound 22 on LDL oxidation by copper (Cu).

FIG. 1-4 shows that incubation of LDL with the test compounds at a concentration of $10^{-4}$ M delayed conjugated diene formation. The lag phase was 178 minutes for copper alone as compared with a lag phase of 241, 182 and 241 minutes (from the experimental determination), respectively, when LDL were incubated with compound 18, compound 19, or compound 22. The lag phase was more than 480 minutes when LDL were incubated with compound 21. This lag in the formation of conjugated dienes is characteristic of antioxidants.

FIG. 1-5 shows the rate of diene formation after different treatments. The rate of formation of conjugated dienes was 1.6 nmol/min/mg of LDL with copper alone, 1.4 nmol/min/mg of LDL when LDL were incubated in the presence of compound 18 at $10^{-4}$ M, 1.3 nmol/min/mg of LDL when LDL were incubated in the presence of compounds 22, and not determined for compound 21 at $10^{-4}$ M (not measurable because too low).

FIG. 1-6 represents the maximum amount of conjugated dienes formed over time. Incubation of LDL with copper led to formation of 353 nmol of conjugated dienes per mg of LDL. Incubation with compound 21 at $10^{-4}$ M inhibited conjugated diene formation. Conjugated diene formation was respectively 305, 345 and 345 nmol per mg of LDL in the presence of compounds 18, 19 and 22.

FIG. 1-7, 1-8: Evaluation of the antioxidant properties of compound 25 and compound 28 on LDL oxidation by copper (Cu).

FIGS. 1-7 shows the results of the experiment measuring formation of conjugated dienes over time. It can be seen that incubation of LDL with the test compounds at a concentration of $10^{-4}$ M delayed conjugated diene formation. The lag phase was 82 minutes for copper alone as compared with a lag phase of 120 and 135 minutes (from the experimental determination), respectively, when LDL were incubated with compound 25 and compound 29.

FIG. 1-8 represents the maximum amount of conjugated dienes formed over time. Incubation of LDL with copper led to formation of 393 nmol of conjugated dienes per mg of LDL. In the presence of compound 25 this value was 378 nmol per mg of LDL.

FIGS. 1-9, 1-10, 1-11: Evaluation of the antioxidant properties of compound 31, compound 33 and compound 35 on LDL oxidation by copper (Cu).

FIG. 1-9 shows the results of the experiment measuring formation of conjugated dienes over time. It can be seen that incubation of LDL with the test compounds at a concentration of $10^{-4}$ M delayed conjugated diene formation. The lag phase was 80 minutes for copper alone as compared with a lag phase of 139, 247 and 149 minutes (from the experimental determination), respectively, when LDL were incubated with compound 31, compound 33, and compound 35. This lag in the formation of conjugated dienes is characteristic of antioxidants.

FIG. 1-10 shows the rate of diene formation after different treatments. Incubation of the compounds with LDL in the presence of copper slowed the rate of conjugated diene formation. This rate was 1.9 nmol/min/mg of LDL with copper alone, 1.6 nmol/min/mg of LDL when LDL were incubated in the presence of compound 31 at $10^{-4}$ M, 0.8 nmol/min/mg of LDL when LDL were incubated in the presence of compound 33 and 1.5 nmol/min/mg of LDL when LDL were incubated in the presence of compound 35.

FIG. 1-11 represents the maximum amount of conjugated dienes formed over time. Incubation of LDL with copper led to formation of 298 nmol of conjugated dienes per mg of LDL, as compared with 257 nmol per mg of LDL in the presence of compound 33.

FIG. 1-12, 1-13, 1-14: Evaluation of the antioxidant properties of compound 37, compound 38 and compound 41 on LDL oxidation by copper (Cu).

FIG. 1-12 shows the results of the experiment measuring formation of conjugated dienes over time. It can be seen that incubation of LDL with the test compounds at a concentration of $10^{-4}$ M delayed conjugated diene formation. The lag phase was 120 minutes for copper alone as compared with a lag phase of 196, 284 and 411 minutes (from the experimental determination), respectively, when LDL were incubated with compound 37, compound 38, and compound 41.

FIG. 1-13 shows the rate of diene formation after different treatments. Incubation of the compounds with LDL in the presence of copper slowed the rate of conjugated diene formation. This rate was 1.8 nmol/min/mg of LDL with copper alone, 1.49 nmol/min/mg of LDL when LDL were incubated in the presence of compounds 37 at $10^{-4}$ M, 0.71 nmol/min/mg of LDL when LDL were incubated in the presence of compounds 38 and 0.54 nmol/min/mg of LDL when LDL were incubated in the presence of compounds 41.

FIG. 1-14 represents the maximum amount of conjugated dienes formed over time. Incubation of LDL with copper led to formation of 372 nmol of conjugated dienes per mg of LDL, as compared with 338 nmol per mg of LDL, 244 nmol per mg of LDL, and 71 nmol per mg of LDL in the presence of compounds 37, 38 and 41, respectively.

The lag phase in the formation of conjugated dienes, the reduction in the rate of diene formation and the decrease in the total amount of dienes formed are characteristics of antioxidants.

FIGS. 2-1, 2-2, 2-3, 2-4, 2-5, 2-6: Evaluation of PPARα agonist properties of the inventive compounds in the PPARα/Gal4 transactivation system.

RK13 cells were incubated with the different compounds at concentrations of 10, and 100 μM or 1, 10 and 100 μM for 24 hours. The results are expressed as the induction factor (luminescent signal relative to untreated cells) after the different treatments. The higher the induction factor the more potent the PPARα agonist activity.

FIG. 2-1:

The results show the induction factors for compound 3, compound 4, compound 7, compound 8 and compound 9. The values of these induction factors are given in Table 2-1.

TABLE 2-1

| Compound | Concentration | Induction factor |
|---|---|---|
| Cp3 | 10 μM | 30.12 |
|  | 30 μM | 27.27 |
|  | 100 μM | 25.84 |
| Cp4 | 10 μM | 3.99 |
|  | 30 μM | 22.15 |
|  | 100 μM | 61.07 |
| Cp7 | 10 μM | 36.48 |
|  | 30 μM | 50.37 |
|  | 100 μM | 37.84 |

TABLE 2-1-continued

| Compound | Concentration | Induction factor |
|---|---|---|
| Cp8 | 10 μM | 0.62 |
|  | 30 μM | 1.27 |
|  | 100 μM | 9.98 |
| Cp9 | 10 μM | 2.11 |
|  | 30 μM | 5.00 |
|  | 100 μM | 28.19 |

The results show that compound 3 produced a maximum 27-fold induction at a concentration of 30 μM, compound 4 had a maximum induction factor of 60 at 100 μM, 22 at 30 μM and 4 at 10 μM. Compound 7 had a maximum induction factor of 50 at 100 μM. Compound 8 activated the system with a maximum induction factor of 10 at 100 μM. Compound 9 had an induction factor of 28 at 100 μM, the highest concentration

FIG. 2-2:

The results show the induction factors for compound 11, compound 12, compound 13, compound 14 and compound 17. The values of these induction factors are given in Table 2-2.

TABLE 2-2

| Compound | Concentration | Induction factor |
|---|---|---|
| Cp11 | 1 μM | 1.20 |
|  | 10 μM | 1.39 |
|  | 100 μM | 10.19 |
| Cp12 | 1 μM | 1.12 |
|  | 10 μM | 8.45 |
|  | 100 μM | 22.54 |
| Cp13 | 1 μM | 1.20 |
|  | 10 μM | 1.10 |
|  | 100 μM | 1.5 |
| Cp14 | 1 μM | 1.25 |
|  | 10 μM | 1.36 |
|  | 100 μM | 1.38 |
| Cp17 | 1 μM | 79.76 |
|  | 10 μM | 85.69 |
|  | 100 μM | 13.80 |

The results show that compound 11 produced a maximum 10-fold induction at a concentration of 100 μM, compound 12 had a maximum induction factor of 22 at 100 μM, 8 at 30 μM and 1 at 10 μM. Compounds 13 and 14 had induction factors comprised between 1.1 and 1.5 at the different concentrations tested. Compound 17 activated the system with a maximum induction factor of 85 at 10 μM and a minimum induction factor of 13.8 at the 100 μM concentration.

FIG.: 2-3

The results show the induction factors for compound 19, compound 20, compound 21 and compound 22. The values of these induction factors are given in Table 2-3.

TABLE 2-3

| Compound | Concentration | Induction factor |
|---|---|---|
| Cp19 | 1 μM | 1.20 |
|  | 10 μM | 15.62 |
|  | 100 μM | 0.07 |
| Cp20 | 1 μM | 21.50 |
|  | 10 μM | 53.45 |
|  | 100 μM | 1.22 |
| Cp21 | 1 μM | 0.78 |
|  | 10 μM | 1.10 |
|  | 100 μM | 22.80 |

TABLE 2-3-continued

| Compound | Concentration | Induction factor |
|---|---|---|
| Cp22 | 1 μM | 2.40 |
|  | 10 μM | 49.49 |
|  | 100 μM | 2.73 |

The results show that compound 19 produced a maximum 15.6-fold induction at 10 μM, compound 20 had a maximum induction factor of 53 at 10 μM. Compound 21 had induction factors comprised between 0.8 and 22 at the different concentrations tested. Compound 22 activated the system with a maximum induction factor of 50 at the 10 μM concentration.

FIG.: 2-4

The results show the induction factors for compounds 23, 24, 25, 26 and 29. The values of these induction factors are given in Table 2-4.

TABLE 2-4

| Compound | Concentration | Induction factor |
|---|---|---|
| Cp23 | 1 μM | 1.55 |
|  | 10 μM | 3.67 |
|  | 100 μM | 0.12 |
| Cp24 | 1 μM | 2.06 |
|  | 10 μM | 11.62 |
|  | 100 μM | 0.00 |
| Cp25 | 1 μM | 13.48 |
|  | 10 μM | 21.03 |
|  | 100 μM | 7.01 |
| Cp26 | 1 μM | 1.75 |
|  | 10 μM | 7.85 |
|  | 100 μM | 1.08 |
| Cp29 | 1 μM | 28.36 |
|  | 10 μM | 25.26 |
|  | 100 μM | 0.27 |

Compound 23 had a maximum induction factor of 3.6 at 10 μM, compound 24 had a maximum induction factor of 11 at 10 μM. Compound 25 activated the system with induction factors comprised between 7 and 21 according to the concentrations tested. Compound 26 had a maximum induction factor of 7.8 for the 10 μM concentration, compound 29 had induction factors of 28 and 25 at 1 and 10 μM, respectively.

FIG.: 2-5

The results show the induction factors for compound 31 and compound 33. The values of these induction factors are given in Table 2-5.

TABLE 2-5

| Compound | Concentration | Induction factor |
|---|---|---|
| Cp31 | 1 μM | 3.77 |
|  | 10 μM | 15.52 |
|  | 100 μM | 1.21 |
| Cp33 | 1 μM | 22.05 |
|  | 10 μM | 44.52 |
|  | 100 μM | 77.62 |

Compound 31 activated the system with an induction factor of 15.5 at the concentration of 10 μM. The induction factors for compound 33 were 22, 44 and 77 for the 1, 10 and 100 μM concentrations, respectively.

FIG.: 2-6

The results show the induction factors for compounds 37, 38 and 41. The values of these induction factors are given in Table 2-6.

TABLE 2-6

| Compound | Concentration | Induction factor |
|---|---|---|
| Cp37 | 1 μM | 24.55 |
|  | 10 μM | 27.83 |
|  | 100 μM | 0.02 |
| Cp38 | 1 μM | 14.70 |
|  | 10 μM | 22.22 |
|  | 100 μM | 0.311 |
| Cp41 | 1 μM | 34.61 |
|  | 10 μM | 31.18 |
|  | 100 μM | 3.39 |

The maximum induction factors for compounds 37, 38 and 41 were 27, 22 and 31, respectively, at the 10 μm concentration.

These results demonstrate that the inventive compounds tested exhibit PPARα ligand activity and thus enable the transcriptional activation thereof.

FIG. 2-7: Evaluation of PPARγ agonist properties of the inventive compounds in the PPARγ/Gal4 transactivation system.

RK13 cells were incubated with the different compounds at concentrations of 1, and 100 μM for 24 hours. The results are expressed as the induction factor (luminescent signal relative to untreated cells) after the different treatments. The higher the induction factor the more potent the PPARγ agonist activity.

The results in the figure show the induction factors for compound 17, compound 33, and compound 29. The values of these induction factors are given in Table 2-7.

TABLE 2-7

| Compound |  | Induction factor |
|---|---|---|
| Cp17 | 1 μM | 15.37 |
|  | 10 μM | 24.92 |
|  | 100 μM | 6.13 |
| Cp33 | 1 μM | 15.65 |
|  | 10 μM | 33.90 |
|  | 100 μM | 45.58 |
| Cp29 | 1 μM | 17.05 |
|  | 10 μM | 33.89 |
|  | 100 μM | 0.01 |

The results show that compound 17 had a maximum induction factor of 25 at 10 μM. Compound 33 had a maximum induction factor of 45.6 at 100 μM and compound 29 of 33.9 at 10 μM.

These results demonstrate that the inventive compounds tested exhibit PPARγ ligand activity and thus enable the transcriptional activation thereof.

FIGS.: 3-1, 3-2, 3-3, 3-4: Evaluation of the effect of compound 7 and compound 17 on metabolism of triglycerides and cholesterol.

FIGS. 3-1, 3-2, 3-3 and 3-4 illustrate the effects of treatment with compounds 7 and 17 on triglyceride and cholesterol metabolism in Apo E2/E2 transgenic mice. Animals were treated by gavage with each compound at a dose of 200 mg/kg for 7 days.

FIGS. 3-1 and 3-2 illustrate the decrease in plasma concentrations of triglycerides and cholesterol induced by compounds 7 and 17.

FIGS. 3-3 and 3-4 show triglyceride and cholesterol distribution in lipoparticles evaluated by exclusion chromatography. A typical distribution of triglycerides and cholesterol is observed principally in large sized lipoparticles. It can also be seen that treatment with compounds 7 and 17 decreased the triglycerides and cholesterol in this lipoparticle subfraction.

FIGS. 3-5, 3-6, 3-7, 3-8:

FIGS. 3-5, 3-6, 3-7 and 3-8 illustrate the effects of treatment with compound 29 according to the invention on triglyceride and cholesterol metabolism in Apo E2/E2 transgenic mice. Animals were treated with compound 29 at the following doses: 200, 50, 12.5 and 3.15 mg/kg/day for 8 days.

FIGS. 3-5 and 3-6 illustrate the dose-dependent decrease in plasma triglyceride and cholesterol levels with a greater decrease with increasing doses of compound 29.

FIGS. 3-7 and 3-8 show triglyceride and cholesterol distribution in lipoparticles evaluated by exclusion chromatography. A typical distribution of triglycerides and cholesterol is observed principally in large sized lipoparticles. A decrease in triglycerides and cholesterol in this lipoparticle subfraction can also be seen.

FIGS. 3-9, 3-10, 3-11, 3-12:

FIGS. 3-9 and 3-10 illustrate the effect of compounds 33 and 41 according to the invention on triglyceride and cholesterol metabolism in Apo E2/E2 transgenic mice. The animals were treated with the different compounds at a dose of 50 mg/kg/day for 8 days. FIGS. 5-1 and 5-2 show the decrease in plasma triglycerides and cholesterol induced by compounds 33 and 41.

FIGS. 3-11 and 3-12 show triglyceride and cholesterol distribution in lipoparticles evaluated by exclusion chromatography. A typical distribution of triglycerides and cholesterol is observed principally in large sized lipoparticles as well as a decrease in triglycerides and cholesterol in this lipoparticle subfraction under the effect of compounds 33 and 41.

Other aspects and advantages of the invention will become apparent in the following examples, which are given for purposes of illustration and not by way of limitation.

EXAMPLES

The inventive compounds were prepared according to the general methods outlined below.

DESCRIPTION OF GENERAL SYNTHETIC METHODS OF THE INVENTION

Synthesis of 1,3-diphenylprop-2-en-1-ones

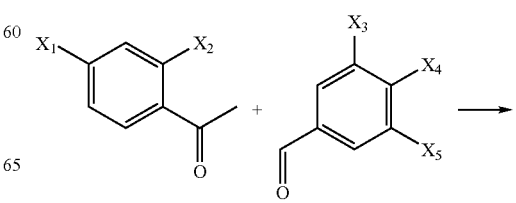

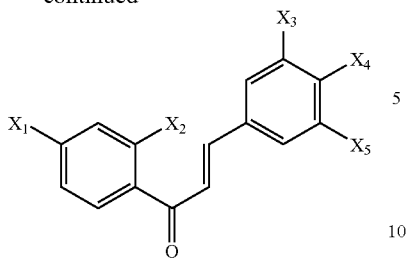

X1 = OH, Cl, Br —SCH3, —OC6H13, —C7H15, OC(CH3)2COOR6, SC(CH3)2COOR6,
X2 = H, O(2-phenyl-4-H-1-benzopyran-4-one), OCH3, OH
X4 = OH, Cl, Br, —SCH3, OC(CH3)2COOR6, SC(CH3)2COOR6
X3 and X5 = CH3, C(CH3)3, OCH3, OH, OC(CH3)2COOR6
R6 = CH2CH3, H General Method 1:

Synthesis of 1,3-diphenylprop-2-en-1-ones in Acidic Medium

The ketone (1 eq) and the aldehyde (1 eq) were dissolved in ethanol solution saturated with gaseous hydrochloric acid. The reaction was stirred at room temperature for 6 hours and the solvent was then eliminated by vacuum evaporation. 1,3-diphenylprop-2-en-1-one was purified by chromatography on silica gel.

General Method 2:

Synthesis of 1,3-diphenylprop-2-en-1-ones in Basic Medium

The ketone (1 eq) and the aldehyde (1 eq) were dissolved in a hydroalcoholic solution of sodium hydroxide (20 eq). The mixture was stirred at room temperature for 18 hours. The medium was acidified to pH=2 with hydrochloric 1,3-diphenylprop-2-en-1-one was obtained by precipitation or solid/liquid traction after evaporation of the reaction medium. It was purified by silica gel chromatography or by recrystallization.

General Method 3:

Synthesis of substituted 1,3-diphenylprop-2-en-1-ones in the Presence of Sodium Ethylate Sodium (1 eq) was dissolved in absolute ethanol. The ketone (1 eq) and the aldehyde (1 eq) were added. The reaction mixture was stirred at room temperature for 12 hours and 2 N sodium hydroxide (5 eq) was then added. The mixture was kept at 100° C. for 12 hours. The reaction medium was acidified by adding 6 N aqueous hydrochloric acid solution. The solvent was eliminated by vacuum evaporation. The residue was purified by chromatography on silica gel or by recrystallization.

O-Alkylation of Phenols and S-alkylation of Thiophenols
General Method 4:

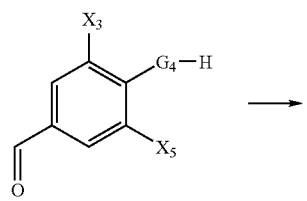

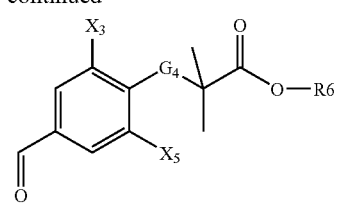

G4 = O, S
X3, X5 = H, CH3, OCH3
R6 = CH2CH3

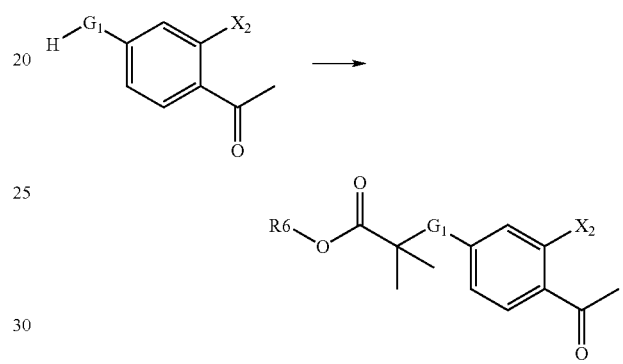

G1 = O, S
X2 = H, OH
R6 = CH2CH3

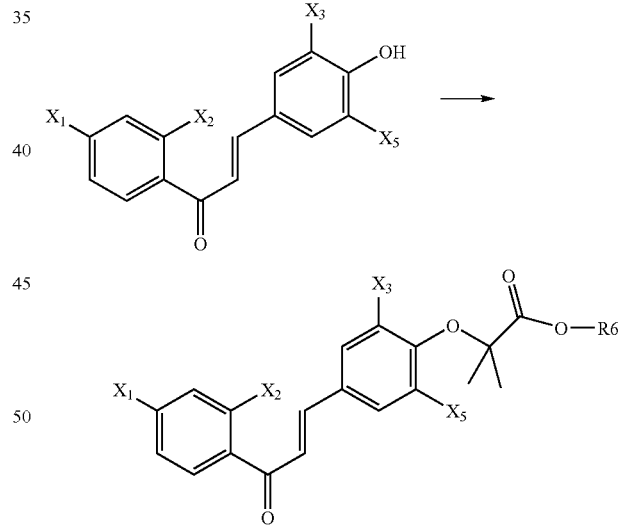

X1 = Cl, Br—SCH3, —OC6H13, —C7H15
X2 = H, O(2-phenyl-4-H-1-benzopyran-4-one), OCH3
X3 and X5 = CH3
R6 = CH2CH3, H The phenol (1 eq) was dissolved in acetonitrile. The halogenated derivative (1 to 10 eq) and potassium carbonate (5 eq) were then added. The reaction medium was briskly stirred under reflux for approximately 10 hours. The salts were eliminated by filtration, the solvent and excess reagent were eliminated by vacuum evaporation, and the expected product was purified by silica gel chromatography.

Acid Hydrolysis of Tertbutylic Esters:
General Method 5:

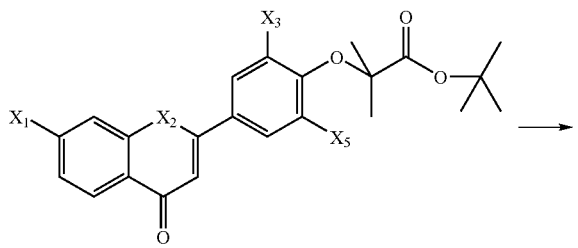

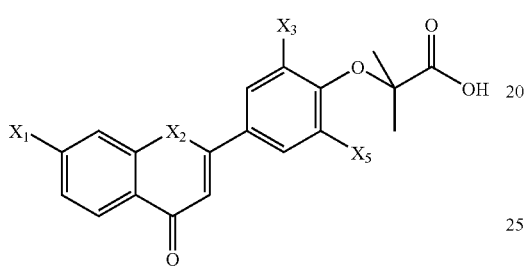

X3 and X5 = CH3,
X2 = H, O(2-phenyl-4-H-1-benzopyran-4-one), OCH3,
X1 = Cl, Br, ──SCH3, OC6H13, ──C7H15

The tertbutylic ester (1 eq) was dissolved in dichloromethane, trifluoroacetic acid (10 eq) was added, and the mixture was stirred at room temperature for 12 hours. The resulting product was purified by chromatography on silica gel or by recrystallization.

Synthesis of Starting Materials used to Synthesize the Inventive Compounds:

Starting Material 1

2'-Hydroxy-4'-(ethoxycarbonyldimethylmethoxy)acetophenone

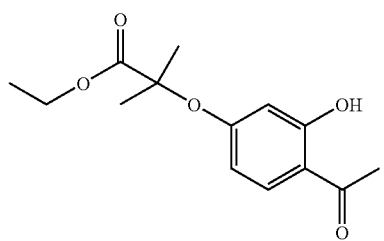

This compound was synthesized from 2',4'-dihydroxyacetophenone and ethyl bromoisobutyrate (1 eq) according to general method 4 described earlier. It was purified by chromatography on silica gel (elution:cyclohexane/ethyl acetate 9:1).

1H NMR CDCl$_3$ δppm: 1.25 (t, J=7.17 Hz, 3H), 1.67 (s, 6H), 2.56 (s, 3H), 4.24 (q, J=7.17 Hz, 2H), 6.27 (d, J=2.55 Hz, 1H), 6.37 (dd, J=2.55 Hz, J=8.72 Hz, 1H), 7.62 (d, J=8.72 Hz, 1H), 12.6 (signal, 1H).

Reference: U.S. Pat. No. 3,629,290 (1970), Fisons Pharmaceutical

Starting Material 2

3-chlorophenyl acetate

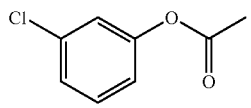

3-chlorophenol was dissolved in dichloromethane. Triethylamine (1 eq) and acetic anhydride (2 eq) were added. The mixture was stirred at room temperature for 5 hours. Solvent was eliminated by vacuum evaporation. The evaporation residue was taken up in dichloromethane, dried on magnesium sulfate and the solvent was eliminated by vacuum evaporation. Purification was carried out by chromatography on silica gel (elution:cyclohexane/ethyl acetate 95:5).

1H NMR CDCl$_3$ δppm: 2.29 (s, 3 H), 6.99-7.33 (m, 4 H)

Starting Material 3

4'-Chloro-2'-hydroxyacetophenone

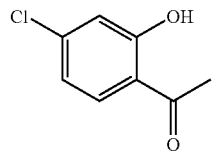

3-chlorophenyl acetate (starting material 2) was mixed with aluminium chloride (3 eq). The mixture was heated at 200° C. for 1 hour. The reaction medium was cooled to room temperature then poured in ice. The aqueous phase was extracted with methylene chloride which was dried on magnesium sulfate then vacuum evaporated.

Purification was by silica gel chromatography (elution: cyclohexane/ethyl acetate 95:5).

1H NMR CDCl$_3$ δppm: 3.41 (s, 3 H), 6.81 (dd, J=8.82 Hz, J=1.47 Hz, 1H), 6.91 (d, J=1.47 Hz, 1H), 7.60 (d, 8.82 Hz, 1H), 12.33 (s, 1H)

Reference: Chen et al, J Chem Soc, 1958, 146-148.

Starting material 4

4-Ethyloxycarbonyldimethylmethyloxybenzaldehyde

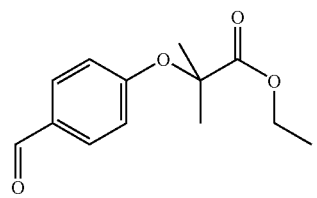

This compound was synthesized from 4-hydroxyabenzaldehyde and ethyl bromoisobutyrate according to general method 4 described earlier.

Purification was carried out by silica gel chromatography (elution:cyclohexane/ethyl acetate 9:1).

1H NMR CDCl$_3$ δ ppm: 1.20 (t, J=6.96 Hz, 3H), 1.67 (s, 6H), 4.21 (q, J=6.96 Hz, 2H), 6.89 (d, J=8.91 Hz, 2H), 7.79 (d, J=8.94 Hz, 2H), 9.87 (S, 1H).

Starting material 5 3,5-dimethyloxy-4-ethyloxycarbonyldimethylmethyloxybenzaldehyde

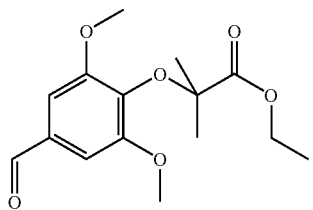

This compound was synthesized from 3,5-dimethyloxy-4-hydroxyabenzaldehyde and ethyl bromoisobutyrate according to general method 4 described earlier.

Purification was by silica gel chromatography (elution: cyclohexane/ethyl acetate 8:2).

1H NMR CDCl$_3$ δ ppm: 1.33 (t, J=7.29 Hz, 3H), 1.50 (s, 6H), 3.84 (s, 6H), 4.27 (q, J=7.29 Hz, 2H), 7.08 (s, 2H), 9.86 (s, 1H)

Starting material 6

3,5-dimethyl-4-ethyloxycarbonyldimethylmethyloxybenzaldehyde

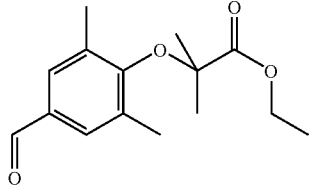

This compound was synthesized from 3,5-dimethyl-4-hydroxyabenzaldehyde and ethyl bromoisobutyrate according to general method 4 described earlier.

Purification was by silica gel chromatography (elution: cyclohexane/ethyl acetate 95:5).

1H NMR CDCl$_3$ δ ppm :1.37 (t, J=7.14 Hz, 3H), 1.50 (s, 6H), 2.29 (s, 6H), 4.30 (q, J=7.14 Hz, 2H), 7.54 (s, 2H), 9.88 (s, 1H)

Starting material 7

3-Ethyloxycarbonyldimethylmethyloxybenzaldehyde

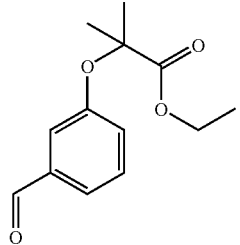

This compound was synthesized from 3-hydroxybenzaldehyde and ethyl bromoisobutyrate according to general method 4 described earlier.

Purification was by silica gel chromatography (elution: cyclohexane/ethyl acetate 9:1).

1H NMR CDCl$_3$ δ ppm: 1.24 (t, J=7.27 Hz, 3H), 1.62 (s, 6H), 4.25 (q, J=7.27 Hz, 2H), 7.11 (m, 1H), 7.31 (m, 1H), 7.40 (t, J=8.19 Hz, 1H), 7.49 (m, 1H), 9.93 (s, 1H).

Starting material 8

4-Ethyloxycarbonyldimethylmethyl thiobenzaldehyde

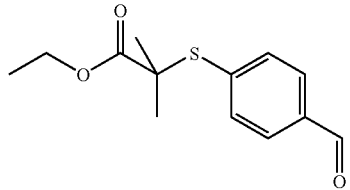

4-Methylthiobenzaldehyde (1 eq) was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum evaporation.

The evaporation residue was taken up in acetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate and vacuum evaporated.

The resulting 4-mercaptobenzaldehyde intermediate was used without further purification. It was alkylated according to general method 4 to yield 4-ethyloxycarbonyldimethylmethylthiobenzaldehyde.

Purification was by silica gel chromatography (elution: cyclohexane/ethyl acetate 9:1).

1H NMR CDCl$_3$ δ ppm: 1.22 (t, J=7.46 Hz, 3H), 2.60 (s, 6H), 4.15 (q, J=7.46 Hz, 2H), 7.53 (d, J=8.38 Hz, 2H), 7.88 (d, J=8.39 Hz, 2H), 9.99 (s, 1H)

Reference: Young N R, Gauthier J Y., Coombs W. (1984). Tetrahedron Letters 25(17): 1753-1756.

Starting Material 9

4'-Ethyloxycarbonyldimethylmethyloxyacetophenone

This compound was synthesized from 4'-hydroxyacetophenone and ethyl bromoisobutyrate according to general method 4 described earlier.

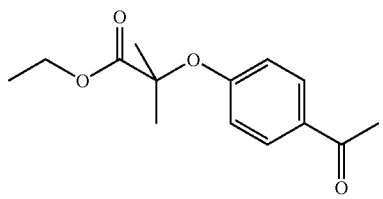

Purification was by silica gel chromatography (elution: cyclohexane/ethyl acetate 9:1).

1H NMR CDCl$_3$ δ ppm: 1.17 (t, J=5.64 Hz, 3H), 1.61 (s, 6H), 2.50 (s, 3H), 4.18 (q, J=5.64 Hz, 2H), 6.78 (d, J=8.82 Hz, 2H), 7.83 (d, J=8.81 Hz, 2H).

Starting material 10

3-bromophenyl acetate

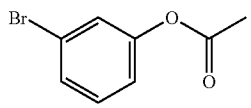

3-bromophenol was dissolved in dichloromethane. Triethylamine (1 eq) and acetic anhydride (2 eq) were added and the mixture was stirred at room temperature for 5 hours. The solvent was eliminated by vacuum evaporation. The evaporation residue was taken up in dichloromethane then dried on magnesium sulfate. The solvent was eliminated by vacuum evaporation.

Purification was by silica gel chromatography (elution: cyclohexane/ethyl acetate 95:5).

1H NMR CDCl$_3$ δ ppm: 2.30 (s, 3H), 7.0-7.4 (m, 4H)

Starting Material 11

2'-hydroxy-4'-bromoacetophenone

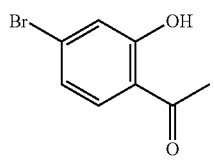

3-bromophenyl acetate (starting material 10) was mixed with aluminium chloride (3 eq), and the mixture was heated at 200° C. for 1 hour. The reaction medium was cooled to room temperature then poured in ice. The aqueous phase was extracted with methylene chloride which was dried on magnesium sulfate.

Purification was by silica gel chromatography (elution: cyclohexane/ethyl acetate 95:5).

1H NMR CDCl$_3$ δ ppm: 2.59 (s, 3H), 7.01 (d, J=8.5 Hz, 1H), 7.13 (s, 1H), 7.55 (d, J=8.5 Hz, 1H), 12.33 (s, 1H)

Starting material 12

4'-Ethyloxycarbonyldimethylmethylthiocetophenone

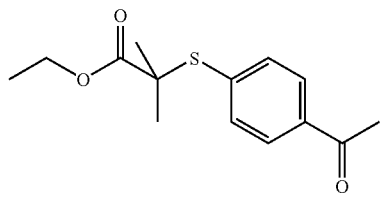

4'-methylthioacetophenone was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum The evaporation residue was taken up in acetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate then vacuum evaporated.

The resulting 4-mercaptoacetophenone intermediate was used without further purification. It was alkylated according to general method 4 to yield 4-ethyloxycarbonyldimethylmethylthioacetophenone.

Purification was by silica gel chromatography (elution: cyclohexane/ethyl acetate 9:1).

Reference: Young N R, Gauthier J Y., Coombs w (1984). Tetrahedron Letters 25(17): 1753-1756.

1H NMR CDCl$_3$ δ ppm: 1.21 (t, J=7.32 Hz, 3H), 1.51 (s, 6H), 2.59 (s, 3H), 4.12 (q, J=7.32 Hz, 2H), 7.51 (d, J=8.40 Hz, 2H), 7.79 (d, J=8.40 Hz, 2H)

Synthesis of Intermediate Compounds used to Synthesize the Inventive Compounds

Intermediate Compound 1

1-[4-chlorophenyl]-3-[3,5-dimethyl-4-hydroxyphenyl]prop-2-en-1-one

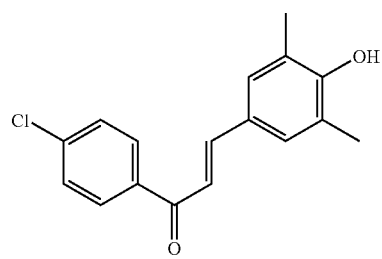

This compound was synthesized from 4-chloroacetophenone and 3,5-dimethyl-4-hydroxybenzaldehyde according to general method 1 described earlier.

Purification was by chromatography on silica gel (elution: cyclohexane/ethyl acetate 95:5).

1H NMR CDCl$_3$ δ ppm: 2.30 (s, 6H), 7.32 (s, 2H), 7.34 (d, J=15.25 Hz, 1H), 7.47 (d, J=8.86 Hz, 2H), 7.75 (d, J=15.26 Hz, 1H), 7.97 (d, J=8.86 Hz, 2H).

Intermediate Compound 2

1-[4-methylthiophenyl]-3-[3,5-dimethyl-4-hydroxyphenyl]prop-2-en-1-one

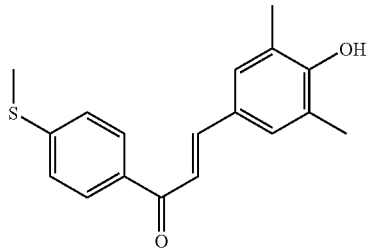

This compound was synthesized from 4'-methylthioacetophenone and 3,5-dimethyl-4-hydroxybenzaldehyde according to general method 1 described earlier.

Purification was by chromatography on silica gel (elution: cyclohexane/ethyl acetate 8:2).

1H NMR DMSO δ ppm: 2.22 (s, 6H), 2.54 (s, 3H), 7.36 (d, J=8.20 Hz, 2H), 7.48 (s, 2H), 7.62 (d, J=15.7 Hz, 1H), 7.74 (d, J=15.7 Hz, 1H), 8.10 (d, J=8.20 Hz, 2H), 8.92 (s, 1H)

Intermediate Compound 3

1-[2-methoxyphenyl]-3-[3,5-dimethyl-4-hydroxyphenyl]prop-2-en-1-one

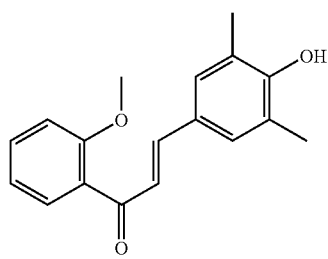

This compound was synthesized from 2'-methoxyacetophenone and 3,5-dimethyl-4-hydroxybenzaldehyde according to general method 1 described earlier.

Purification was by chromatography on silica gel (elution: cyclohexane/ethyl acetate 8:2).

1H NMR DMSO δ ppm: 2.39 (s, 6H), 2.22 (s, 6H), 7.58 (s, 2H), 7.67-7.62 (m, 3H), 7.82 (d, J=15.5 Hz, 1H), 8.17 (d, 1H), 12.96 (s, 1H)

Intermediate Compound 4

1-[4-hexyloxyphenyl]-3-[3,5-dimethyl-4-hydroxyphenyl]prop-2-en-1-one

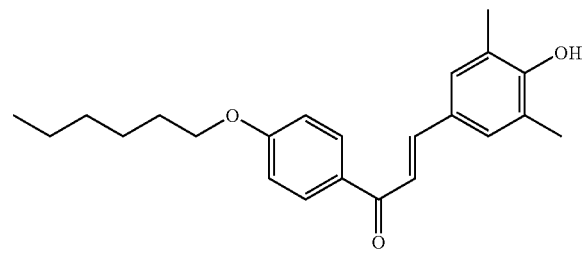

This compound was synthesized from 4-hexyloxyacetophenone and 3,5-dimethyl-4-hydroxybenzaldehyde according to general method 1 described earlier.

The expected compound precipitated in the reaction medium; it was dried and used without further purification for the following reaction.

1H NMR DMSO δ ppm: 0.88 (m, 3H), 1.28-1.43 (m, 6H), 1.72 (m, 2H), 2.21 (s, 6H), 4.05 (t, J=6.42 Hz, 2H), 7.40 (d, J=8.43 Hz, 2H), 7.48 (s, 2H), 7.57 (d, J=15.24 Hz, 1H), 7.72 (d, J=15.24 Hz, 1H), 8.12 (d, J=8.43 Hz, 2H), 8.89 (s, 1H)

Intermediate Compound 5

1-[2-hydroxy-4-chlorophenyl]-3-[3,5-dimethyl-4-hydroxyphenyl]prop-2-en-1-one

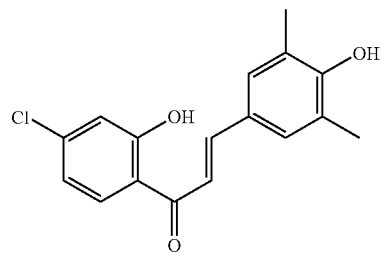

This compound was synthesized from 4'-chloro-2'-hydroxyacetophenone (starting material 3) and 3,5-dimethyl-4-hydroxybenzaldehyde according to general method 1 described earlier.

Purification was by chromatography on silica gel (toluene: 10).

1H NMR DMSO δppm: 2.21 (s, 6H), 7.1 (m, 2H), 7.55 (s, 2H), 7.72 (d, J=15.4 Hz, 1H), 7.80 (d, J=15.4 Hz, 1H), 8.25 (d, J=9.0 Hz, 1H), 9.09 (s, 1H), 13.04 (s, 1H)

Intermediate Compound 6

2-(3,5-dimethyl-4-hydroxyphenyl)-7-chloro-4H-1-benzopyran-4-one

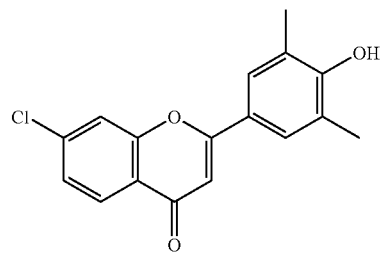

This compound was synthesized from 1-[2-hydroxy-4-chlorophenyl]-3-[3,5-dimethyl-4-hydroxyphenyl]prop-2-en-1-one (intermediate compound 5) according to the following method:

1-[2-hydroxy-4-chlorophenyl]-3-[3,5-dimethyl-4-hydroxyphenyl]prop-2-en-1-one was dissolved in dimethylsulfoxide, an iodine crystal was added, and the mixture was kept under reflux for 10 min The reaction medium was brought to room temperature, hydrolyzed. The precipitate was dried, rinsed with sodium thiosulfate solution then with water.

Purification was by dissolution in methylene chloride and precipitation by addition of heptane.

1H NMR DMSO δppm: 2.25 (s, 6H), 6.87 (s, 1H), 7.51 (d, J=8.55 Hz, 1H), 7.73 (s, 2H), 7.98 (m, 2H)

Reference: Doshi A G, S. P., Ghiya B J (1986). Indian J Chem Sect B 25: 759.

Intermediate Compound 7

1-[2-methyloxy-4-chlorophenyl]-3-[3,5-dimethyl-4-hydroxydimethylmethyloxyphenyl]prop-2-en-1-one

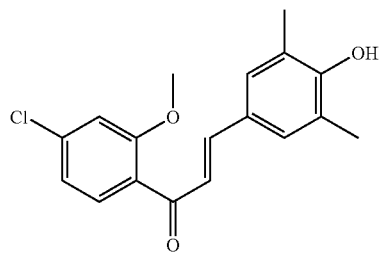

This compound was synthesized from 4'-chloro-2'-methoxyacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 2.21 (s, 6H), 3.90 (s, 3H), 7.12 (m, 1H), 7.23 (d, J=15.5 Hz, 1H), 7.29 (s, J=1.80 Hz, 1H), 7.38 (d, J=15.5 Hz, 1H), 7.41 (s, 2H), 7.48 (d, J=7.98 Hz, 1H)

Intermediate Compound 8

1-[4-bromophenyl]-3-[3,5-dimethyl-4-hydroxyphenyl]prop-2-en-1-one

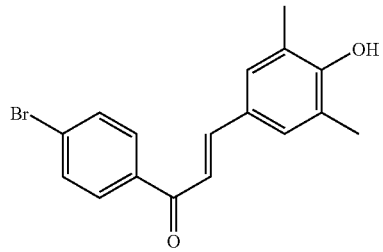

This compound was synthesized from 4'-bromoacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 2.30 (s, 6H), 7.32 (s, 2H), 7.56-7.66 (m, 3H), 7.75 (d, J=15.27 Hz, 1H), 7.90 (d, J=8.70 Hz, 2H), 9.82 (s, 1H)

Intermediate Compound 9

1-[4-heptylphenyl]-3-[3,5-dimethyl-4-hydroxyphenyl]prop-2-en-1-one

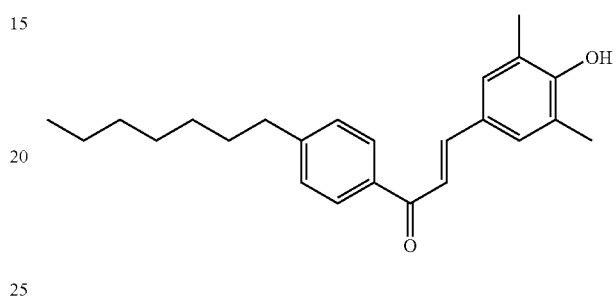

This compound was synthesized from 4'-heptylacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 0.84 (m, 3H), 1.25 (m, 8H), 1.60 (m, 2H), 2.21 (s, 6H), 2.65 (t, J=7.50 Hz, 2H), 7.35 (d, J=8.02 Hz, 2H), 7.48 (s, 2H), 7.60 (d, J=15.48 Hz, 1H), 7.71 (d, J=15.48 Hz, 1H), 8.05 (d, J=8.02 Hz, 2H), 8.92 (s, 1H)

Synthesis of the Inventive Compounds

Compound 1

1-[2-hydroxy-4-ethoxycarbonyldimethylmethyloxyphenyl]-3-[3,5-ditertbutyl-4-hydroxyphenyl]prop-2-en-1-one

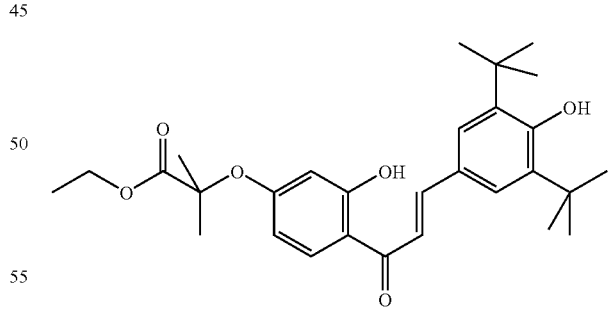

This compound was synthesized from 2'-hydroxy-4'-(ethoxycarbonyldimethylmethoxy)acetophenone (starting material 1) and 3,5-ditertbutyl-4-hydroxybenzaldehyde according to general method 1 described earlier.

Purification was by chromatography on silica gel (elution: cyclohexane/ethyl acetate 9:1).

1H NMR CDCl$_3$ δ ppm: 1.25 (t, J=7.11 Hz, 3H), 1.45 (s, 18H), 1.70 (s, 6H), 4.26 (q, J=7.11 Hz, 2H), 5.63 (s, 1H), 6.33 (d, J=2.37 Hz, 1H), 6.42 (dd, J=8.8 Hz, J=2.37 Hz, 1H), 7.41

(d, J=15.39 Hz, 1H), 7.5 (s, 2H), 7.83 (d, J=8.8 Hz, 1H), 7.88 (J=15.39 Hz, 1H), 13.5 (s, 1H)

Compound 2

1-[2-hydroxy-4-carboxydimethylmethyloxyphenyl]-3-[3,5-ditertbutyl-4-hydroxyphenyl]prop-2-en-1-one

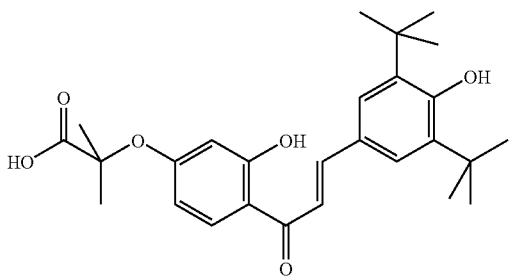

This compound was synthesized from 1-[2-hydroxy-4-ethoxycarbonyldimethylmethyloxyphenyl]-3-[3,5-ditertbutyl-4-hydroxyphenyl]prop-2-en-1-one (compound 1) according to the following method:

The ester was dissolved in ethanol, an aqueous 1N sodium hydroxide solution (5 eq) was added, and the mixture was kept under reflux for 10 hours. The medium was acidified by addition of 12 N hydrochloric acid then extracted with ethyl acetate. The organic phase was dried on magnesium sulfate then vacuum evaporated.

Purification was by preparative HPLC (reverse phase RP18, Licrospher 12 μm, elution:water-methanol-trifluoroacetic acid: 22:78:0.1).

1H NMR CDCl$_3$ δ ppm: 1.49 (s, 18H), 1.73 (s, 6H), 5.62 (s, 1H), 6.44 (d, J=15.5 Hz, 1H), 7.01 (m, 2H), 7.57 (t, 1H), 7.81 (d, J=15.5 Hz, 1H), 7.87 (d, 2H), 7.93 (d, 1H), 8.26 (d, 1H)

MS (ES-MS): 453.2 (M−1)

Compound 3

1-[2-hydroxy-4-chlorophenyl]-3-[4-carboxydimethylmethyloxyphenyl]prop-2-en-1-one

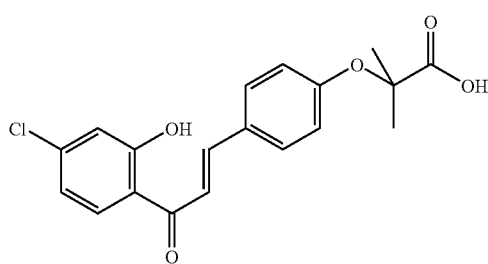

This compound was synthesized from 2'-hydroxy-4'-chloroacetophenone and 4-ethyloxycarbonyldimethylmethyloxybenzaldehyde (starting material 9) according to general method 2 described earlier.

Purification was by chromatography on silica gel (elution: cyclohexane/ethyl acetate 9:1).

1H NMR DMSO δ ppm: 1.58 (s, 6H), 6.87 (d, J=8.54 Hz, 2H), 7.05 (dd, J=8.54 Hz, 1.83 Hz, 1H), 7.09 (d, J=1.2 Hz, 1H), 7.90-7.80 (m, 4H), 8.25 (m, 8.52 Hz, 1H), 12.84 (s, 1H), 13.26 (s, 1H)

MS (ES-MS): 359.0 (M−1)

Compound 4

1-[2-hydroxyphenyl]-3-[4-carboxydimethylmethyloxyphenyl]prop-2-en-1-one

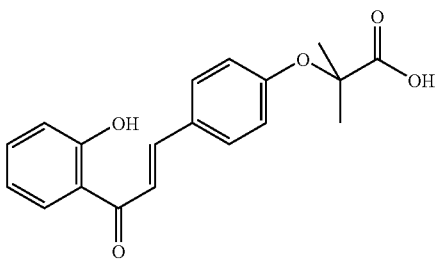

This compound was synthesized from 2'-hydroxyacetophenone and 4-ethyloxycarbonyldimethylmethyloxybenzaldehyde (starting material 4) according to general method 2 described earlier.

Purification was carried out by chromatography on silica gel (elution:cyclohexane/ethyl acetate 9:1).

1H NMR DMSO δ ppm: 1.58 (s, 6H), 6.88 (d, 2H), 7.01 (m, 2H), 7.57 (t, 1H), 7.81 (d, J=15.5 Hz, 1H), 7.87 (d, 2H), 7.93 (d, J=15.5 Hz, 1H), 8.26 (d, 1H), 12.69 (s, 1H)

MS (ES-MS): 325.1 (M−1)

Compound 5

1-[2-hydroxyphenyl]-3-[3,5-dimethoxy-4-carboxydimethylmethyloxyphenyl]prop-2-en-1-one

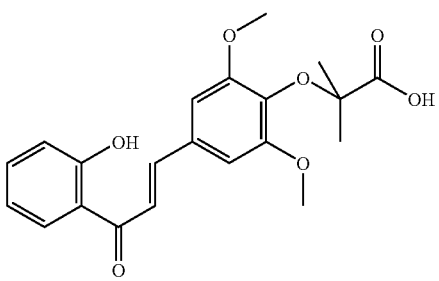

This compound was synthesized from 2'-hydroxyacetophenone and 3,5-dimethyloxy-4-ethyloxycarbonyldimethylmethyloxybenzaldehyde (starting material 5) according to general method 2 described earlier. Purification was carried out by chromatography on silica gel (elution:cyclohexane/ethyl acetate 9:1).

1H NMR DMSO δ ppm: 1.35 (s, 6H), 3.80 (s, 6H), 7.00-7.03 (m, 2H), 7.25 (s, 2H), 7.59 (t, 1H, J=8.07 Hz, 1H), 7.81 (d, J=15.5 Hz, 1H), 8.00 (d, J=15.5 Hz, 1H), 8.31 (d, J=8.07 Hz, 1H), 12.36 (s, 1H), 12.69 (s, 1H)

MS (ES-MS): 385.3 (M−1)

Compound 6

1-[2-hydroxy-4-chlorophenyl]-3-[3,5-dimethoxy-4-carboxydimethylmethyloxyphenyl]prop-2-en-1-one

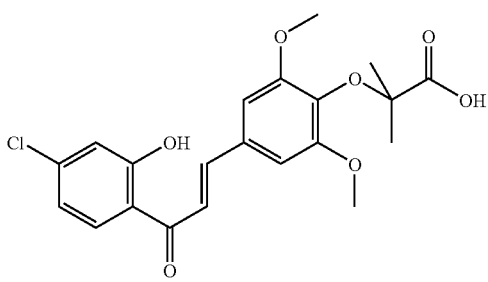

This compound was synthesized from 2'-hydroxy-4'-chloroacetophenone (starting material 3) and 3,5-dimethyloxy-4-ethyloxycarbonyldimethylmethyloxybenzaldehyde (starting material 5) according to general method 2 described earlier.

Purification was carried out by chromatography on silica gel (elution:cyclohexane/ethyl acetate 9:1).

1H NMR DMSO δ ppm: 1.34 (s, 6H), 3.80 (s, 6H), 7.08 (dd, J=1.77 Hz, 1H), 7.12 (d, J=1.77 Hz, 1H), 7.24 (s, 2H), 7.79 (d, J=15.4 Hz, 1H), 7.93 (d, J=15.4 Hz, 1H), 8.27 (d, J=8.3 Hz, 1H), 12.36 (s, 1H), 12.69 (s, 1H)

MS (ES-MS): 419.0 (M−1)

Compound 7

1-[2-hydroxy-4-chlorophenyl]-3-[3,5-dimethyl-4-carboxydimethylmethyloxyphenyl]prop-2-en-1-one

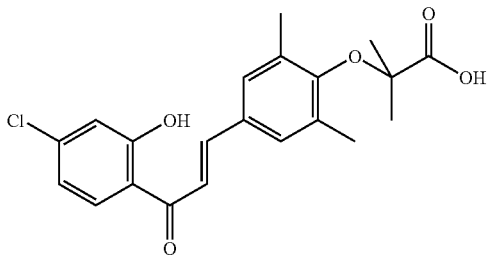

This compound was synthesized from 2'-hydroxy-4'-chloroacetophenone (starting material 3) and 3,5-dimethyl-4-ethyloxycarbonyldimethylmethyloxybenzaldehyde (starting material 6) according to general method 2 described earlier.

Purification was carried out by chromatography on silica gel (elution:cyclohexane/ethyl acetate 9:1).

1H NMR DMSO δ ppm: 1.39 (s, 6H), 2.22 (s, 6H), 7.07 (m, 1H), 7.12 (d, J=2.07 Hz, 1H), 7.61 (s, 2H), 7.74 (d, J=15.5 Hz, 1H), 7.87 (d, J=15.5 Hz, 1H), 8.26 (d, 1H), 12.76 (s, 1H)

MS (ES-MS): 387.1 (M−1)

Compound 8

1-[2-hydroxy-4-carboxydimethylmethyloxyphenyl]-3-[3,5-dibromo-4-hydroxyphenyl]prop-2-en-1-one

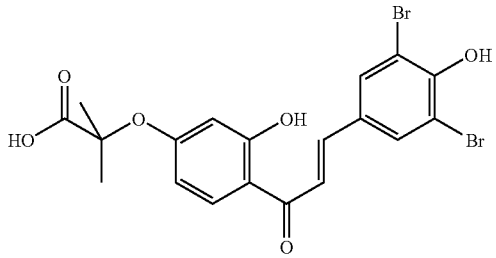

This compound was synthesized from 2'-hydroxy-4'-ethyloxycarbonyldimethylmethyloxyacetophenone (starting material 1) and 3,5-dibromo-4-hydroxybenzaldehyde according to general method 2 described earlier.

Purification was carried out by chromatography on silica gel (elution:cyclohexane/ethyl acetate 9:1).

1H NMR CDCl₃ δ ppm: 1.60 (s, 6H), 6.24 (d, J=2.47 Hz, 1H), 6.43 (dd, J=2.47 Hz, J=8.52 Hz, 1H), 7.70 (d, J=15.5 Hz, 1H), 7.96 (d, J=15.5 Hz, 1H), 8.22 (s, 2H), 8.34 (d, J=9.16 Hz, 1H), 13.34 (s, 1H)

MS (ES-MS): 498.6 (M−1)

Compound 9

1-[2-hydroxyphenyl]-3-[3-carboxydimethylmethyloxyphenyl]prop-2-en-1-one

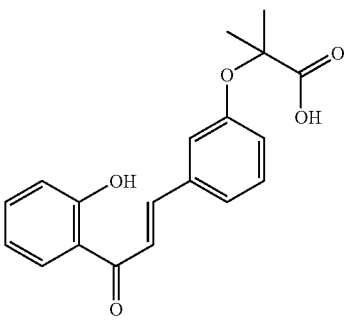

This compound was synthesized from 2'-hydroxyacetophenone and 3-ethyloxycarbonyldimethylmethyloxybenzaldehyde (starting material 7) according to general method 2 described earlier.

Purification was carried out by chromatography on silica gel (elution:cyclohexane/ethyl acetate 9:1).

1H NMR DMSO δ ppm: 1.56 (s, 6H), 6.91 (dd, J=8.01 Hz, J=2.47 Hz, 1H), 7.03-6.99 (m, 2H), 7.41-7.36 (m, 2H), 7.60-7.52 (m, 2H), 7.77 (d, J=15.5 Hz, 1H), 8.00 (d, J=15.5 Hz, 1H), 8.31 (dd, J=8.63 Hz, J=1.85 Hz, 1H), 12.47 (s, 1H), 13.17 (s, 1H)

MS (ES-MS): 325.8 (M−1)

Compound 10

1-[2-hydroxy-4-carboxydimethylmethyloxyphenyl]-3-[3-hydroxyphenyl]prop-2-en-1-one

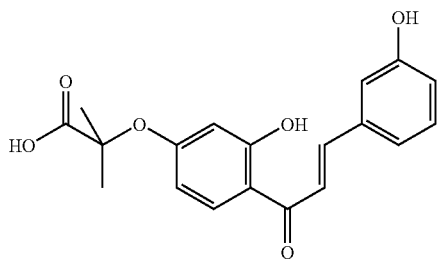

This compound was synthesized from 2'-hydroxy-4'-ethyloxycarbonyl dimethylmethyloxyacetophenone (starting material 1) and 3-hydroxybenzaldehyde according to general method 2 described earlier.

Purification was carried out by chromatography on silica gel (elution : cyclohexane/ethyl acetate 9:1).

1H NMR DMSO δ ppm: 1.60 (s, 6H), 6.25 (d, J=2.47 Hz, 1H), 6.43 (dd, J=2.47 Hz, 9.09 Hz, 1H), 6.89 (m, 1H), 7.35-7.24 (m, 3H), 7.73 (d, 1H), 7.92 (d, J=15.5 Hz, 1H), 8.27 (d, J=15.5 Hz, 1H), 13.21 (s, 1H), 13.39 (s, 1H).

MS (ES-MS): 341(M−1)

Compound 11

1-[2-hydroxyphenyl]-3-[3,5-dimethyl-4-carboxydimethylmethyloxyphenyl]prop-2-en-1-one

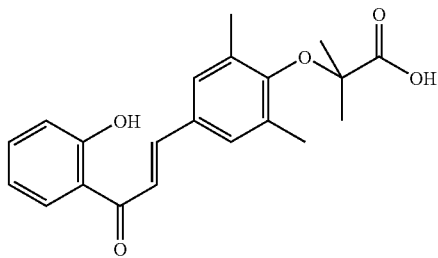

This compound was synthesized from 2'-hydroxyacetophenone and 3,5-dimethyl-4-ethyloxycarbonyldimethylmethyloxybenzaldehyde (starting material 6) according to general method 2 described earlier.

Purification was carried out by chromatography on silica gel (elution:cyclohexane/ethyl acetate: 9/1) followed by preparative HPLC (reverse phase RP18, Licrospher 12 µm, elution: water/methanol/trifluoroacetic acid: 22/78/0.1).

1H NMR DMSO δ ppm: 1.57 (s, 6H), 2.31 (s, 6H), 6.96 (t, J=8.17 Hz, 1H), 7.04 (d, J=8.72 Hz, 1H), 7.35 (s, 2H), 7.49 (t, J=8.2 Hz, 1H), 7.58 (d, J=15.8 Hz, 1H), 7.84 (d, J=15.8 Hz, 1H), 7.94 (d, J=8.7 Hz, 1H), 12.87 (s, 1H)

MS (ES-MS): 353.1 (M−1)

Compound 12

1-[2-hydroxy-4-carboxydimethylmethyloxyphenyl]-3-[4-methylthiophenyl]prop-2-en-1-one

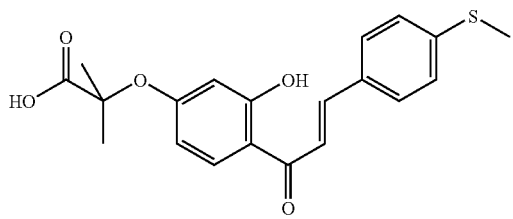

This compound was synthesized from 2'-hydroxy-4'-ethyloxycarbonyldimethylmethyloxyacetophenone (starting material 1) and 4-methylthiobenzaldehyde according to general method 2 described earlier.

Purification was by chromatography on silica gel (elution: cyclohexane/ethyl acetate 9/1) followed by preparative HPLC (reverse phase RP18, Licrospher 12 µm, elution: water/methanol/trifluoroacetic acid: 22/78/0.3).

1H NMR DMSO δ ppm: 1.60 (s, 6H), 2.54 (s, 3H), 6.25 (d, 1H), 6.43 (dd, J=2.47 Hz, 1H), 7.33 (d, J=8.56 Hz, 2H), 7.8 (d, 15.5 Hz, 1H), 7.86 (d, J=8.56 Hz, 2H), 7.98 (d, J=15.5 Hz, 1H), 8.29 (d, J=9.1 Hz, 1H), 13.34 (s, 1H)

MS (ES-MS): 373.1 (M−1)

Compound 13

1-[2,4-dihydroxyphenyl]-3-[4-carboxydimethylmethyloxyphenyl]prop-2-en-1-one

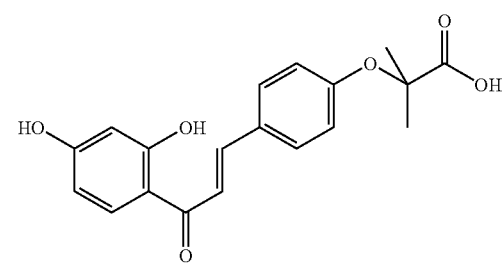

This compound was synthesized from 2',4'-dihydroxyacetophenone and 4-ethoxycarbonyldimethylmethyloxybenzaldehyde (starting material 4) according to general method 2 described earlier.

Purification was by chromatography on silica gel (elution: cyclohexane/ethyl acetate 9/1) followed by preparative HPLC (reverse phase RP18, Licrospher 12 µm, elution:water/methanol/trifluoroacetic acid: 34/66/0.1).

1H NMR DMSO δ ppm: 1.57 (s, 6H), 6.29 (d, J=2.16 Hz, 1H), 6.41 (dd, J=9.18 Hz, J=2.16 Hz, 1H), 6.86 (d, J=8.64 Hz, 2H), 7.75 (d, J=15.67 Hz, 1H), 7.83-7.88 (m, 3H), 8.19 (d, J=9.18 Hz, 1H), 10.74 (s, 1H), 13.53 (s, 1H)

MS (maldi-Tof): 343.1 (M+1)

Compound 14

1-[2-hydroxyphenyl]-3-[4-carboxydimethylmethyl oxyphenyl]prop-2-en-1-one

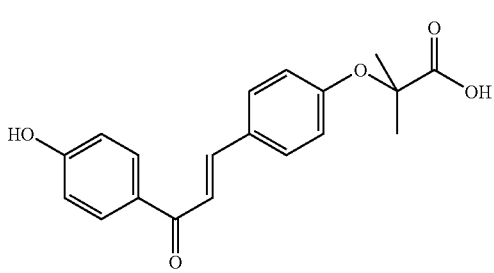

This compound was synthesized from 4'-hydroxyacetophenone and 4-ethoxycarbonyldimethylmethyloxybenzaldehyde (starting material 4) according to general method 2 described earlier.

Purification was carried out by chromatography on silica gel (elution: cyclohexane/ethyl acetate 9:1) followed by preparative HPLC (reverse phase RP18, Licrospher 12 μm, elution:water/methanol/trifluoroacetic acid: 34/66/0.1).

1H NMR DMSO δ ppm: 1.56 (s, 6H), 6.85 (d, J=8.63 Hz, 2H), 6.90 (d, J=9.21 Hz, 2H), 7.63 (d, J=15.54 Hz, 1H), 7.78 (m, 3H), 8.05 (d, J=8.61 Hz, 2H), 10.40 (s, 1H), 13.22 (s, 1H)<

MS (maldi-Tof): 327.1 (M+1)

Compound 15

1-[4-chlorophenyl]-3-[3,5-dimethyl-4-isopronyloxy-carbonyldimethylmethyloxyphenyl]prop-2-en-1-one

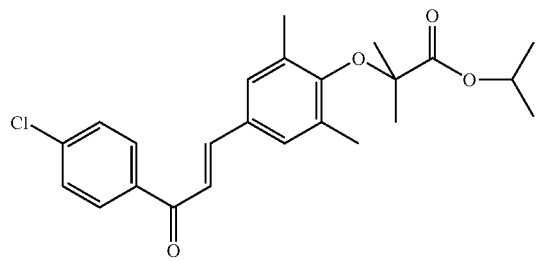

This compound was synthesized from 1-[4-chlorophenyl]-3-[3,5-dimethyl-4-hydroxyphenyl]prop-2-en-1-one (intermediate compound 1) and isopropyl bromoisobutyrate according to general method 4 described earlier.

Purification was carried out by chromatography on silica gel (elution:cyclohexane/ethyl acetate 9/1).

1H NMR DMSO δ ppm: 1.25 (d, J=6.06 Hz, 6H), 1.39 (s, 6H), 5.00 (sept, J=6.06 Hz, 1H), 7.57 (s, 2H), 7.62 (d, J=8.40 Hz, 2H), 7.64 (d, J=15.8 Hz, 1H), 7.81 (d, J=15.8 Hz, 1H), 8.16 (d, J=8.40 Hz, 2H).

MS (Maldi-Tof): 415.1 (M+1)

Compound 16

1-[4-chlorophenyl]-3-[3,5-dimethyl-4-tertbutyloxy-carbonyldimethylmethyloxyphenyl]prop-2-en-1-one

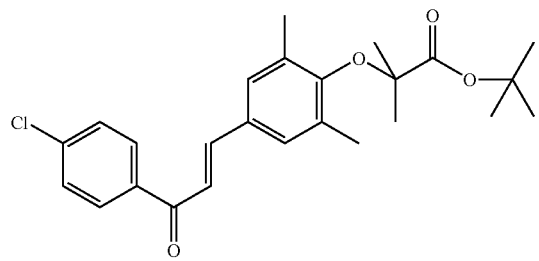

This compound was synthesized from 1-[4-chlorophenyl]-3-[3,5-dimethyl-4-hydroxyphenyl]prop-2-en-1-one (intermediate compound 1) and tertbutyl bromoisobutyrate according to general method 4 described earlier.

Purification was by chromatography on silica gel (elution: cyclohexane/ethyl acetate 9/1).

Compound 17

1-[4-chlorophenyl]-3-[3,5-dimethyl-4-carboxydimethylmethyloxyphenyl]prop-2-en-1-one

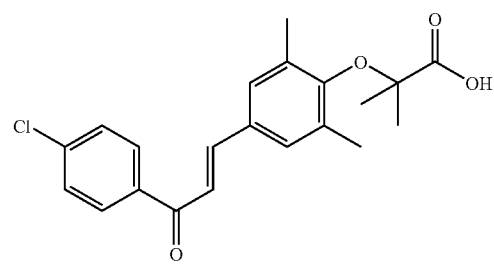

This compound was synthesized from 1-[4-chlorophenyl]-3-[3,5-dimethyl-4-tertbutyloxycarbonyldimethyl-methyloxyphenyl]prop-2-en-1-one (compound 16) according to general method 5 described earlier.

Purification was carried out by chromatography on silica gel (elution: dichloromethane/methanol 98/2)

1H NMR DMSO δ ppm: 1.39 (s, 6H), 2.22 (s, 6H), 7.58 (s, 2H), 7.67-7.62 (m, 3H), 7.82 (d, J=15.5 Hz, 1H), 8.17 (d, 1H), 12.96 (s, 1H)

MS (Maldi-Tof): 373.3 (M+1)

Compound 18

1-[2-hydroxy-4-carboxydimethylmethyloxyphenyl]-3-[4-chlorophenyl]prop-2-en-1-one

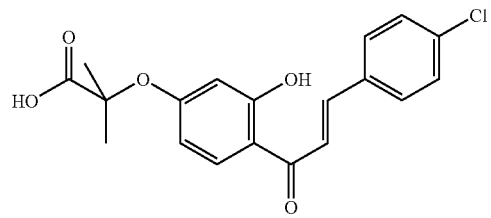

This compound was synthesized from 2'-hydroxy-4'-ethyloxycarbonyldimethylmethyloxyacetophenone (starting material 1) and 4-chlorobenzaldehyde according to general method 2 described earlier.

Purification was by chromatography on silica gel (elution: cyclohexane/ethyl acetate 9:1) followed by preparative HPLC (reverse phase RP18, Licrospher 12 μm, elution:water/methanol/trifluoroacetic acid: 22/78/0.1).

1H NMR DMSO δ ppm: 1.60 (s, 6H), 6.25 (d, J=2.47 Hz, 1H), 6.45 (dd, J=2.47 Hz, J=9.12 Hz, 1H), 6.55 (d, J=8.55 Hz, 2H), 7.82 (d, J=15.54 Hz, 1H), 7.97 (d, J=8.55 Hz, 2H), 8.03 (d, J=15.54 Hz, 1H), 8.29 (d, J=9.12 Hz, 1H), 13.20 (s, 1H), 13.39 (s, 1H)

MS (ES-MS): 359.0 (M−1)

Compound 19

1-[2-hydroxyphenyl]-3-[4-carboxydimethyimethylthiophenyl]prop-2-en-1-one

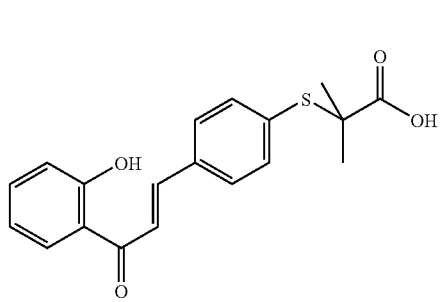

This compound was synthesized from 2'-hydroxyacetophenone and ethyloxycarbonyldimethylmethylthiobenzaldehyde (starting material 8) according to general method 2 described earlier.

Purification was by chromatography on silica gel (elution: dichloromethane/methanol 95/5) followed by preparative HPLC (reverse phase RP18, Licrospher 12 μm, elution:water/methanol/trifluoroacetic acid: 22/78/0.1).

1H NMR DMSO δ ppm: 1.44 (s, 6H), 6.99-7.05 (m, 1H), 7.52 (d, J=8.1 Hz, 2H), 7.58 (m, 1H), 7.83 (d, J=15.5 Hz, 1H), 7.92 (d, J=8.1 Hz, 1H), 8.09 (d, J=15.5 Hz, 1H), 8.26 (dd, J=1.62, J=8.6 Hz, 1H), 12.47 (s, 1H), 12.78 (s, 1H)

MS (Maldi-Tof): 242.9 (M+1)

Compound 20

1-[4-chloro-2-hydroxyphenyl]-3-[4-carboxydimethylmethylthiophenyl]prop-2-en-1-one

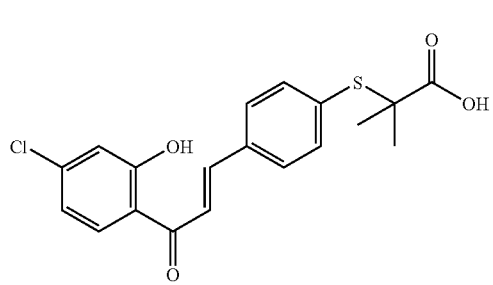

This compound was synthesized from 4'-chloro-2'-hydroxyacetophenone (starting material 3) and 4-ethyloxycarbonyldimethylmethylthiobenzaldehyde (starting material 8) according to general method 2 described earlier.

Purification was by chromatography on silica gel (elution: dichloromethane/methanol 95:5) followed by preparative HPLC (reverse phase RP18, Licrospher 12 μm, elution:water/methanol/trifluoroacetic acid: 22/78/0.1).

1H NMR DMSO δ ppm: 1.43 (s, 6H), 7.05 (dd, J=1.7 Hz, J=8.46 Hz, 1H), 7.11 (d, J=2.25 Hz, 1H), 7.51 (d, J=7.92 Hz, 2H), 7.82 (d, J=15.8 Hz, 1H), 7.89 (d, J=7.9 Hz, 2H), 8.05 (d, J=15.2 Hz, 1H), 8.23 (d, J=8.46 Hz, 1H), 12.57 (s, 1H), 12.78 (s, 1H)

MS (Maldi-Tof): 377.0 (M−1)

Compound 21

1-[4-carboxydimethylmethyloxyphenyl]-3-[3,5-dimethyl4-hydroxyphenyl]prop-2-en-1-one

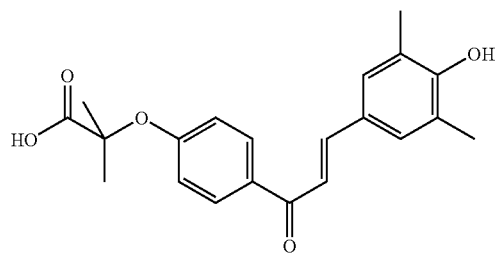

This compound was synthesized from 4-ethyloxycarbonyldimethylmethyloxy acetophenone (starting material 9) and 3,5-dimethyl-4-hydroxybenzaldehyde according to general method 2 described earlier.

Purification was by chromatography on silica gel (elution: dichloromethane/methanol 95:5) followed by preparative HPLC (reverse phase RP18, Licrospher 12 μm, elution:water/methanol/trifluoroacetic acid: 22/78/0.1).

1H NMR DMSO δ ppm: 1.60 (s, 6H), 2.21 (s, 6H), 6.91 (d, J=9.09 Hz, 2H), 7.48 (s, 2H), 7.57 (d, J=15.12 Hz, 1H), 7.70 (d, J=15.63 Hz, 1H), 8.09 (d, J=9.06 Hz, 2H), 8.9 (s, 1H), 13.29 (s, 1H)

MS (Maldi-Tof): 355.2 (M+1)

Compound 22

1-[4-methylthiophenyl]-3-[4-carboxydimethylmethyloxyphenyl]prop-2-en-1-one

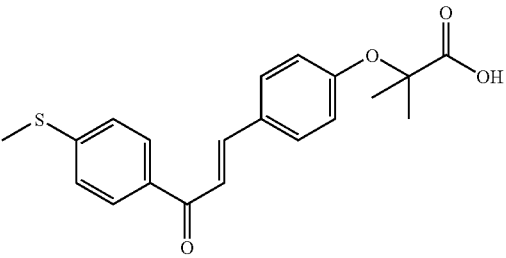

This compound was synthesized from 4'-methylthioacetophenone (starting material 12) and 4-ethyloxycarbonyldimethylmethyloxybenzaldehyde (starting material 9) according to general method 2 described earlier.

Purification was by chromatography on silica gel (elution: dichloromethane/methanol 95:5) followed by preparative HPLC (reverse phase RP18, Licrospher 12 μm, elution: water/methanol/trifluoroacetic acid: 22/78/0.1).

1H NMR DMSO δ ppm: 1.57 (s, 6H), 2.57 (s, 3H), 6.86 (d, J=8.94 Hz, 2H), 7.41 (d, J=8.40 Hz, 2H), 7.69 (d, J=15.2 Hz, 1H), 7.84-7.78 (m, 3H), 8.09 (d, J=8.4 Hz, 2H), 13.21 (s, 1H)

MS (Maldi-Tof): 357.2 (M+1)

Compound 23

1-[4-carboxydimethylmethyloxyphenyl]-3-[4-chlorophenyl]prop-2-en-1-one

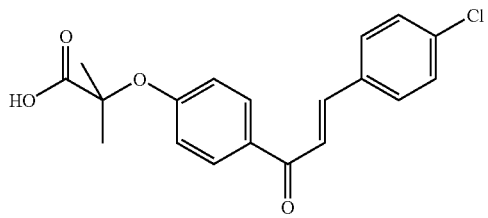

This compound was synthesized from 4-ethyloxycarbonyl dimethylmethyloxyacetophenone (starting material 9) and 4-chlorobenzaldehyde according to general method 3 described earlier.

Purification was by chromatography on silica gel (elution: dichloromethane/methanol 95:5) followed by preparative HPLC (reverse phase RP18, Licrospher 12 μm, elution: water/methanol/trifluoroacetic acid: 22/78/0.1).

1H NMR DMSO δ ppm: 1.72 (s, 6H), 6.97 (d, J=8.61 Hz, 2H), 7.39 (d, J=8.25 Hz, 2H), 7.50 (d, J=15.72 Hz, 1H), 7.57 (d, J=8.61 Hz, 2H), 7.77 (d, J=15.72 Hz, 1H), 7.99 (d, J=8.61 Hz, 2H), 13.30 (s, 1H)

MS (Maldi-Tof): 345.1 (M+1)

Compound 24

1-[4-carboxydimethylmethylthiophenyl]-3-[4-methylthiophenyl]prop-2-en-1-one

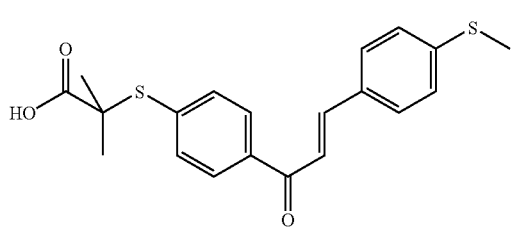

This compound was synthesized from 4-ethyloxycarbonyl dimethylmethylthioacetophenone (starting material 12) and 4-methylthiobenzaldehyde according to general method 3 described earlier.

Purification was by chromatography on silica gel (elution: dichloromethane/methanol 95:5) followed by preparative HPLC (reverse phase RP18, Licrospher 12 μm, elution: water/methanol/trifluoroacetic acid: 22/78/0.1).

1H NMR DMSO 5 ppm: 1.46 (s, 6H), 2.54 (s, 3H), 7.33 (d, J=8.61 Hz, 2H), 7.59 (d, J=8.10 Hz, 2H), 7.73 (d, J=15.66 Hz, 1H), 7.85 (d, J=8.10 Hz, 2H), 7.92 (d, J=15.66 Hz, 1H), 8.13 (d , 8.10 Hz, 2H), 12.85 (s, 1H)

MS (Maldi-Tof): 373.1 (M+1)

Compound 25

1-[2-hydroxy-4-bromophenyl]-3-[3,5-dimethyl-4-carboxydimethylmethyloxyphenyl]prop-2-en-1-one

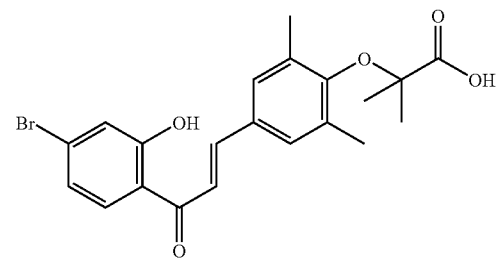

This compound was synthesized from 4'-bromo-2'-hydroxyacetophenone (starting material 11) and 3,5-dimethyl-4-ethyloxycarbonyldimethyloxybenzaldehyde (starting material 6) according to general method 2 described earlier.

Purification was by chromatography on silica gel (elution: dichloromethane/methanol 95:5) followed by preparative HPLC (reverse phase RP18, Licrospher 12 μm, elution: water/methanol/trifluoroacetic acid: 22/78/0.1).

1H NMR DMSO δ ppm: 1.39 (s, 6H), 2.22 (s, 6H), 7.20 (dd, J=2.16, J=8.55 Hz, 1H), 7.25 (d, J=1.59 Hz, 1H), 7.60 (s, 2H), 7.73 (d, J=15.51 Hz, 111), 7.86 (d, J=15.51 Hz, 1H), 8.16 (d, J=8.58 Hz, 1H), 12.70 (s, 1H), 13.30 (s, 1H)

MS (ES-MS): 432.9 (M−1)

Compound 26

1-[4-carboxydimethylmethyloxyphenyl]-3-[4-methylthiophenyl]prop-2-en-1-one

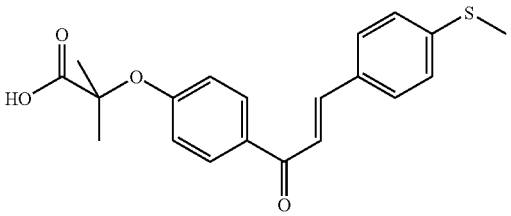

This compound was synthesized from 4'-ethyloxycarbonyldimethylmethyloxyacetophenone (starting material 9) and 4-methylthiobenzaldehyde according to general method 2 described earlier.

Purification was by chromatography on silica gel (elution: dichloromethane/methanol 95:5) followed by preparative HPLC (reverse phase RP18, Licrospher 12 μm, elution: water/methanol/trifluoroacetic acid: 22/78/0.1).

1H NMR DMSO 5 ppm: 1.60 (s, 6H), 2.53 (s, 3H), 6.93 (d, J=9.00 Hz, 2H), 7.32 (d, J=8.49 Hz, 2H), 7.68 (d, J=15.51 Hz, 1H), 7.82 (d, J=8.52 Hz, 2H), 7.89 (d, J=15.51 Hz, 1H), 8.13 (d, 9.00 Hz, 2H), 13.30 (s, 1H)

MS (Maldi-Tof): 355.0(M+1)

Compound 27

1-[4-methylthiophenyl]-3-[3,5-dimethyl-4-tertbutyloxycarbonyldimethylmethyloxyphenyl]prop-2-en-1-one

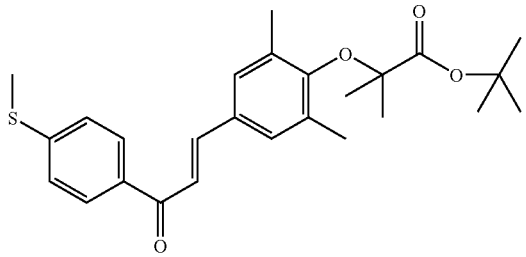

This compound was synthesized from 1-[4-methylthiophenyl]-3-[3,5-dimethyl-4-hydroxyphenyl]prop-2-en-1-one (intermediate compound 2) and tertbutyl bromoisobutyrate according to general method 4 described earlier. Purification was by chromatography on silica gel (elution: cyclohexane/ethyl acetate 8/2).

Compound 28

1-[4-methylthiophenyl]-3-[3,5-dimethyl-4-isopropyloxycarbonyldimethylmethyloxyphenyl]prop-2-en-1-one

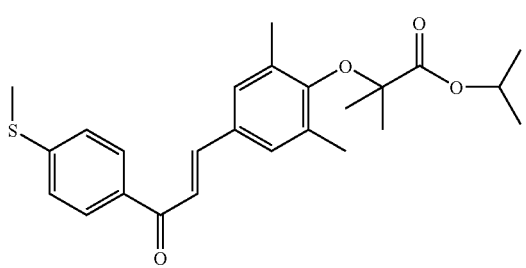

This compound was synthesized from 1-[4-methylthiophenyl]-3-[3,5-dimethyl-4-hydroxyphenyl]prop-2-en-1-one (intermediate compound 2) and isopropyl bromoisobutyrate according to general method 4 described earlier.

Purification was by chromatography on silica gel (elution: cyclohexane/ethyl acetate 9/1).

1H NMR DMSO δ ppm: 1.25 (d, J=6.18 Hz, 6H), 1.39 (s, 6H), 2.18 (s, 6H), 2.57 (s, 3H), 4.99 (sept, J=6.18 Hz, 1H), 7.40 (d, J=8.28 Hz, 2H), 7.58 (s, 2H), 7.62 (d, J=15.5 Hz, 1H), 7.82 (d, J=15.5 Hz, 1H), 8.10 (d, =8.28 Hz, 2H), 12.97 (s, 1H)

MS (Maldi-Tof): 427.1 (M+1)

Compound 29

1-[4-methylthiophenyl]-3-[3,5-dimethyl-4-carboxydimethylmethyloxyphenyl]prop-2-en-1-one

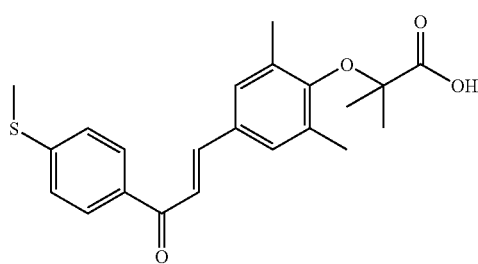

This compound was synthesized from 1-[4-methylthiophenyl]-3-[3,5-dimethyl-4-tertbutyloxycarbonyldimethylmethyloxyphenyl]prop-2-en-1-one (compound 28) according to general method 5 described earlier.

Purification was by chromatography on silica gel (elution: dichloromethane /methanol 98/2).

1H NMR DMSO δ ppm: 1.39 (s, 6H), 2.22 (s, 6H), 2.57 (s, 3H), 7.40 (d, J=8.55 Hz, 2H), 7.57 (s, 2H), 7.62 (d, J=15.5 Hz, 1H), 7.83 (d, J=15.5 Hz, 1H), 8.10 (d, J=8.55 Hz, 2H), 12.97 (s, 1H)

MS (ES-MS): 383.3(M−1)

Compound 30

1-[2-methoxyphenyl]-3-[3,5-dimethyl-4-tertbutyloxycarbonyldimethylmethyloxyphenyl]prop-2-en-1-one

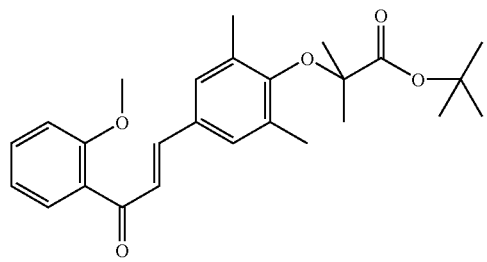

This compound was synthesized from 1-[2-methoxyphenyl]-3-[3,5-dimethyl-1-4-hydroxyphenyl]prop-2-en-1-one (intermediate compound 3) and tertbutyl bromoisobutyrate according to general method 4 described earlier.

Purification was by chromatography on silica gel (elution: cyclohexane/ethyl acetate 9:1).

Compound 31

1-[2-methoxyphenyl]-3-[3,5-dimethyl-4-carboxydimethylmethyloxyphenyl]prop-2-en-1-one

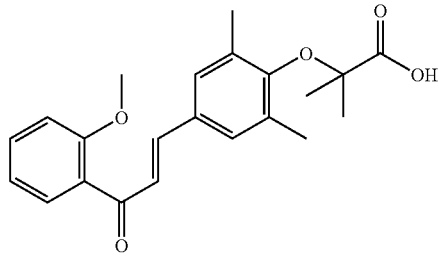

This compound was synthesized from 1-[2-methoxyphenyl]-3-[3,5-dimethyl-4-tertbutyloxycarbonyldimethylmethyloxyphenyl]prop-2-en-1-one (compound 30) according to general method 5 described earlier.

Purification was by chromatography on silica gel (elution: dichloromethane/methanol 98/2).

1H NMR DMSO δ ppm: 1.38 (s, 6H), 2.19 (s, 6H), 3.93 (s, 3H), 7.05 (m, 1H), 7.20 (d, J=8.31 Hz, 1H), 7.25 (d, J=15.5 Hz, 1H), 7.37 (d, J=15.5 Hz, 1H), 7.39 (s, 2H), 7.46 (d, J=7.2 Hz, 1H), 7.53 (m, 1H), 12.93 (s, 1H)

MS (ES-MS): 367.1(M−1)

Compound 32

1-[4-hexyloxyphenyl]-3-[3,5-dimethyl-4-tertbutyloxycarbonyldimethylmethyloxyphenyl]orop-2-en-1-one

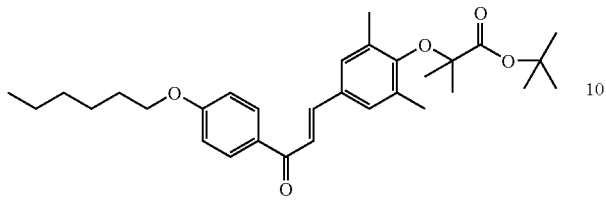

This compound was synthesized from 1-[4-hexyloxyphenyl]-3-[3,5-dimethyl-4-hydroxyphenyl]prop-2-en-1-one (intermediate compound 4) and tertbutyl bromoisobutyrate according to general method 4 described earlier.
Purification was by chromatography on silica gel (elution: cyclohexane/ethyl acetate 95/5).

Compound 33

1-[4-hexyloxyphenyl]-3-[3,5-dimethyl-4-carboxydimethylmethyloxyphenyl]prop-2-en-1-one

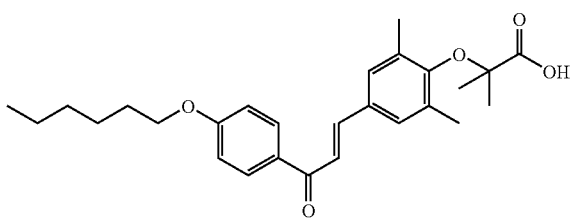

This compound was synthesized from 1-[4-hexyloxyphenyl]-3-[3,5-dimethyl-4-tertbutyloxycarbonyldimethylmethyloxyphenyl]prop-2-en-1-one (compound 32) according to general method 5 described earlier.
Purification was by recrystallization in methanol.
1H NMR DMSO δ ppm: 0.88 (t, J=6.33 Hz, 3H), 1.30 (m, 4H), 1.39 (s, 6H), 1.44 (m, 2H), 1.73 (m, 2H), 2.22 (s, 6H), 4.06 (t, J=6.30 Hz, 2H), 7.06 (d, J=8.61 Hz, 2H), 7.56 (s, 2H), 7.58 (d, J=15.5 Hz, 1H), 7.82 (d, J=15.5 Hz, 1H), 8.13 (d, J=6.61 Hz, 2H)
MS (ES-MS): 437.2(M−1)

Compound 34

2-(3,5-dimethyl-4-tertbutyloxycarbonvidimethyimethyloxyphenyl)-7-chloro-4H-1-benzopyran-4-one

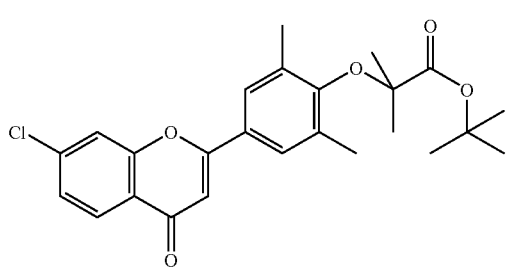

This compound was synthesized from 2-(3,5-dimethyl-4-hydroxyphenyl)-7-chloro-4H-1-benzopyran-4-one (intermediate compound 6) and tertbutyl bromoisobutyrate according to general method 4 described earlier. Purification was by precipitation in the solvent mixture dichloromethane/heptane.

Compound 35

2-(3,5-dimethyl-4-carboxydimethylmethyloxyphenyl)-7-chloro-4H-1-benzopyran-4-one

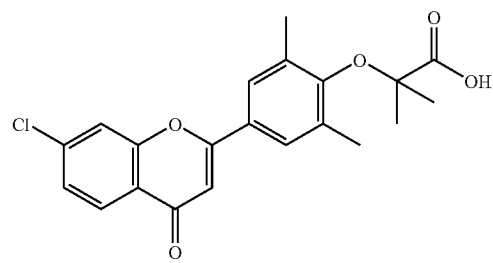

This compound was synthesized from 2-(3,5-dimethyl-4-tertbutyloxycarbonyldimethylmethyloxyphenyl)-7-chloro-4H-1-benzopyran-4-one (compound 34) according to general method 5 described earlier.
Purification was by preparative HPLC (reverse phase RP18, Licrospher 12 μm, elution: water/methanol/trifluoroacetic acid: 22/78/0.1).
1H NMR DMSO δ ppm: 1.24 (s, 6H), 2.28 (s, 6H), 7.02 (s, 1H), 7.56 (dd, J=8.71 Hz, J=1.75 Hz, 1H), 7.85 (s, 2H), 8.03 (d, J=1.75 Hz, 1H), 8.06 (d, J=8.71 Hz, 1H)
MS (Maldi-Tof): 387.1(M+1)

Compound 36

1-[2-methyloxy-4-chlorophenyl]-3-[3,5-dimethyl-4-tertbutyloxycarbonyldimethylmethyloxyphenyl]prop-2-en-1-one

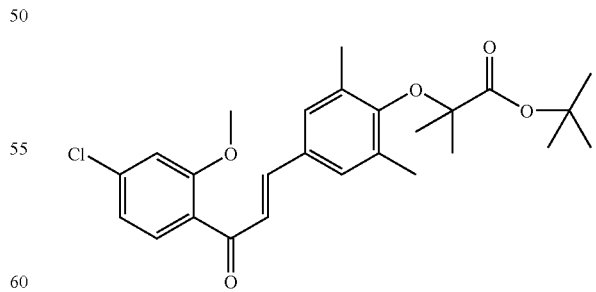

This compound was synthesized from 1-[2-methyloxy-4-chlorophenyl]-3-[3,5-dimethyl-4-hydroxydimethylmethyloxyphenyl]prop-2-en-1-one (intermediate compound 7) and tertbutyl bromoisobutyrate according to general method 4 described earlier.

Purification was by chromatography on silica gel (elution cyclohexane/ethyl acetate 9:1).

Compound 37

1-[2-methyloxy-4-chlorophenyl]-3-[3,5-dimethyl-4-carboxydimethylmethyloxyphenyl]prop-2-en-1-one

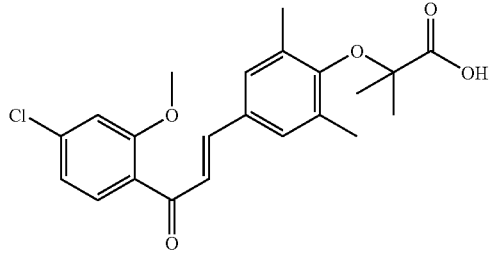

This compound was synthesized from 1-[2-methoxy-4-chlorophenyl]-3-[3,5-dimethyl-4-tertbutyloxycarbonyldimethylmethyloxyphenyl]prop-2-en-1-one (compound 36) according to general method 5 described earlier.

Purification was by chromatography on silica gel (elution: dichloromethane/methanol 98:2)

1H NMR DMSO δ ppm: 1.38 (s, 6H), 2.19 (s, 6H), 3.89 (s, 3H), 7.12 (dd, J=7.98 Hz, J=1.71 Hz, 1H), 7.23 (d, J=15.56 Hz, 1H), 7.29 (s, J=1.71 Hz, 1H), 7.38 (d, J=15.7 Hz, 1H), 7.41 (s, 2H), 7.48 (d, J=7.98 Hz, 1H)

MS (ES-SM): 401.2(M−1)

Compound 38

1-[4-heptylphenyl]-3-[3,5-dimethyl-4-tertbutyloxycarbonyldimethylmethyloxyphenyl]prop-2-en-1-one

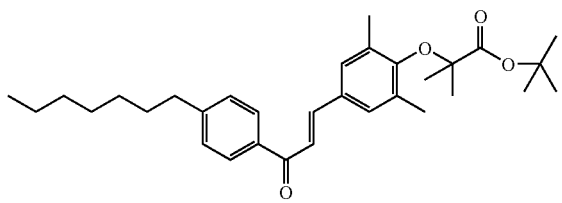

This compound was synthesized from 1-[4-heptylphenyl]-3-[3,5-dimethyl-4-hydroxyphenyl]prop-2-en-1-one (intermediate compound 9) and tertbutyl bromoisobutyrate according to general method 4 described earlier.

Purification by chromatography on silica gel (elution:cyclohexane/ethyl acetate 9/1)

Compound 39

1-[4-heptylphenyl]-3-[3,5-dimethyl-4-carboxydimethylmethyloxyphenyl]prop-2-en-1-one

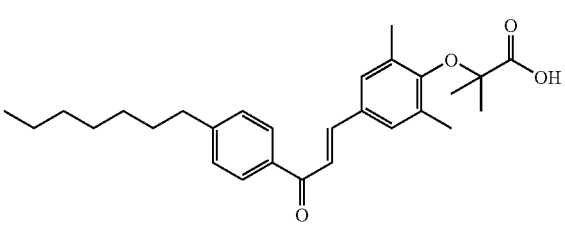

This compound was synthesized from 1-[4-heptylphenyl]-3-[3,5-dimethyl-4-tertbutyloxycarbonyldimethylmethyloxyphenyl]prop-2-en-1-one (compound 38) and tertbutyl bromoisobutyrate according to general method 4 described earlier.

Purification was by chromatography on silica gel (elution: dichloromethane/methanol 98/2)

1H NMR DMSO δ ppm: 0.85 (m, 3H), 1.30-1.24 (m, 8H), 1.39 (s, 6H), 1.60 (m, 2H), 2.22 (s, 6H), 2.67 (t, 2H, J=7.4 Hz), 7.37 (d, J=8.04 Hz, 2H), 7.57 (s, 2H), 7.62 (d, J=15.66 Hz, 1H), 7.82 (d, J=15.69 Hz, 1H), 8.07 (d, J=8.07 Hz, 2H)

MS (ES-MS): 435.3(M−1)

Compound 40

1-[4-bromophenyl]-3-[3,5-dimethyl-4-tertbutyloxycarbonyldimethylmethyloxyphenyl]prop-2-en-1-one

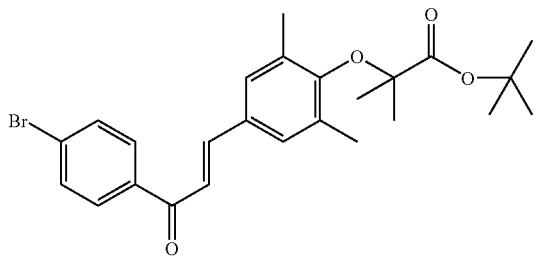

This compound was synthesized from 1-[4-bromophenyl]-3-[3,5-dimethyl-4-hydroxyphenyl]prop-2-en-1-one (intermediate compound 8) and tertbutyl bromoisobutyrate according to general method 4 described earlier.

Purification by chromatography on silica gel (elution: cyclohexane/ethyl acetate 9/1)

Compound 41

1-[4-bromophenyl]-3-[3,5-dimethyl-4-carboxy dimethylmethyloxyphenyl]prop-2-en-1-one

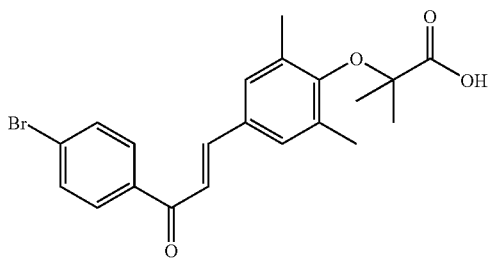

This compound was synthesized from 1-[4-bromophenyl]-3-[3,5-dimethyl-4-tertbutyloxycarbonyldimethylmethyloxyphenyl]prop-2-en-1-one (compound 40) according to general method 5 described earlier.

Purification was by chromatography on silica gel (elution: dichloromethane/methanol 98:2)

1H NMR DMSO δ ppm: 1.39 (s, 6H), 2.22 (s, 6H), 7.58 (s, 2H), 7.65 (d, J=15.39 Hz, 1H), 7.84-7.77 (m, 3H), 8.09 (d, J=8.19 Hz, 1H), 13.01 (s, 1H)

MS (ES-MS): 417.2 (M−1)

Compound 42

1-[2-hydroxyphenyl]-3-[3,5-dimethyl-4-isopropyloxycarbonyldimethylmethyloxyphenyl]prop-2-en-1-one

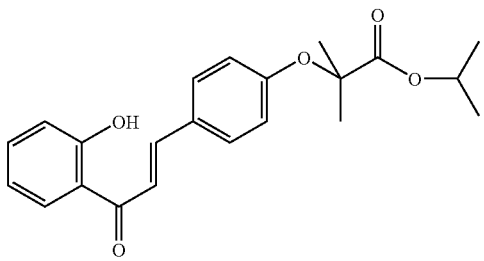

1-[2-hydroxyphenyl]-3-[4-carboxydimethylmethyloxyphenyl]prop-2-en-1-one (compound 4; 1 eq) was dissolved in dichloromethane. Dichloromethylmethyl ether (3 eq) was added and the mixture was kept under reflux for 8 hours. The solvent and excess reagent were eliminated by vacuum evaporation. The evaporation residue was taken up in isopropanol (50 eq) stirred for 12 hours at room temperature and the isopropanol was then eliminated by vacuum evaporation.

Purification was by chromatography on silica gel (elution: toluene/ethyl acetate 7:3)

1H NMR CDCl$_3$ δppm: 1.21 (d, J=6.09 Hz, 6 H), 1.65 (s, 6H), 5.10 (sept, J=6.10 Hz, 1H), 6.86 (d, J=8.65 Hz, 2H), 6.95 (m, 1H), 7.02 (dd, J=8.65 Hz, J=1.53 Hz, 1H), 7.48 (m, 1H), 7.54 (d, J=15.25 Hz, 1H), 7.57 (d, J=8.65 Hz, 2H), 7.87 (d, J=15.25 Hz, 1H), 7.93 (d, J=8.40 Hz, 1 H), 12.94 (signal exchangeable D$_2$O, 1H)

MS (Maldi-Tof): 369.1(M+1)

Example 2

Evaluation of PPAR Activation in vitro

The inventive compounds which were tested are the compounds whose preparation is described in the above examples.

Nuclear receptors of the PPAR subfamily which are activated by two major classes of pharmaceuticals—fibrates and glitazones, widely used in the clinic for the treatment of dyslipidemias and diabetes—play an important role in lipid and glucose homeostasis. The following experimental data show that the inventive compounds activate PPARα and PPARγ in vitro.

PPAR activation was tested in vitro in RK13 fibroblast cell lines by measuring the transcriptional activity of chimeras composed of the DNA binding domain of the yeast gal4 transcription factor and the ligand binding domain of the different PPARs. These latter results were then confirmed in cell lines according to the following protocols:

The example is given for RK13 cells.

a. Culture Protocols

RK13 cells were from ECACC (Porton Down, UK) and were grown in DMEM medium supplemented with 10% (VN) fetal calf serum, 100 U/ml penicillin (Gibco, Paisley, UK) and 2 mM L-glutamine (Gibco, Paisley, UK). The culture medium was changed every two days. Cells were kept at 37° C. in a humidified 95% air/5% CO$_2$ atmosphere.

b. Description of Plasmids Used for Transfection

The plasmids pG5TkpGL3, pRL-CMV, pGal4-hPPARα, pGal4-hPPARγ and pGal4-φ have been described by Raspe, Madsen et al. (1999). The pGal4-mPPARα and pGal4-hPPARγ constructs were obtained by cloning into the pGal4-φ vector of PCR-amplified DNA fragments corresponding to the DEF domains of the human PPARα and PPARγ nuclear receptors.

c. Transfection

RK13 cells were seeded in 24-well culture dishes at 5×10$^4$ cells/well and transfected for 2 hours with the reporter plasmid pG5TkpGL3 (50 ng/well), the expression vectors pGal4-φ, pGal4-mPPARα, pGal4-hPPARα, pGal4-hPPARγ (100 ng/well) and the transfection efficiency control vector pRL-CMV (1 ng/well) according to the previously described protocol (Raspe, Madsen et al. 1999), then incubated for 36 hours with the test compounds. At the end of the experiment, the cells were lysed (Gibco, Paisley, UK) and luciferase activity was determined with a Dual-Luciferase™ Reporter Assay System kit (Promega, Madison, Wis., USA) according to the supplier's instructions as previously described (Raspe, Madsen et al. 1999).

The inventors demonstrate an increase in luciferase activity in cells treated with the inventive compounds and transfected with the pGal4-hPPARα plasmid. Said induction of luciferase activity indicates that the inventive compounds are activators of PPARα.

The results are exemplified in FIGS. 2-1, 2-2, 2-3, 2-4, 2-5, 2-6 which illustrate the PPARα activator properties of inventive compounds 3, 4, 7, 8, 9, 11, 12, 13, 14, 17, 19, 20, 21, 22, 23, 24, 25, 26, 29, 31, 33, 37, 38, 41.

The inventors demonstrate an increase in luciferase activity in cells treated with the inventive compounds and transfected with the pGal4-hPPARγplasmid. Said induction of luciferase activity indicates that the inventive compounds are activators of PPARγ.

The results are exemplified in FIG. 2-7 which illustrates the PPARγactivator properties of inventive compounds 17, 33 and 29.

One aspect of the invention is illustrated by the treatment of diseases like atherosclerosis and psoriasis the manifestations of which are vascular and cutaneous, respectively. These two pathologies are characterized by chronic systemic inflammation and uncontrolled cell proliferation (smooth muscle cells in the case of atherosclerosis and epidermal keratinocytes in psoriasis). These two pathologies have in common the expression of inflammatory cytokines, mediated by a transcription factor of the inflammatory response NF-kB, AP-1 and NFAT (Komuves, Hanley et al. 2000; Neve, Fruchart et al. 2000). By down-regulating the NF-kB and AP-1 signalling pathway, PPARα inhibits the expression of genes involved in the inflammatory response such as the genes coding for interleukin-6, cyclooxygenase-2 and endothelin-1 and therefore impedes the mobilization of monocytes and spumous cells to the atheromatous lesions.

Example 3

Evaluation of the Effects on Lipid Metabolism in vivo

The inventive compounds which were tested are the compounds whose preparation is described in the above examples.

Fibrates, widely used in the clinic for the treatment of dyslipidemias underlying the development of atherosclerosis, one of the leading causes of morbidity and mortality in the industrialized world, are potent activators of the PPARα nuclear receptor, which regulates the expression of genes involved in lipid transport (apolipoproteins such as Apo AI, Apo AII and Apo CIII, membrane transporters such as FAT) and catabolism (ACO, CPT-I and CPT-II). In humans and rodents, treatment with PPARα activators therefore leads to a decrease in circulating levels of cholesterol and triglycerides.

The following protocols were designed to demonstrate a decrease in circulating triglyceride and cholesterol levels as well as the interest of the inventive compounds in a context of preventing and/or treating cardiovascular diseases.

a) Treatment of Animals

Apo E2/E2 transgenic mice were kept on a 12-hour light/dark cycle at a constant temperature of 20±3° C. After a 1 week acclimation, the mice were weighed and divided into groups of 6 animals selected so that body weight would be uniformly distributed. The test compounds were suspended in carboxymethylcellulose and administered by intragastric gavage at the indicated doses, once a day for 7 or 8 days. Animals had access to food and water ad libitum. At the end of the experiment the animals were weighed and sacrificed under anesthesia. Blood was collected on EDTA. Plasma was prepared by centrifugation at 3000 rpm for 20 minutes. Liver samples were taken and stored frozen in liquid nitrogen for subsequent analysis.

b) Measurement of Serum Lipids and Apolipoproteins

Serum lipid concentrations (total cholesterol and free cholesterol, triglycerides and phospholipids) were determined by a colorimetric assay (Boehringer, Mannheim, Germany) according to the supplier's instructions. Serum concentrations of apolipoproteins AI, AII and CIII were determined as previously described (Raspe et al. J. Lipid Res. 40, 2099-2110, 1999, Asset G et al., Lipids, 34, 39-44, 1999).

The results are exemplified in FIGS. 3-1, 3-2, 3-3, 3-4, 3-5, 3-6, 3-7, 3-8, 3-9, 3-10, 3-11 et 3-12 which illustrate the activity of inventive compounds 7, 17, 29, 33 and 41 on triglyceride and cholesterol metabolism.

c) RNA Analysis

Total RNA was isolated from liver specimens by extraction with a mixture of guanidine thiocyanate/acid phenol/chloroform according to the previously described protocol (Raspe et al. J. Lipid Res. 40, 2099-2110, 1999). Messenger RNA was quantified by quantitative RT-PCR with a Light Cycler Fast Start DNA Master Sybr Green I kit (Hoffman-La Roche, Basel, Switzerland) on a Light Cycler System (Hoffman-La Roche, Basel, Switzerland). Primer pairs specific for the genes ACO, Apo CIII and Apo AII were used as probes. Primer pairs specific for the genes 36B4, β-actin and cyclophilin were used as control probes. Alternatively, total RNA was analyzed by Northern Blot or Dot Blot according to the previously described protocol (Raspe et al. J. Lipid Res. 40, 2099-2110, 1999).

Example 4

Evaluation of the Antioxidant Properties of the Inventive Compounds

A particularly advantageous aspect of the invention is illustrated by the role of the intrinsic antioxidant properties of the compounds used in the inventive compositions in the control of oxidative stress. This original association between the PPARα agonist property and the antioxidant property represents an effective means of treating pathologies related to an alteration of the redox status of a cell. This illustration applies in particular to a pathology such as Alzheimer's disease in which free radicals play a decisive role.

In patients with Alzheimer's disease, oxidative status is modified in brain cells. Free radicals thus cause lipid peroxidation as well as oxidation of proteins and nucleic acids (DNA/RNA). Said oxidations alter the biological properties of biomolecules and lead to neuronal degeneration (Butterfield, Drake et al. 2001). NF-kB is a transcription factor known to be sensitive to the redox status of cells.

Therefore it is closely involved in the response to oxidative stress because it allows activation of the target genes of inflammation (Butterfield, Drake et al. 2001). The compounds used in the inventive compositions therefore have the original property of preventing activation of the NF-kB pathway at two different levels, by inhibiting its activation by free radicals (antioxidant) but also by preventing its transcriptional activity (PPARα agonist).

The inventive compounds represent a novel means of fighting against the effects of ageing and more particularly against the effects of UV-induced photo-ageing where free radicals actively participate in the pathogenesis of disorders ranging from skin erythema and wrinkle formation to more serious pathologies like skin cancer (basal cell and squamous cell carcinoma as well as melanoma).

Metabolism is what underlies the production of free radicals, but environmental factors like excitatory ionizing radiation (ultraviolet) or inflammatory mediators (cytokines), chemotherapeutic drugs, and hyperthermia are potent activators of free radical species and produce a disequilibrium in the redox balance of the cell. When the stress is severe, survival of the cell depends on its capacity to adapt, resist the stress and degrade damaged molecules. During ageing, the capacity of cells to defend themselves appropriately against an oxidative attack is crucial, and so an increase in cells' capacity to resist such attacks should help provide a solution to fight against the occurrence of the effects of ageing and should promote an increase in the longevity of the organism.

Solar radiation can alter the composition of certain molecules in the body. UVB was long considered to be the sole cause of the sun's deleterious effects on the body. It is now known that UVA radiation can have a direct adverse effect but above all that it potentiates the effects of UVB. The principal molecules vulnerable to alteration, often in a harmful way but also in a beneficial way, are:

DNA, in which thymine dimers can form under the action of UVB. Although DNA does not absorb UVA rays, the latter can damage the genetic material and therefore be mutagenic. A pathology such as *Xeroderma pigmentosum*, which is due to an absence or an alteration of DNA repair mechanisms, predisposes to the development of cancer of basal keratinocytes.

Proteins, the spatial conformation of which can be altered. Many proteins can be inactivated in this manner: enzymes, transporters, ion channels, cytoskeletal proteins, receptors. Said alterations can be induced by UVA and UVB radiation.

Lipids, which can undergo UVA-induced peroxidation, said peroxidation being proportional to the degree of fatty acid unsaturation.

The following protocols were designed to demonstrate the intrinsic antioxidant properties of the compounds used in the inventive compositions for prevention and/or treatment of disorders related to oxidative stress.

1. Protection against LDL Oxidation by Cooper:

The inventive compounds which were tested are the compounds whose preparation is described in the above examples.

LDL oxidation is an important alteration and plays a predominant role in the establishment and development of atherosclerosis (Jurgens, Hoff et al. 1987). The following protocol allows to demonstrate the antioxidant properties of compounds. Unless otherwise indicated, the reagents were from Sigma (St Quentin, France).

LDL were prepared according to the method described by Lebeau et al. (Lebeau, Furman et al. 2000).

The solutions of test compounds were prepared at $10^{-2}$ M concentration in bicarbonate buffer (pH 9) and diluted in PBS to obtain final concentrations ranging from 0.1 to 100 µM for a total ethanol concentration of 1% (VN).

Prior to oxidation, EDTA was removed from the LDL preparation by dialysis. Oxidation then took place at 30° C. by addition of 100 µl of 16.6 µM $CuSO_4$ solution to 160 µL of LDL (125 µg protein/ml) and 20 µl of a test compound solution. The formation of dienes, the species under observation, was followed by measuring optical density at 234 nm in the samples treated with the compounds but in the presence or absence of copper. Optical density at 234 nm was measured every 10 minutes for 8 hours in a thermostated spectrophotometer (Tecan Ultra 380). The analyses were performed in triplicate. The compounds were considered to have antioxidant activity when they induced a longer lag phase and reduced the rate of oxidation and the amount of dienes formed in comparison with the control sample. The inventors demonstrate that the inventive compounds have at least one of the above-described antioxidant properties indicating that the inventive compounds have intrinsic antioxidant activity. FIGS. 1, 2 and 3 give an example of the results illustrating the antioxidant properties of compounds 2 and 5.

Results are given in FIGS. 1-1, 1-2, 1-3, 1-4, 1-5, 1-6, 1-7, 1-8, 1-9, 1-10, 1-11, 1-12, 1-13 and 1-14 illustrating the antioxidant properties of inventive compounds 2, 3, 4, 5, 6, 7, 8, 9, 10, 14, 17, 18, 19, 21, 22, 25, 29, 31, 33, 35, 37, 38 and 41.

2. Evaluation of Protection Conferred by the Inventive Compounds against Lipid Peroxidation:

The inventive compounds which were tested are the compounds whose preparation is described in the above examples.

LDL oxidation was determined by the TBARS method.

According to the same principle described earlier, LDL were oxidized with $CuSO_4$ and lipid peroxidation was determined as follows:

TBARS were measured by a spectrophotometric method, lipid hydroperoxidation was measured using lipid-dependent peroxidation of iodide to iodine. The results are expressed as nmol of malondialdehyde (MDA) or as nmol of hydroperoxide/mg of protein.

The previous results obtained by measuring inhibition of conjugated diene formation were confirmed by the experiments measuring LDL lipid peroxidation.

The inventive compounds also effectively protected LDL against lipid peroxidation induced by copper (oxidizing agent).

BIBLIOGRAPHY

Braissant, O. and W. Wahli (1998). "Differential expression of peroxisome proliferator-activated receptor-alpha, -beta, and -gamma during rat embryonic development." *Endocrinology* 139(6): 2748-54.

Butterfield, D. A., J. Drake, et al. (2001). "Evidence of oxidative damage in Alzheimer's disease brain: central role for amyloid beta-peptide." *Trends Mol Med* 7(12): 548-54.

Desvergne, B. and W. Wahli (1999). "Peroxisome proliferator-activated receptors: nuclear control of metabolism." *Endocr Rev* 20(5): 649-88.

Finkel, T. and N. J. Holbrook (2000). "Oxidants, oxidative stress and the biology of ageing." *Nature* 408(6809): 239-47.

Fruchart, J. C., B. Staels, et al. (2001). "PPARS, metabolic disease and atherosclerosis." *Pharmacol Res* 44(5): 345-52.

Gilgun-Sherki, Y., E. Melamed, et al. (2001). "Oxidative stress induced-neurodegenerative diseases: the need for antioxidants that penetrate the blood brain barrier." *Neuropharmacology* 40(8): 959-75.

Guerre-Millo, M., P. Gervois, et al. (2000). "Peroxisome proliferator-activated receptor alpha activators improve insulin sensitivity and reduce adiposity." *J Biol Chem* 275(22): 16638-42.

Hourton, D., P. Delerive, et al. (2001). "Oxidized low-density lipoprotein and peroxisome-proliferator-activated receptor alpha down-regulate platelet-activating-factor receptor expression in human macrophages." *Biochem J* 354(Pt 1): 225-32.

Kliewer, S. A., S. S. Sundseth, et al. (1997). "Fatty acids and eicosanoids regulate gene expression through direct interactions with peroxisome proliferator-activated receptors alpha and gamma." *Proc Natl Acad Sci USA* 94(9): 4318-23.

Komuves, L. G., K. Hanley, et al. (2000). "Stimulation of PPARalpha promotes epidermal keratinocyte differentiation in vivo." *J Invest Dermatol* 115(3): 353-60.

Lebeau, J., C. Furman, et al. (2000). "Antioxidant properties of di-tert-butylhydroxylated flavonoids." *Free Radic Biol Med* 29(9): 900-12.

Mates, J. M., C. Perez-Gomez, et al. (1999). "Antioxidant enzymes and human diseases." *Clin Biochem* 32(8): 595-603.

Morliere, P., A. Moysan, et al. (1991). "UVA-induced lipid peroxidation in cultured human fibroblasts." *Biochim Biophys Acta* 1084(3): 261-8.

Neve, B. P., J. C. Fruchart, et al. (2000). "Role of the peroxisome proliferator-activated receptors (PPAR) in atherosclerosis." *Biochem Pharmacol* 60(8): 1245-50.

Ram V J (2003). "Therapeutic role of peroxisome proliferator-activated receptors in obesity, diabetes and inflammation. Prog Drug Res. 60: 93-132. Review Raspe, E., L. Madsen, et al. (1999). "Modulation of rat liver apolipoprotein gene expression and serum lipid levels by tetradecylthioacetic acid (TTA) via PPARalpha activation." *J Lipid Res* 40(11): 2099-110.

Staels, B. and J. Auwerx (1998). "Regulation of apo A-I gene expression by fibrates." *Atherosclerosis* 137 Suppl: S 19-23.

We claim:

1. A method of treatment of pathologies related to deregulations of lipid and/or glucose metabolism comprising administering to a subject in need thereof an effective amount of a pharmaceutical composition comprising one or more pharmaceutically acceptable excipients or vehicles and at least one substituted 1,3-diphenylprop-2-en-1-one derivative represented by formula (I) below:

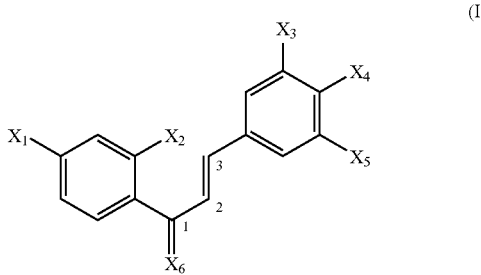

wherein:
X1 represents a halogen or a —R1 group or a group corresponding to the following formula: -G1-R1,
X2 represents a hydroxy or an unsubstituted alkyloxy group having from one to seven carbon atoms,
X3 represents a —R3 group,
X4 represents a group corresponding to the following formula: -G4-R4,
X5 represents a —R5 group,
X6 is an oxygen atom,
R1, R3, R5, which are the same or different, represent a hydrogen group or an unsubstituted alkyl group having from one to seven carbon atoms,
G1, G4, which are the same or different, represent an oxygen or sulfur atom,
R4 represents an alkyl group having from one to seven carbon atoms containing one substituent having the formula —COOR6, with R6 representing a hydrogen atom or an alkyl group having from one to seven carbon atoms,
and the optical and geometrical isomers, racemates, tautomers, salts and mixtures thereof;
said pathologies being selected from the group consisting of diabetes, atherosclerosis and obesity.

2. The method of claim 1, wherein both G1 and G4 represent an oxygen atom.

3. The method of claim 1, wherein X1 is a -G1-R1 group in which G1 is an oxygen atom and R1 is an unsubstituted alkyl group containing from two to seven carbon atoms.

4. The method of claim 1, wherein X1 represents a group corresponding to the formula -G1-R1, where G1 represents a sulphur atom and R1 is an unsubstituted alkyl group containing one or two carbon atoms.

5. The method of claim 1, wherein G4 is an oxygen atom, and X3 and X5 respectively represent R3 and R5, with R3 and R5 being alkyl groups having one or two carbon atoms.

6. The method of claim 1, wherein X1 represents a halogen.

7. The method of claim 1, wherein X4 represents —O—C(CH3)2-COOR6.

8. The method of claim 1, wherein X4 represents —O—C(CH3)2-COOH.

9. The method of claim 1, wherein the derivative is selected from the group consisting of:
1-[2-hydroxy-4-chlorophenyl]-3-[4-carboxydimethylmethyloxyphenyl]prop-2-en-1-one,
1-[2-hydroxyphenyl]-3-[4-carboxydimethylmethyloxyphenyl]prop-2-en-1-one,
1-[2-hydroxy-4-chlorophenyl]-3-[3,5-dimethyl-4-carboxydimethylmethyloxyphenyl]prop-2-en-1-one,
1-[2-hydroxyphenyl]-3-[3,5-dimethyl-4-carboxydimethylmethyloxyphenyl]prop-2-en-1-one,
1-[2,4-dihydroxyphenyl]-3-[4-carboxydimethylmethyloxyphenyl]prop-2-en-1-one,
1-[2-hydroxyphenyl]-3-[4-carboxydimethylmethylthiophenyl]prop-2-en-1-one,
1-[4-chloro-2-hydroxyphenyl]-3-[4-carboxydimethylmethylthiophenyl]prop-2-en-1-one,
1-[2-hydroxy-4-bromophenyl]-3-[3,5-dimethyl-4-carboxydimethylmethyloxyphenyl]prop-2-en-1-one,
1-[2-methoxyphenyl]-3-[3,5-dimethyl-4-tertbutyloxycarbonyldimethylmethyloxyphenyl]prop-2-en-1-one,
1-[2-methoxyphenyl]-3-[3,5-dimethyl-4-carboxydimethylmethyloxyphenyl]prop-2-en-1-one,
1-[2-methyloxy-4-chlorophenyl]-3-[3,5-dimethyl-4-tertbutyloxycarbonyldimethylmethyloxyphenyl]prop-2-en-1-one,
1-[2-methyloxy-4-chlorophenyl]-3-[3,5-dimethyl-4-carboxydimethylmethyloxyphenyl]prop-2-en-1-one,
1-[2-hydroxyphenyl]-3-[3,5-dimethyl-4-isopropyloxycarbonyldimethylmethyloxyphenyl]prop-2-en-1-one.

* * * * *